United States Patent
Mistry et al.

(10) Patent No.: US 10,620,211 B2
(45) Date of Patent: *Apr. 14, 2020

(54) HISTOCHEMICAL ASSAY FOR EVALUATING EXPRESSION OF PROGRAMMED DEATH LIGAND 1 (PD-L1)

(71) Applicant: Ventana Medical Systems, Inc., Tucson, AZ (US)

(72) Inventors: Amita T. Mistry, Oro Valley, AZ (US); Constantine M. Sabalos, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/663,640

(22) Filed: Jul. 28, 2017

(65) Prior Publication Data

US 2017/0343556 A1    Nov. 30, 2017

Related U.S. Application Data

(63) Continuation of application No. PCT/EP2016/052107, filed on Feb. 2, 2016.

(60) Provisional application No. 62/111,352, filed on Feb. 3, 2015.

(51) Int. Cl.
*G01N 33/574* (2006.01)
*C07K 16/28* (2006.01)

(52) U.S. Cl.
CPC ... *G01N 33/57492* (2013.01); *C07K 16/2827* (2013.01); *G01N 33/5743* (2013.01); *G01N 33/57423* (2013.01); *C07K 2317/565* (2013.01); *G01N 2333/70532* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,922,855 A | 7/1999 | Liskay et al. | |
| 6,803,192 B1 | 10/2004 | Chen | |
| 7,635,757 B2 | 12/2009 | Freeman et al. | |
| 7,754,208 B2 | 7/2010 | Ledbetter et al. | |
| 7,892,540 B2 | 2/2011 | Chen et al. | |
| 7,895,540 B2 | 2/2011 | Engin et al. | |
| 8,217,149 B2 | 7/2012 | Irving et al. | |
| 8,552,154 B2 | 10/2013 | Freeman et al. | |
| 8,981,063 B2 | 3/2015 | Chen | |
| 2002/0028487 A1 | 3/2002 | La Thangue et al. | |
| 2009/0317368 A1 | 12/2009 | Chen | |
| 2010/0203056 A1 | 8/2010 | Irving et al. | |
| 2011/0200620 A1 | 8/2011 | Chen et al. | |
| 2012/0039906 A1 | 2/2012 | Olive | |
| 2013/0034559 A1 | 2/2013 | Queva et al. | |
| 2013/0309250 A1* | 11/2013 | Cogswell | C07K 16/2827 424/172.1 |
| 2014/0341917 A1 | 11/2014 | Nastri et al. | |
| 2014/0356353 A1 | 12/2014 | Queva et al. | |
| 2015/0071910 A1* | 3/2015 | Kowanetz | C07K 16/2827 424/133.1 |
| 2015/0346208 A1* | 12/2015 | Couto | C07K 16/2827 435/7.21 |
| 2015/0346210 A1 | 12/2015 | Nitta et al. | |
| 2017/0372117 A1* | 12/2017 | Bredno | G06K 9/0014 |
| 2018/0031567 A1* | 2/2018 | Dennis | G01N 33/58 |
| 2018/0196055 A1* | 7/2018 | Couto | C07K 16/2827 |

FOREIGN PATENT DOCUMENTS

| | | |
|---|---|---|
| AU | 2012211347 A1 | 8/2012 |
| CN | 102250911 A | 11/2011 |
| CN | 102740887 A | 10/2012 |
| JP | 2012503984 A | 2/2012 |
| WO | 2001039722 A2 | 6/2001 |
| WO | 2010036959 A2 | 4/2010 |
| WO | 2010077634 A1 | 7/2010 |
| WO | 2011041613 A2 | 4/2011 |
| WO | 2011041613 A3 | 4/2011 |
| WO | 2012003476 A2 | 1/2012 |
| WO | 2013/079174 A1 | 6/2013 |
| WO | 2013172926 A1 | 11/2013 |
| WO | 2013173223 A1 | 11/2013 |
| WO | 2014022758 A1 | 2/2014 |

(Continued)

OTHER PUBLICATIONS

OptiView Detection Chemistry (Ventana Medical Systems, Inc. 2011) (Year: 2011).*
Rebellatto et al. (J. Clin. Oncology May 20, 2015 33 (15, Suppl. 1): Ab. No. 8033) (Year: 2015).*
"A Global Study to Assess the Effects of MEDI4736 Following Concurrent Chemoradiation in Patients With Stage III Unresectable Non-Small Cell Lung Cancer (PACIFIC)", U.S. National Institutes of Health, 2015, at ClinicalTrials.gov.
"A Global Study to Assess the Effects of MEDI4736 Following Concurrent Chemoradition in Patients With Stage III Unresectable Non-Small Cell Lung Cancer (PACIFIC)", published 2017 at https://clinicaltrials.gov/ct2/show/NCT02125461?term=medi4736+nsclc&rank=3.

(Continued)

*Primary Examiner* — Peter J Reddig
(74) *Attorney, Agent, or Firm* — Ventana Medical Systems, Inc.

(57) ABSTRACT

This disclosure relates to methods of assaying and scoring PD-L1 expression in tumors. Tumor samples are labeled with an antibody or antibody fragment that specifically binds to human PD-L1 and binding is detected. Binding intensity is compared to background, and tumor cells having membrane staining above background are counted. The percentage of tumor cells containing membrane staining of PD-L1 is determined and the tumor is classified as "PD-L1 positive" if the percentage of tumor cells falls above a predefined level.

10 Claims, 38 Drawing Sheets
(38 of 38 Drawing Sheet(s) Filed in Color)
Specification includes a Sequence Listing.

(56) References Cited

FOREIGN PATENT DOCUMENTS

| | | | |
|---|---|---|---|
| WO | 2014100079 A1 | 6/2014 | |
| WO | 2014/165422 A1 | 10/2014 | |
| WO | 2014165082 A2 | 10/2014 | |
| WO | 2014/194293 A1 | 12/2014 | |
| WO | 2015/013388 A2 | 1/2015 | |
| WO | 2015033172 A1 | 3/2015 | |
| WO | 2015033173 A1 | 3/2015 | |
| WO | 2015036499 A1 | 3/2015 | |
| WO | 2015038538 A1 | 3/2015 | |
| WO | 2015061668 A1 | 4/2015 | |
| WO | 2015088930 A1 | 6/2015 | |
| WO | 2015124703 A1 | 8/2015 | |
| WO | 2015181342 A1 | 12/2015 | |
| WO | WO-2015181343 A2 * | 12/2015 | ............. G01N 33/58 |

OTHER PUBLICATIONS

"Cancer Immunology: Pivotal Cancer Immunology Targets", published in 2017 at http://www.cellsignal.com/contents/science-cancer-research/pivotal-tumor-immunology-targets-pd-l1/pd-li-signaling.

"CD274 CD274 molecule [*Homo sapiens* (human)]," published 2015 at https://www.ncbi.nlm.nih.gov/gene/29126.

"Investigational Immunotherapy Anti-PDL1 (MPDL3280A) Shrank Tumors in 43 Percent of People With a Specific Type of Metastatic Bladder Cancer in a Genentech Study", published May 31, 2014 at www.gene.com/media/press-releases/14566/2014-05-31/investigational-immunotherapy-anti-pdl1-.

"Merck Serono Initiates Phase II Study of Anti-PD-L1 Antibody MSB0010718C in Metastatic Merkel Cell Carcinoma", published in 2017 at http://www.fiercebiotech.com/press-releases/merck-serono-initiates-phase-ii-study-anti-pd-l1-antibody-msb0010718c-metas.

"NCI Drug Dictionary", National Cancer Institute, 2015, at http://www.cancer.gov/publications/dictionaries.

"Pivotal Cancer Immunology Targets: New Rabbit mAbs for B7-H3 and B7-H4", in Cell Signaling Technology, at http://www.cellsignal.com/contents/science-cancer-research/pivotal-tumor-immunology-targets-pdl1/pd-li-signaling, www.cellsignal.com.

"UniProtKB—Q9NZQ7 [PD1L1_HUMAN]", published at http://www.uniprot.org/uniprot/Q9NZQ7, May 21, 2015.

Afanasiev et al, 2013, "Merkel Polyomavirus-Specific T Cells Fluctuate with Merkel Cell Carcinoma Burden and Express Therapeutically Targetable PD-1 and Tim-3 Exhaustion Markers", Clinical Cancer Research, 19(19):5351-5360.

Ali et al, 2015, "PD-L1 protein expression in breast cancer is rare, enriched in basal-like tumours and associated with infiltrating lymphocytes", Annals of Oncology, 26:1488-1493.

Almagro et al, 2008, "Humanization of Antibodies, Frontiers in Bioscience", 13:1619-1633.

Anonymous, Dual IHC on Discovery Ultra Research Instrument, Ventana Research Protocols, Jan. 1, 2014, URL: http://www.ventana.com/researchprotocols, XP055337858.

Anonymous, Dual IHC on Discovery Ultra Research Instrument, Ventana Research Protocols, Jan. 1, 2014, URL: http://www.ventana.com/researchprotocols, XP055337860.

Bendig, Mary M., 1995, "Humanization of Rodent Monoclonal Antibodies by CDR Grafting", Methods: A Companion to Methods in Enzymology, 8:83-93.

Berglund et al, 2008, "The Epitope space of the human proteome", Protein Science, 17:606-613.

Brahmer et al, 2012, "Safety and Activity of Anti-PD-L1 Antibody in Patients with Advanced Cancer", The New England Journal of Medicine, 366(26):2455-2465.

Brown et al, 2003, "Blockade of Programmed Death-1 Ligands on Dendritic Cells Enhances T Cell Activation and Cytokine Production", The Journal of Immunology, 170:1257-1266.

Brown, McKay et al., 1996, "Tolerance to Single, But Not Multiple, Amino Acid Replacements in Antibody VH CDR2 A Means of Minimizing B Cell Wastage from Somatic Hypermutation?", The Journal of Immunology, 156:3285-3291.

Butte et al, 2007, "Programmed Death-1 Ligand 1 Interacts Specifically with the B7-1 Costimulatory Molecule to Inhibit T Cell Responses", Immunity, 27:111-122.

Calles et al, 2014, "Differential expression of LKB1, PD-L1, and PD-L2 in KRAS-mutant non-small cell lung cancer in never-smokers", Journal of Clinical Oncology, 32(15):8032.

Carter et al, 2002, "PD-1:Pd-L inhibitory pathway affects both CD4 and CD8 T cells and is overcome by IL-2", European Journal of Immunology, 32:634-643.

Catalogue d'anticorps 2011, at www.abdserotec.com/france, p. 140.

Chakravarti et al, 2015, "Predictive factors of activity of anti-programmed death-1/ programmed death ligand-1 drugs: immunohistochemistry analysis", Translational Lung Cancer Research, 4:743-751.

Chen et al, 2012, "Molecular Pathways: Next-Generation Immunotherapy-Inhibiting Programmed Death-Ligand 1 and Programmed Death-1", Clinical Cancer Research, 18(24):6580-6587.

Chen et al, 2013, "PD-L1 Expression is Characteristic of a Subset of Aggressive B-cell Lymphomas and Virus-Associated Malignancies, Clinical Cancer Research", 19(13):3462-3473.

Cheong et al, 1996, "Unexpected Epithelial Membrane Antigen (EMA) and Cytokeratin Expression in a Case of Infantile Acute Monoblastic Leukaemia", Hematology, 1:223-225.

Choueiri et al, 2014, "Correlation of PD-L1 Tumor Expression and Treatment Outcomes in Patients with Renal Cell Carcinoma Receiving Sunitinib or Pazopanib: Results from COMPARZ, a Randomized Controlled Trial", Clinical Cancer Research, 21(5):1071-1077.

Colman, P. M., Effects of amino acid sequence changes on antibody-antigen interactions, Research in Immunology, 1994, pp. 33-36, vol. 145.

Corada et al, 2001, "Monoclonal antibodies directed to different regions of vascular endothelial cadherin extracellular domain affect adhesion and clustering of the protein and modulate endothelial permeability", Blood, 97(6):1679-1684.

De Genst et al, 2006, "Antibody repertoire development in camelids", Developmental and Comparative Immunology, 30:187-198.

Dong et al, 2002, "Tumor-associated B7-H1 promotes T-cell apoptosis: A potential mechanism of immune evasion", Nature Medicine, 8(8):793-800.

Freeman et al, 2000, "Engagement of the PD-1 Immunoinhibitory Receptor by a Novel B7 Family Member Leads to Negative Regulation of Lymphocyte Activation", Journal of Experimental Medicine, 192(7)1027-1034.

Gaiser et al, 2007, "Tyramide Signal Amplification: An Enhanced Method for Immunohistochemistry on Methyl-Methacrylate-Embedded Bone Marrow Trephine Sections", Acta Haematology, 117:122-127.

Ghebeh et al, 2006, "The B7-H1 (PD-L1) T Lymphocyte—Inhibitory Molecule Is Expressed in Breast Cancer Patients with Infiltrating Ductal Carcinoma: Correlation with Important High-Risk Prognostic Factors", Neoplasia, 8 (3):190-198.

Ghebeh et al, 2008, "FOXP3+ Tregs and B7-H1+/PD-1+ T lymphocytes co-infiltrate the tumor tissues of high-risk breast cancer patients: Implication for immunotherapy", BMC Cancer, 8:57.

Gustmann et al, 1991, "Cytokeratin Expression and Vimentin Content in Large Cell Anaplastic Lymphomas and other Non-Hodgkin's Lymphomas", American Journal of Pathology, 138(6):1413-1422.

Hamanishi et al, 2007, "Programmed cell death 1 ligand 1 and tumor-infiltrating CD8+ T lymphocytes are prognostic factors of human ovarian cancer", PNAS, 104(9):3360-3365.

Hamid et al, 2013, "Anti-programmed death-1 and anti-programmed death-ligand 1 antibodies in cancer therapy", Expert Opinion on Biological Therapy, 13(6):847-861.

International Preliminary Report on Patentability dated Dec. 6, 2016 in corresponding PCT/EP2015/061922 filed on May 29, 2015, pp. 1-9.

International Preliminary Report on Patentability dated Aug. 8, 2017 in corresponding PCT/EP2016/052107 filed on Feb. 2, 2016, pp. 1-8.

International Search Report and Written Opinion dated Dec. 22, 2015 in corresponding PCT/EP2015/061922 filed on May 29, 2015, pp. 1-13.

(56) References Cited

OTHER PUBLICATIONS

International Search Report and Written Opinion dated Apr. 5, 2016 in corresponding PCT/EP2016/052107 filed on Feb. 2, 2016, pp. 1-17.
International Search Report dated Feb. 23, 2015 in Application No. PCT/US2014/062149, 1 page.
Investigational Immunotherapy Anti-PDL1 (MPDL3280A) Shrank Tumors in 43 Percent of People With a Specific Type of Metastatic Bladder Cancer in a Genentech Study, Genentech: Press Releases, May 31, 2014, http://www.gene.com/media/press-releases.
Iwai et al, 2002, "Involvement of PD-L1 on tumor cells in the escape from host immune system and tumor immunotherapy by PD-L1 blockade", PNAS, 99(19):12293-12297.
Iwai, Y. et al., PD-1 blockade inhibits hematogenous spread of poorly immunogenic tumor cells by enhanced recruitment of effector T cells, International Immunology, 2004, 133-144, 17-2.
Kwak et al, 1996, "A convenient method for epitope competition analysis of two monoclonal antibodies for their antigen binding", Journal of Immunological Methods, 191:49-54.
Latchman et al, 2001, "PD-L2 is a second ligand for PD-1 and inhibits T cell activation", Nature Immunology, 2(3) 261-268.
Lloyd, R.C. et al., Phenotyping immune cells in-situ. An investigation of the spatial heterogeneity of specific immune cell phenotypes in the tumour microenvironment., Perkin Elmer_University of Manchester, (2014), URL:www.poster-submission.com/cdrom/download_poster/37/27814/1062P,-.
Lyford-Pike, S. et al., Evidence for a Role of the PD-1:PD-L1 Pathway in Immune Resistance of HPV-Associated Head and Neck Squamous Cell Carcinoma, Cancer Research, (2013), pp. 1733-1741, vol. 73.
McLaughlin et al, 2014, "Domain-specific PD-L1 protein measurement in non-small cell lung cancer (NSCI,C)," Journal of Clinical Oncology, 2014 ASCO Annual Meeting Abstracts, 32(1).
Mu et al, 2011, "High expression of PD-L1 in lung cancer may contribute to poor prognosis and tumor cells immune escape through suppressing tumor infiltrating dendritic cells maturation", Medical Oncology, 28:682-688.
Mullane et al, 2014, "PD-L1 expression in mononuclear cells and not in tumor cells, correlated with prognosis in metastatic urothelial carcinoma", Journal of Clinical Oncology, 32(15):4552.
Ogata et al, 2012, "Differences in blast immunophenotypes among disease types in myelodysplastic syndromes: A multicenter validation study", Leukemia Research, 36:1229-1236.
Ohigashi et al, 2005, "Clinical Signficance of Programmed Death-1 Ligand-1 and Programmed Death-1 Ligand-2 Expression in Human Esophageal Cancer", Clinical Cancer Research, 11(8):2947-2953.
Padlan, Eduardo A., 1996, "X-Ray Crystallography of Antibodies", Advances in Protein Chemistry, 49:57-133.
Paul, William E., Fundamental Immunology, 1993, pp. 292-295, Third Edition, Chapter 9, Raven Press, New York.
PD-L1 (E1L3N®) XP® Rabbit mAb #13684, published in 2017, at http://www.cellsignal.com/products/primary-antibodies/13684?id=proteomics&utm_source=Sales+Flyer&utm_medium=offline&utm_campaign=NPI&utm_content=PDL1.
Perkin, E., Multiplex Tissue Biomarkers in Context, Opal Multiplex Staining, (2014), URL:https://www.perkinelmer.com/lab-solutions/resources/docs/FLY_Opal-Multiplex-Staining.pdf,-.
Powderly et al, 2013, "Biomarkers and Associations With the Clinical Activity of PD-L1 Blockade in a MPDL3280A Study", ASCO Presentation, slides 9-14.
Ribas et al, 2014, "The Future of Cancer Therapy: Selecting Patients Likely to Respond to PD1/L1 Blockade", Clinical Cancer Research, 20:4982-4984.
Rudikoff, Stuart et al, Single amino acid substitution altering antigen-binding specificity, Proceedings of the National Academy of Sciences USA, 1982, pp. 1979-1983, vol. 79, No. 6.
Shen et al, "Impaired ICOSL in human myeloid dendritic cells promotes Th2 responses in patients with allergic rhinitis and asthma", Clinical & Experimental Allergy, 44(6):831-841, 2014.
Sznol et al, 2013, "Antagonist Antibodies to PD-1 and B7-H1 (PD-L1) in the Treatment of Advanced Human Cancer", Clinical Cancer Research, 19(5):1021-1034.
Taube et al, 2012, "Colocalization of Inflammatory Response with B7-H1 Expression in Human Melanocytic Lesions Supports an Adaptive Resistance Mechanism of Immune Escape", Science Translational Medicine, 4(127):127ra37.
Topalian et al, 2012, "Safety, Activity, and Immune Correlates of Anti-PD-1 Antibody in Cancer", The New England Journal of Medicine, 366(26):2443-2454.
Tumeh et al, 2014, "PD-1 blockade induces responses by inhibiting adaptive immune resistance", Nature, 515 (7528):568-571.
Tzartos et al, 1996, "Epitope Mapping by Antibody Competition: Methodology and Evaluation of the Validity of the Technique", Methods in Molecular Biology, 66:55-66. vol. 66.
Velcheti et al, 2014, "Programmed death ligand-1 expression in non-small cell lung cancer", Laboratory Investigation, 94:107-116.
Ventana Medical Systems, Inc., 3-25. Ventana Medical Systems, Inc. and MedImmune collaborate to develop a custom PD-L1 Assay for immunotherapy clinical trials, 2014, 2 pages.
Warford et al, 2014, "Antigen retrieval, blocking, detection and visualisation systems in immunohistochemistry: A review and practical evaluation of tyramide and rolling circle amplification systems", Methods, 70:28-33.
Weber et al, 2013, "Safety, Efficacy, and Biomarkers of Nivolumab With Vaccine in Ipilimumab-Refractory or -Naive Melanoma", Journal of Clinical Oncology, 31:4311-4318.
Xu et al, 2014, "Loss of Lkb1 and Pten Leads to Lung Squamous Cell Carcinoma with Elevated PD-L1 Expression", Cancer Cell, 25:590-604.
Yunmei et al, 2014, "VSIG4 expression on macrophages facilitates lung cancer development", Laboratory Investigation, 94:709-710.
Zhang et al, 2009, "PD-1/PD-L1 interactions inhibit antitumor immune responses in a murine acute myeloid leukemia model", Blood, 114(8):1545-1552.

* cited by examiner

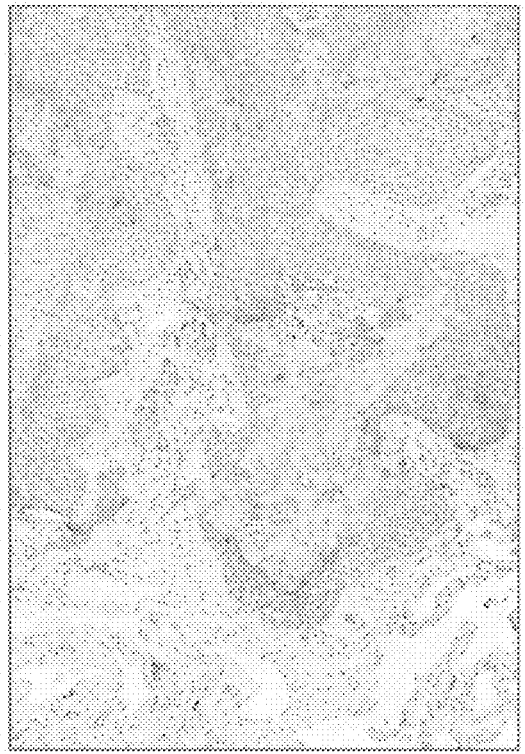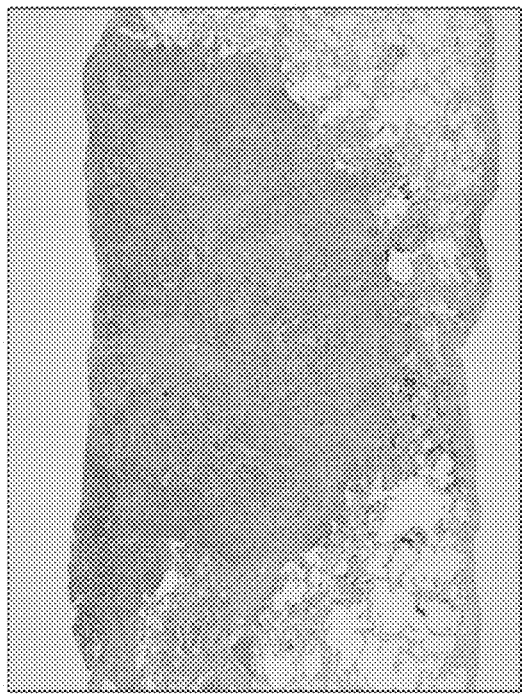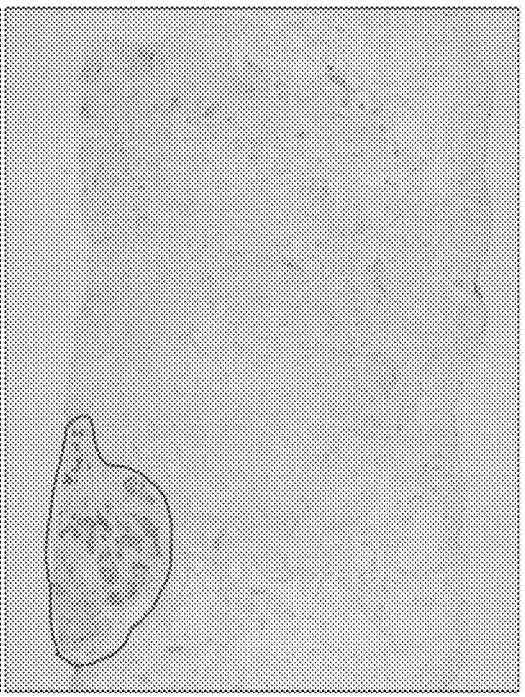
Fig. 28
Fig. 29

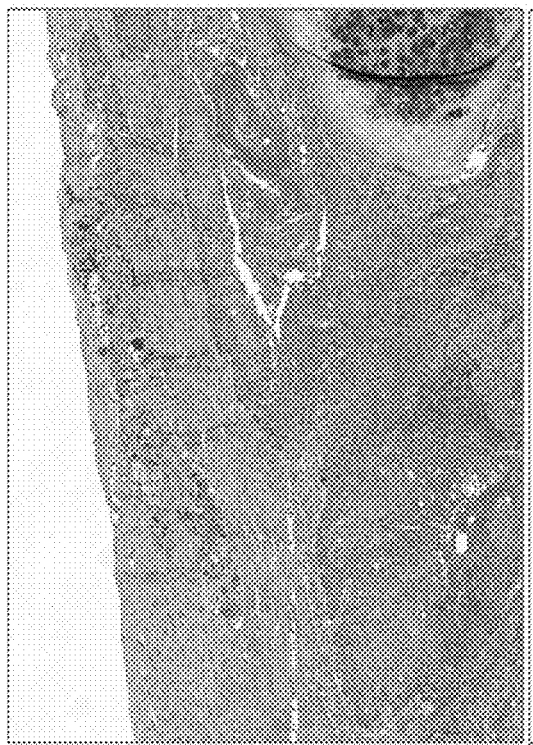
Fig. 30
Fig. 31

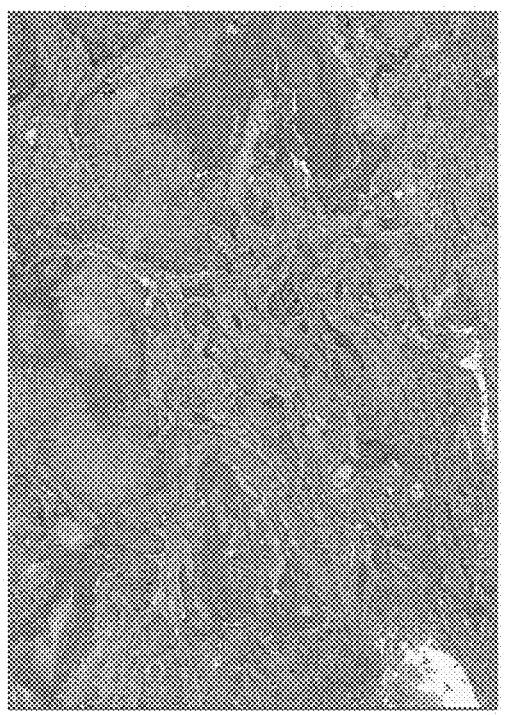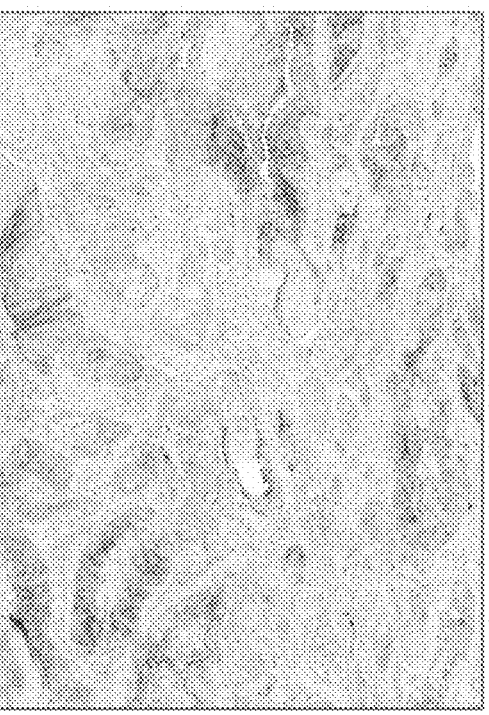
Fig. 32
Fig. 33

SEQUENCE LISTING

```
<160> NUMBER OF SEQ ID NOS: 9

<210> SEQ ID NO 1
<211> LENGTH: 5
<212> TYPE: PRT
<213> ORGANISM: Oryctolagus cuniculus

<400> SEQUENCE: 1

Asn His Ala Ile Ser
1               5

<210> SEQ ID NO 2
<211> LENGTH: 16
<212> TYPE: PRT
<213> ORGANISM: Oryctolagus cuniculus

<400> SEQUENCE: 2

Thr Ile Asn Ser Asp Thr His Thr Tyr Tyr Ala Thr Trp Pro Lys Gly
1               5                   10                  15

<210> SEQ ID NO 3
```

<211> LENGTH: 8
<212> TYPE: PRT
<213> ORGANISM: Oryctolagus cuniculus

<400> SEQUENCE: 3

Arg Ile Phe Ser Ser Ser Asn Ile
1               5

<210> SEQ ID NO 4
<211> LENGTH: 13
<212> TYPE: PRT
<213> ORGANISM: Oryctolagus cuniculus

<400> SEQUENCE: 4

Gln Ala Ser Gln Ser Ile Tyr Asn Asn Asn Trp Leu Ser
1               5                   10

<210> SEQ ID NO 5
<211> LENGTH: 7
<212> TYPE: PRT
<213> ORGANISM: Oryctolagus cuniculus

<400> SEQUENCE: 5

Leu Ala Ser Thr Leu Ala Ser
1               5

<210> SEQ ID NO 6
<211> LENGTH: 12
<212> TYPE: PRT
<213> ORGANISM: Oryctolagus cuniculus

<400> SEQUENCE: 6

Ile Gly Gly Glu Ser Ser Asn Asn Asp Gly Ile Ala
1               5                   10

<210> SEQ ID NO 7
<211> LENGTH: 114
<212> TYPE: PRT
<213> ORGANISM: Oryctolagus cuniculus

<400> SEQUENCE: 7

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Asn His Ala
            20                  25                  30

Ile Ser Trp Val Arg Gln Ala Pro Gly Lys Gly Leu Glu Trp Ile Gly
        35                  40                  45

Thr Ile Asn Ser Asp Thr His Thr Tyr Tyr Ala Thr Trp Pro Lys Gly
    50                  55                  60

Arg Phe Thr Ile Ser Lys Thr Ser Ser Thr Val Asp Leu Lys Met
65                  70                  75                  80

Thr Ser Pro Thr Thr Glu Asp Thr Ala Thr Tyr Phe Cys Ala Arg Arg
                85                  90                  95

Ile Phe Ser Ser Ser Asn Ile Trp Gly Pro Gly Thr Leu Val Thr Val
            100                 105                 110

Ser Ser

<210> SEQ ID NO 8
<211> LENGTH: 112
<212> TYPE: PRT
<213> ORGANISM: Oryctolagus cuniculus

```
-continued

<400> SEQUENCE: 8

Ala Ile Val Met Thr Gln Thr Ser Ser Pro Val Ser Ala Val Val Gly
1               5                   10                  15

Gly Thr Val Ala Ile Asn Cys Gln Ala Ser Gln Ser Ile Tyr Asn Asn
                20                  25                  30

Asn Trp Leu Ser Trp Phe Gln Gln Lys Pro Gly Gln Pro Pro Lys Leu
            35                  40                  45

Leu Ile Tyr Leu Ala Ser Thr Leu Ala Ser Gly Val Pro Ser Arg Phe
        50                  55                  60

Lys Gly Ser Gly Ser Gly Thr Gln Phe Thr Leu Thr Ile Ser Asp Val
65                  70                  75                  80

Val Cys Asp Asp Ala Ala Thr Tyr Tyr Cys Ile Gly Gly Glu Ser Ser
                85                  90                  95

Asn Asn Asp Gly Ile Ala Phe Gly Gly Gly Thr Glu Val Val Val Lys
            100                 105                 110

<210> SEQ ID NO 9
<211> LENGTH: 19
<212> TYPE: PRT
<213> ORGANISM: Homo sapiens

<400> SEQUENCE: 9

Cys Gly Ile Gln Asp Thr Asn Ser Lys Lys Gln Ser Asp Thr His Leu
1               5                   10                  15

Glu Glu Thr
```

HISTOCHEMICAL ASSAY FOR EVALUATING EXPRESSION OF PROGRAMMED DEATH LIGAND 1 (PD-L1)

CROSS-REFERENCE TO RELATED APPLICATIONS

This patent application is a continuation of International Patent Application No. PCT/EP2016/052107 filed Feb. 2, 2016, which claims priority to and the benefit of U.S. Provisional Patent Application No. 62/111,352, filed on Feb. 3, 2015. Each of the above patent applications is incorporated herein by reference as if set forth in its entirety.

SEQUENCE LISTING INCORPORATION BY REFERENCE

This application hereby incorporates-by-reference a sequence listing submitted herewith in a computer-readable format, having a file name of 32577US1_ST25, created on Jul. 28, 2017, which is 3,660 bytes in size.

BACKGROUND OF THE INVENTION

Technical Field

This disclosure relates to methods for detecting and scoring expression of Programmed Death Ligand-1 (PD-L1) in tumor tissues, particularly in conjunction with therapies that disrupt signaling initiated by PD-L1.

Brief Description of Related Art

Human PD-L1 encodes a 290 amino acid (aa) type I membrane precursor protein with a putative 18 aa signal peptide, a 221 aa extracellular domain, a 21 aa transmembrane region, and a 31 aa cytoplasmic domain. Human PD-L1 is constitutively expressed in several organs such as heart, skeletal muscle, placenta and lung, and in lower amounts in thymus, spleen, kidney and liver. PD-L1 expression is upregulated in a small fraction of activated T and B cells and a much larger fraction of activated monocytes. PD-L1 expression is also induced in dendritic cells and keratinocytes after IFN gamma stimulation.

PD-L1 is involved in the negative regulation of some immune responses and may play an important role in the regulation of peripheral tolerance. PD-L1 is known to bind to two receptors: Programmed cell death protein 1 (PD-1, also known as PCDP-1 and CD279); and B7-1 (also known as CD80). Interaction of PD-L1 with PD1 or with B7-1 results in inhibition of TCR-mediated proliferation and cytokine production (Freeman et al., J. Exp. Med. 192(7): 1027-34 (2000); Butte et al., Immunity 27(1): 111-22 (2007)). PD-L1 has been suggested to play a role in tumor immunity by increasing apoptosis of antigen-specific T-cell clones (Dong et al. Nat Med 8:793-800 (2002)). Indeed, PD-L1 expression has been found in several murine and human cancers, including human lung, ovarian and colon carcinoma and various myelomas (Iwai et al. PNAS 99:12293-7 (2002); Ohigashi et al. Clin Cancer Res 11:2947-53 (2005)). Thus, measuring the amount of PD-L1 protein in biological samples may aid in the early detection of cancer pathologies and may help assess the efficacy and durability of investigational drugs that inhibit the binding of the PD-L1 protein.

SUMMARY OF THE INVENTION

Provided herein are methods of evaluating PD-L1 expression in tumor samples based on the percentage of tumor cells that contain membrane staining of PD-L1.

In an embodiment, a histochemical method of classifying a tumor on the basis of PD-L1 expression is provided, the method comprising:
contacting a tissue sample from the tumor with an antibody specific for human PD-L1 or an antigen-binding fragment thereof in a manner that deposits a stain on the tumor sample in proximity to areas of the tumor sample to which the antibody binds, wherein the antibody comprises a heavy chain CDR1 comprising SEQ ID NO: 1, a heavy chain CDR2 comprising SEQ ID NO: 2, a heavy chain CDR3 comprising SEQ ID NO: 3, a light chain CDR1 comprising SEQ ID NO: 4, a light chain CDR2 comprising SEQ ID NO: 5, a light chain CDR3 comprising SEQ ID NO: 6;
quantitating a percentage of tumor cells having membrane-staining at any intensity above background; and
scoring the tumor for PD-L1 expression, wherein the tumor is scored as PD-L1 positive if the tumor cells having membrane-staining at any intensity above background exceeds a predetermined cutoff that correlates with a likelihood that the tumor will respond to a PD-1 axis binding therapeutic agent.

Exemplary antibodies can include heavy chains having a variable domain amino acid sequence comprising SEQ ID NO: 7 and/or a light chain having a variable domain amino acid sequence comprising SEQ ID NO: 8.

In an embodiment, the stain is deposited by contacting the tissue sample with a second antibody capable of binding to the antibody specific for human PD-L1, wherein the second antibody comprises a detectable label that mediates deposition of the stain. For example, where the antibody specific for human PD-L1 is a rabbit monoclonal antibody, and the second antibody can be an anti-rabbit Ig. In an exemplary embodiment, the detectable label comprises an affinity tag, and wherein deposition of the stain further comprises contacting the sample with a binding entity specific for the affinity tag, the binding entity comprising an enzyme that catalyzes deposition of the stain. Examples of affinity tags and binding entities include, for example, haptens and anti-hapten antibodies; biotin and avidin/streptavidin, and derivatives thereof; and the like.

In an embodiment, the stain is the result of a reaction between the enzyme and the chromogen. Exemplary chromogens include diaminobenzidine (DAB), 4-nitrophenylphospate (pNPP), fast red, bromochloroindolyl phosphate (BCIP), nitro blue tetrazolium (NBT), BCIP/NBT, fast red, AP Orange, AP blue, tetramethylbenzidine (TMB), 2,2'-azino-di-[3-ethylbenzothiazoline sulphonate] (ABTS), o-dianisidine, 4-chloronaphthol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazol (AEC), fuchsin, iodonitrotetrazolium (INT), tetrazolium blue and tetrazolium violet.

In an embodiment, the cutoff is determined empirically by evaluating a population of cancer patients treated with a PD-1 axis directed therapeutic. In an embodiment, the PD-1 axis directed therapeutic is an anti-human PD-L1 monoclonal antibody or an anti-human PD-1 monoclonal antibody. In an embodiment, the cancer is a head or neck cancer or a lung cancer. In another embodiment, the cancer is squamous cell carcinoma of the head and neck (SCCHN) or non-small cell lung carcinoma (NSCLC). In an embodiment, the cutoff is selected from a percentage in the range of 1% to 50% of tumor cells having membrane-staining at any intensity above background. In another embodiment, the cutoff is 25% of tumor cells having membrane-staining at any intensity above background. In one specific embodiment, the cancer is SCCHN or NSCLC, the PD-1 axis directed therapeutic is an anti-human PD-L1 monoclonal antibody, and the cutoff is 25% of tumor cells having membrane-staining at any intensity above background as determined by staining a serial section of the tissue sample from the tumor with an Ig control antibody, and wherein tumor cells having membrane-staining are identified by comparing the tissue sample contacted with the anti-human PD-L1 antibody with a serial section of the tumor stained with hematoxylin and eosin (H&E), and matching regions in the tissue sample contacted with the anti-human PD-L1 antibody that contain stain above background with regions bearing the morphological characteristics in the H&E-stained serial section.

In an embodiment, a method of classifying a tumor on the basis of PD-L1 expression is provided, the method comprising:
  labelling a tissue sample from the tumor with an antibody specific for PD-L1 or an antigen-binding fragment thereof (anti-PD-L1); and
  quantitating the percentage of tumor cells in the tissue sample containing anti-PD-L1 membrane staining at any staining intensity,
  wherein the tumor is considered PD-L1-positive when 25% or more of the tumor cells contain anti-PD-L1 membrane staining at any staining intensity above background. Preferably, the method does not comprise evaluating anti-PD-L1 staining of non-tumor cells.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

FIG. 28 illustrates an NSCLC stained with SP263 having tumor with 15% of cells showing membrane staining (outlined region). Tumor-associated immune cell staining also seen. (2×). Top image is H&E stain; bottom image is DAB stain.

FIG. 29 illustrates an NSCLC stained with SP263 having tumor with 20% of cells demonstrating membrane staining in this field. Tumor area contains 5% immune cells and 10% of immune cells with PD-L1 expression (10×). Top image is H&E stain; bottom image is DAB stain.

FIG. 30 illustrates an NSCLC stained with SP263 having tumor with 25% of cells demonstrating membrane staining in this field. Tumor area contains 5% immune cells and 5% of immune cells with PD-L1 expression (4×). Top image is H&E stain; bottom image is DAB stain.

FIG. 31 illustrates an NSCLC stained with SP263 having tumor with 35% of cells demonstrating membrane staining in this field. Tumor area (consisting of viable tumor and surrounding desmoplasia and inflammation) contains 10% immune cells and 5% of immune cells with PD-L1 expression (4×). Top image is H&E stain; bottom image is DAB stain.

FIG. 32 illustrates an NSCLC stained with SP263 having tumor with 50% of cells demonstrating membrane staining in this field. Tumor area (consisting of viable tumor and surrounding desmoplasia and inflammation) contains 10% immune cells and 5% of immune cells with PD-L1 expression (4×). Top image is H&E stain; bottom image is DAB stain.

FIG. 33 illustrates an NSCLC stained with SP263 having tumor with 70% of cells demonstrating membrane staining in this field. Tumor area contains 3% immune cells and 15% of immune cells with PD-L1 expression (4×). Top image is H&E stain; bottom image is DAB stain.

DETAILED DESCRIPTION OF THE INVENTION

Figure 1:
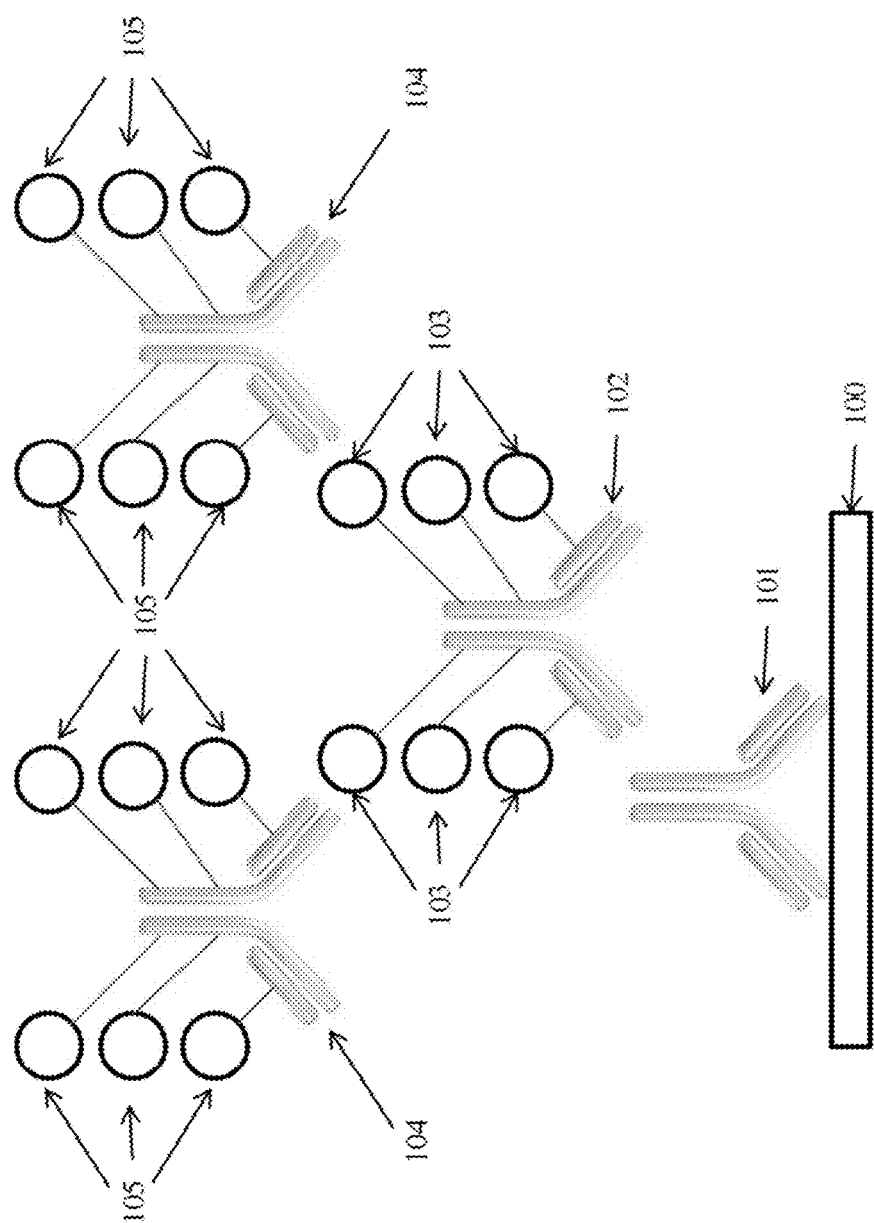
FIG. 1 illustrates a detection scheme useful in the present methods.

It is to be understood that this disclosure is not limited to particular aspects described, as such may, of course, vary. It is also to be understood that the terminology used herein is for the purpose of describing particular aspects only, and is not intended to be limiting, since the scope of the present disclosure will be limited only by the appended claims.

Unless defined otherwise, all technical and scientific terms used herein have the same meanings as commonly understood by one of ordinary skill in the art to which this disclosure belongs. Although any methods and materials similar or equivalent to those described herein can be used in the practice or testing of the present disclosure, the preferred methods, devices and materials are now described. All technical and patent publications cited herein are incorporated herein by reference in their entirety. Nothing herein is to be construed as an admission that the disclosure is not entitled to antedate such disclosure by virtue of prior disclosure.

The practice of the present technology will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, 3rd edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5th edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); and Herzenberg et al. eds (1996) Weir's Handbook of Experimental Immunology.

All numerical designations, e.g., pH, temperature, time, concentration and molecular weight, including ranges, are approximations which are varied (+) or (−) by increments of 1.0 or 0.1, as appropriate, or alternatively by a variation of +/−15%, or alternatively 10%, or alternatively 5% or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

It is to be inferred without explicit recitation and unless otherwise intended, that when the disclosure relates to a polypeptide, protein, polynucleotide or antibody, an equivalent or a biologically equivalent of such is intended within the scope of this disclosure.

As used in the specification and claims, the singular form "a", "an" and "the" include plural references unless the context clearly dictates otherwise. For example, the term "a cell" includes a plurality of cells, including mixtures thereof.

As used herein, the "administration" of an agent or drug to a subject or subject includes any route of introducing or delivering to a subject a compound to perform its intended function. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated and target cell or tissue. Non-limiting examples of route of administration include oral administration, vaginal, nasal administration, injection, topical application and by suppository. Administration includes self-administration and the administration by another. It is also to be appreciated that the various modes of treatment or prevention of medical conditions as described are intended to mean "substantial", which includes total but also less than total treatment or prevention, and wherein some biologically or medically relevant result is achieved.

Administration can be effected in one dose, continuously or intermittently throughout the course of treatment. Methods of determining the most effective means and dosage of administration are known to those of skill in the art and will vary with the composition used for therapy, the purpose of the therapy, the target cell being treated and the subject being treated. Single or multiple administrations can be carried out with the dose level and pattern being selected by the treating physician.

As used herein, the term "animal" refers to living multicellular vertebrate organisms, a category that includes, for example, mammals and birds. The term "mammal" includes both human and non-human mammals. Similarly, the term "subject" or "patient" includes both human and veterinary subjects, for example, humans, non-human primates, dogs, cats, sheep, mice, horses, and cows.

As used herein, the term "antibody" collectively refers to immunoglobulins or immunoglobulin-like molecules including by way of example and without limitation, IgA, IgD, IgE, IgG and IgM, combinations thereof, and similar molecules produced during an immune response in any vertebrate, for example, in mammals such as humans, goats, rabbits and mice, as well as non-mammalian species, such as shark immunoglobulins. The term "antibody" includes intact immunoglobulins and "antibody fragments" or "antigen binding fragments" that specifically bind to a molecule of interest (or a group of highly similar molecules of interest) to the substantial exclusion of binding to other molecules (for example, antibodies and antibody fragments that have a binding constant for the molecule of interest that is at least $10^3$ $M^{-1}$ greater, at least $10^4$ $M^{-1}$ greater or at least $10^5$ $M^{-1}$ greater than a binding constant for other molecules in a biological sample). The term "antibody" also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, J., Immunology, 3rd Ed., W.H. Freeman & Co., New York, 1997.

More particularly, "antibody" refers to a polypeptide ligand comprising at least a light chain or heavy chain immunoglobulin variable region which specifically recognizes and binds an epitope of an antigen. Antibodies are composed of a heavy and a light chain, each of which has a variable region, termed the variable heavy (VH) region and the variable light (VL) region. Together, the VH region and the VL region are responsible for binding the antigen recognized by the antibody.

Typically, an immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., Sequences of Proteins of Immunological Interest, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a VH CDR3 is located in the variable domain of the heavy chain of the antibody in which it is found, whereas a VL CDR1 is the CDR1 from the variable domain of the light chain of the antibody in which it is found. An antibody that binds PD-L1 will have a specific VH region and the VL region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

The term "antibody" is further intended to encompass digestion fragments, specified portions, derivatives and variants thereof, including antibody mimetics or comprising portions of antibodies that mimic the structure and/or function of an antibody or specified fragment or portion thereof, including single chain antibodies and fragments thereof. Examples of binding fragments encompassed within the term "antigen binding portion" of an antibody include a Fab fragment, a monovalent fragment consisting of the VL, VH, CL and CH, domains; a F(ab')2 fragment, a bivalent fragment comprising two Fab fragments linked by a disulfide bridge at the hinge region; a Fd fragment consisting of the VH and CH, domains; a Fv fragment consisting of the VL and VH domains of a single arm of an antibody, a dAb fragment (Ward et al. (1989) Nature 341:544$^{-5}$46), which consists of a VH domain; and an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)). Bird et al. (1988) Science 242:423-426 and Huston et al. (1988) Proc. Natl. Acad Sci. USA 85:5879$^{-5}$883. Single chain antibodies are also intended to be encompassed within the term "fragment of an antibody." Any of the above-noted antibody fragments are obtained using conventional techniques known to those of skill in the art, and the fragments are screened for binding specificity and neutralization activity in the same manner as are intact antibodies.

"Antibody fragments" or "antigen binding fragments" include proteolytic antibody fragments (such as F(ab')2 fragments, Fab' fragments, Fab'-SH fragments and Fab fragments as are known in the art), recombinant antibody fragments (such as sFv fragments, dsFv fragments, bispecific sFv fragments, bispecific dsFv fragments, F(ab)'2 fragments, single chain Fv proteins ("scFv"), disulfide stabilized Fv proteins ("dsFv"), diabodies, and triabodies (as are known in the art), and camelid antibodies (see, for example, U.S. Pat. Nos. 6,015,695; 6,005,079; 5,874,541; 5,840,526; 5,800,988; and 5,759,808). An scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains.

As used herein, the term "antigen" refers to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, and proteins. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens.

As used herein, "binding affinity" refers to the tendency of one molecule to bind (typically non-covalently) with another molecule, such as the tendency of a member of a specific binding pair for another member of a specific binding pair. A binding affinity can be measured as a binding constant, which binding affinity for a specific binding pair (such as an antibody/antigen pair) can be at least $1 \times 10^{-5}$ M, at least $1 \times 10^{-6}$ M, at least $1 \times 10^{-7}$ M, at least $1 \times 10^{-8}$ M, at least $1 \times 10^{-9}$ M, at least $1 \times 10^{-10}$ M, at least $1 \times 10^{-11}$ M or at least $1 \times 10^{-12}$ M. In one aspect, binding affinity is calculated by a modification of the Scatchard method described by Frankel et al., Mol. Immunol., 16:101-106, 1979. In another aspect, binding affinity is measured by an antigen/antibody dissociation rate. In yet another aspect, a high binding affinity is measured by a competition radioimmunoassay. In several examples, a high binding affinity for an antibody/antigen pair is at least about $1 \times 10^{-8}$ M. In other aspects, a high binding affinity is at least about $1.5 \times 10^{-8}$ M, at least about $2.0 \times 10^{-8}$ M, at least about $2.5 \times 10^{-8}$ M, at least about $3.0 \times 10^{-8}$ M, at least about $3.5 \times 10^{-8}$ M, at least about $4.0 \times 10^{-8}$ M, at least about $4.5 \times 10^{-8}$ M, or at least about $5.0 \times 10^{-8}$ M.

The terms "cancer," "neoplasm," and "tumor," used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by such procedures as CAT scan, magnetic resonance imaging (MRI), X-ray, ultrasound or palpation. Biochemical or immunologic findings alone may be insufficient to meet this definition.

A neoplasm is an abnormal mass or colony of cells produced by a relatively autonomous new growth of tissue.

Most neoplasms arise from the clonal expansion of a single cell that has undergone neoplastic transformation. The transformation of a normal to a neoplastic cell can be caused by a chemical, physical, or biological agent (or event) that directly and irreversibly alters the cell genome. Neoplastic cells are characterized by the loss of some specialized functions and the acquisition of new biological properties, foremost, the property of relatively autonomous (uncontrolled) growth. Neoplastic cells pass on their heritable biological characteristics to progeny cells.

The past, present, and future predicted biological behavior, or clinical course, of a neoplasm is further classified as benign or malignant, a distinction of great importance in diagnosis, treatment, and prognosis. A malignant neoplasm manifests a greater degree of autonomy, is capable of invasion and metastatic spread, may be resistant to treatment, and may cause death. A benign neoplasm has a lesser degree of autonomy, is usually not invasive, does not metastasize, and generally produces no great harm if treated adequately.

Cancer is a generic term for malignant neoplasms. Anaplasia is a characteristic property of cancer cells and denotes a lack of normal structural and functional characteristics (undifferentiation).

A tumor is literally a swelling of any type, such as an inflammatory or other swelling, but modern usage generally denotes a neoplasm.

Histogenesis is the origin of a tissue and is a method of classifying neoplasms on the basis of the tissue cell of origin. Adenomas are benign neoplasms of glandular epithelium. Carcinomas are malignant tumors of epithelium. Sarcomas are malignant tumors of mesenchymal tissues. One system to classify neoplasia utilizes biological (clinical) behavior, whether benign or malignant, and the histogenesis, the tissue or cell of origin of the neoplasm as determined by histologic and cytologic examination. Neoplasms may originate in almost any tissue containing cells capable of mitotic division. The histogenetic classification of neoplasms is based upon the tissue (or cell) of origin as determined by histologic and cytologic examination.

As used in this context a "tumor cell" refers to a neoplastic cell. Neoplastic cells can be distinguished from other cells histologically on the basis of morphology, as would be well-known by persons of ordinary skill in the art. Such methods may include manual inspection by a skilled pathologist or automated methods.

As used herein, the term "chimeric antibody" means an antibody in which the Fc constant region of a monoclonal antibody from one species (e.g., a mouse Fc constant region) is replaced, using recombinant DNA techniques, with an Fc constant region from an antibody of another species (e.g., a human Fc constant region). See generally, Robinson et al., PCT/US86/02269; Akira et al., European Patent Application 184,187; Taniguchi, European Patent Application 171,496; Morrison et al., European Patent Application 173,494; Neuberger et al., WO 86/01533; Cabilly et al. U.S. Pat. No. 4,816,567; Cabilly et al., European Patent Application 125, 023; Better et al., Science 240: 1041-$^{10}$43, 1988; Liu et al., Proc. Natl. Acad. Sci. USA 84: 3439-3443, 1987; Liu et al., J. Immunol. 139: 3521-3526, 1987; Sun et al., Proc. Natl. Acad. Sci. USA 84: 214-218, 1987; Nishimura et al., Cancer Res 47: 999-$^{10}$05, 1987; Wood et al., Nature 314: 446-449, 1885; and Shaw et al., J. Natl. Cancer Inst. 80: 1553-1559, 1988. In certain aspects the target binding region or site will be from a non-human source (e.g. mouse or primate) and the constant region is human.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. For example, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this disclosure. Aspects defined by each of these transition terms are within the scope of this disclosure.

As used herein, the term "detectable label" refers to a molecule or material that can produce a detectable (such as visually, electronically or otherwise) signal that indicates the presence and/or concentration of the label in a sample. When conjugated to a specific binding molecule, the detectable label can be used to locate and/or quantify the target to which the specific binding molecule is directed. Thereby, the presence and/or concentration of the target in a sample can be detected by detecting the signal produced by the detectable label. A detectable label can be detected directly or indirectly, and several different detectable labels conjugated to different specific-binding molecules can be used in combination to detect one or more targets. For example, a first detectable label conjugated to an antibody specific to a target can be detected indirectly through the use of a second detectable label that is conjugated to a molecule that specifically binds the first detectable label. Multiple detectable labels that can be separately detected can be conjugated to different specific binding molecules that specifically bind different targets to provide a multiplexed assay that can provide simultaneous detection of the multiple targets in a sample. A detectable signal can be generated by any mechanism including absorption, emission and/or scattering of a photon (including radio frequency, microwave frequency, infrared frequency, visible frequency and ultra-violet frequency photons). Detectable labels include colored, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected through antibody-hapten binding interactions using additional detectably labeled antibody conjugates, and paramagnetic and magnetic molecules or materials. Particular examples of detectable labels include enzymes such as horseradish peroxidase, alkaline phosphatase, acid phosphatase, glucose oxidase, $\beta$-galactosidase or $\beta$-glucuronidase; fluorophores such as fluoresceins, luminophores, coumarins, BODIPY dyes, resorufins, and rhodamines (many additional examples of fluorescent molecules can be found in The Handbook—A Guide to Fluorescent Probes and Labeling Technologies, Molecular Probes, Eugene, Oreg.); nanoparticles such as quantum dots (obtained, for example, from QuantumDot Corp, Invitrogen Nanocrystal Technologies, Hayward, Calif.; see also, U.S. Pat. Nos. 6,815,064, 6,682,596 and 6,649,138, each of which patents is incorporated by reference herein); metal chelates such as DOTA and DPTA chelates of radioactive or paramagnetic metal ions like Gd 3+; and liposomes, for example, liposomes containing trapped fluorescent molecules. Where the detectable label includes an enzyme, a detectable substrate such as a chromogen, a fluorogenic compound, or a luminogenic compound can be used in combination with the enzyme to generate a detectable signal (A wide variety of such compounds are commercially available, for example, from Invitrogen Corporation, Eugene Oreg.). Particular examples of chromogenic compounds include diaminobenzidine (DAB), 4-nitrophenylphospate (pNPP), fast red, bromochloroindolyl phosphate (BCIP), nitro blue tetrazolium (NBT), BCIP/NBT, fast red, AP Orange, AP blue, tetramethylbenzidine (TMB), 2,2'-azino-di-[3-ethylbenzothiazoline sulphonate] (ABTS), o-dianisidine, 4-chloronaphthol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino$^{-9}$-ethyl carbazol (AEC), fuchsin, iodonitrotetrazolium (INT), tetrazolium blue and tetrazolium violet. Alternatively, an enzyme can be used in a metallographic detection scheme. Metallographic detection methods include using an enzyme such as alkaline phosphatase in combination with a water-soluble metal ion and a redox-inactive substrate of the enzyme. The substrate is converted to a redox-active agent by the enzyme, and the redox-active agent reduces the metal ion, causing it to form a detectable precipitate. (See, for example, co-pending U.S. patent application Ser. No. 11/015,646, filed Dec. 20, 2004, PCT Publication No. 2005/003777 and U.S. Patent Application Publication No. 2004/0265922; each of which is incorporated by reference herein). Metallographic detection methods include using an oxido-reductase enzyme (such as horseradish peroxidase) along with a water soluble metal ion, an oxidizing agent and a reducing agent, again to form a detectable precipitate. (See, for example, U.S. Pat. No. 6,670,113, which is incorporated by reference herein). Haptens are small molecules that are specifically bound by antibodies, although by themselves they will not elicit an immune response in an animal and must first be attached to a larger carrier molecule such as a protein to generate an immune response. Examples of haptens include di-nitrophenyl, biotin, digoxigenin, and fluorescein. Additional examples of oxazole, pyrazole, thiazole, nitroaryl, benzofuran, triperpene, urea, thiourea, rotenoid, coumarin and cyclolignan haptens are disclosed in U.S. Provisional Patent Application No., 60/856,133, filed Nov. 1, 2006, which is incorporated by reference herein.

As used herein, an "epitope" or "antigenic determinant" refers to particular chemical groups or contiguous or non-contiguous peptide sequences on a molecule that are antigenic, i.e., that elicit a specific immune response. An antibody binds a particular antigenic epitope. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

The term "human antibody" as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo). However, the term "human antibody" as used herein, is not intended to include antibodies in which CDR sequences derived from the germline of another mammalian species, such as a rabbit, have been grafted onto human framework sequences. Thus, as used herein, the term "human antibody" refers to an antibody in which substantially every part of the protein (e.g., CDR, framework, CL, CH domains (e.g., CH1, CH2, CH3), hinge, VL, VH) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, the term "humanized antibody" refers to an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

As used herein, the term "humanized immunoglobulin" refers to an immunoglobulin including a human framework region and one or more CDRs from a non-human (for example a mouse, rat, rabbit or synthetic) immunoglobulin. The non-human immunoglobulin providing the CDRs is termed a "donor," and the human immunoglobulin providing the framework is termed an "acceptor." In one aspect, all the CDRs are from the donor immunoglobulin in a humanized immunoglobulin. Constant regions need not be present, but if they are, they must be substantially identical to human immunoglobulin constant regions, i.e., at least about 85%, or at least about 95% or more identical. Hence, all parts of a humanized immunoglobulin, except possibly the CDRs, are substantially identical to corresponding parts of natural human immunoglobulin sequences.

As used herein, the term "monoclonal antibody" refers to an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

As used herein, "PD-L1" (Programmed death ligand-1) or "B7-H1" (Human B7 homolog 1), or PDCD1L1 (Programmed cell death 1 ligand 1) is a member of the growing B7 family of immune proteins that provide signals for both stimulating and inhibiting T cell activation. Human PD-L1 encodes a 290 amino acid (aa) type I membrane precursor protein with a putative 18 aa signal peptide, a 221 aa extracellular domain, a 21 aa transmembrane region, and a 31 aa cytoplasmic domain (Entrez Gene ID: 29126, UniProtKB: Q9NZQ7).

As used herein, "PD-1", "PDCD1" (Programmed cell death protein 1) or "CD279" is an inhibitory cell surface receptor involved in the regulation of T-cell function during immunity and tolerance. Human PD-1 encodes a 288 amino acid (aa) single pass Type I cell surface membrane protein of the immunoglobulin superfamily with a putative 20 aa signal peptide, a 150 aa extracellular domain, a 21 aa transmembrane region, and a 97 aa cytoplasmic domain (Entrez Gene ID: 5133; UniProtKB: Q15116).

As used herein, "CD80" (T-lymphocyte activation antigen CD80), "Activation B7-1 antigen", "BB1", "B7" or (CTLA-4 counter-receptor B7.1) is involved in co-stimulatory signals essential for T-lymphocyte activation. Human CD80 encodes a 288 amino acid (aa) single pass cell membrane receptor protein with a putative 34 aa signal peptide, a 208 aa extracellular domain, a 21 aa transmembrane region, and a 25 aa cytoplasmic domain (Entrez Gene ID: 941; UniProtKB: P33681).

As used herein, the term "specific binding" means the contact between an antibody and an antigen with a binding affinity of at least $10^{-6}$ M. In certain aspects, antibodies bind with affinities of at least about $10^{-7}$ M, and preferably $10^{-8}$ M, $10^{-9}$ M, $10^{-10}$ M, $10^{-11}$ M, or $10^{-12}$ M.

As used herein, "SP263" refers to a monoclonal antibody that specifically binds to the cytoplasmic domain of PD-L1 and has CDR sequences as disclosed in Table 1:

TABLE 1

|  | CDR1 | CDR2 | CDR3 |
|---|---|---|---|
| Heavy Chain | NHAIS (SEQ ID NO: 1) | TINSDTHTYYATWP KG (SEQ ID NO: 2) | RIFSSSNI (SEQ ID NO: 3) |
| Light Chain | QASQSIYNNNWLS (SEQ ID NO: 4) | LASTLAS (SEQ ID NO: 5) | IGGESSNNDGIA (SEQ ID NO: 6) |

The full heavy and light chain variable domain sequences are as follows:

```
SP263 HC immunoglobulin variable domain
sequence:
                                 (SEQ ID NO: 7)
QSLEESGGRLVTPGTPLTLTCTASGFSLSNHAISWVRQ

APGKGLEWIGTINSDTHTYYATWPKGRFTISKTSSTTV

DLKMTSPTTEDTATYFCARRIFSSSNIWGPGTLVTVSS

SP263 LC immunoglobulin variable domain
sequence (kappa):
                                 (SEQ ID NO: 8)
AIVMTQTSSPVSAVVGGTVAINCQASQSIYNNNWLSWF

QQKPGQPPKLLIYLASTLASGVPSRFKGSGSGTQFTLT

ISDVVCDDAATYYCIGGESSNNDGIAFGGGTEVVVK
```

The present methods relate to methods for histochemically or immunohistochemically assaying, evaluating, and scoring PD-L1 expression in tumor samples. To this end, tumor samples are labeled with an entity capable of specifically staining PD-L1 protein in a manner that is detectable histologically. One way in which this is accomplished is by labeling the tumor samples with antibodies or antigen-binding fragments thereof that specifically bind to PD-L1 (anti-PD-L1). Examples of anti-PD-L1 are disclosed in, for example, U.S. 62/069,420, the contents of which are hereby incorporated by reference in its entirety.

Anti-PD-L1 antibodies and antibody fragments that are useful in these methods are: (1) capable of specifically binding to PD-L1; (2) capable of generating strong membrane staining in PDL1-positive tissue; and (3) low to no background staining (such as nuclear staining). One example of such an antibody is SP263, which is disclosed in U.S. 62/069,420. SP263 was developed using a peptide sequence consisting of amino acid residues 272-290 of human PD-L1 (CGIQDTNSKKQSDTHLEET (SEQ ID NO: 9)) covalently conjugated to a keyhole limpet haemocyanin (KLH) carrier protein to immunize New Zealand white rabbits. The CDR sequences of SP263 are disclosed in Table 1. Other examples of anti-PD-L1, both currently existing and not yet developed, will be immediately apparent to the person of ordinary skill in the art.

The tumor samples can be labeled with the anti-PD-L1 by automated or manual methods. Devices for automated labeling of tissue samples for immunohistochemistry are well known in the art, including, for example, the BENCHMARK series of IHC/ISH advanced staining instruments from Ventana Medical Systems, the OMNI and AUTOSTAINERLINK advanced staining instruments from Dako, and the BOND advanced staining systems from Leica Biosystems.

Binding of the anti-PD-L1 to the tumor sample is detected by contacting the tissue sample with a detectably-labeled entity capable of specifically binding to the anti-PD-L1. Numerous detection schemes are known in the art, including, for example, primary-secondary labeling schemes, wherein the anti-PD-L1 is contacted with a secondary antibody capable of specifically binding to the anti-PD-L1 (e.g. using a rabbit monoclonal antibody IgG as the primary and a detectably labeled anti-rabbit IgG antibody as the secondary); and binding-pair labeling schemes, wherein the primary antibody contains a moiety bound thereto that forms a specific binding pair with a detectably labeled second binding moiety (e.g. detecting biotinylated primary antibodies using detectably labeled biotin-binding entities, such as avidin or streptavidin).

In one specific embodiment, binding of the anti-humanPD-L1 to the tumor sample is accomplished using a secondary antibody conjugated with non-endogenous haptens. An anti-hapten antibody conjugated to one or more detectable labels (such as an enzyme capable of catalyzing a reaction depositing a chromogen). An example of such as scheme is the VENTANA OptiView DAB IHC detection kit. A schematic of this detection kit is presented at FIG. 1. A formalin-fixed, paraffin embedded tissue sample (100) is contacted with the anti-human PD-L1 antibody (101) under conditions that permit specific binding of the antibody. The antibody is then contacted with a secondary antibody (102) specific for the anti-PD-L1 antibody that is modified with several non-endogenous haptens (103). The sample is then contacted with an anti-hapten antibody (104) that is conjugated to an enzyme capable of catalyzing a reaction depositing a chromogen (105).

Labeled tumor samples are then visualized microscopically and assayed for PD-L1 staining. The tumor sample is then scored based on the percentage of total tumor cells that contain any amount of detectable anti-PD-L1 membrane staining above background are counted. Preferably, the scoring does not include analysis of PD-L1 expression in non-tumor cells. A tumor having a percentage of tumor cells that contain detectable anti-PD-L1 membrane staining that falls above a predefined cutoff are classified as "PD-L1-positive." The cutoff is preferably determined empirically by evaluating patient responses to a PD-1 axis directed therapeutic. PD-1 axis directed therapeutics include agents that disrupt binding of PD-1 ligands (such as PD-L1 and PD-L2) to PD-1. For example, a PD-1 axis directed therapeutic includes: anti-PD-1 monoclonal antibodies (such as OPDIVO (nivolumab), KEYTRUDA (pembrolizumab), Pidilizumab (CT-011, Cure Tech), BMS 936559 (Bristol Myers Squibb), and MPDL328OA (Roche)); and anti-PD-L1 monoclonal antibodies (such as MEDI4736, MPDL3280 and avelumab). In one specific example, the cutoff is set at 25%, wherein tumors having 25% or more tumor cells that contain any amount of detectable anti-PD-L1 membrane staining are considered to be PD-L1-positive tumors.

Patients having PD-L1-positive tumors as determined in this manner may be candidates for treatment with a therapeutic agent that disrupts binding of PD-L1 to PD-1 and/or CD80. Exemplary therapeutic agents include antibodies or antibody fragments that bind to the extracellular domain of PD-L1, thereby preventing PD-L1 from binding to PD-1 and/or CD80. Many such antibodies are currently being tested clinically. One such example is termed MEDI4736, which is currently the subject of numerous clinical trials.

EXAMPLES

I. Staining Process

A high quality companion diagnostic to predict which patients are more likely to respond to PD-1/PD-L1 antibody-based therapy is needed to ensure successful treatment. Here we describe a PD-L1 immunohistochemical (IHC) diagnostic test developed by Ventana Medical Systems.

IA. Principle of the Process

VENTANA PD-L1 (SP263) is a rabbit monoclonal primary antibody which binds to PD-L1 in paraffin-embedded tissue sections. The specific antibody can be localized using a haptenated secondary antibody followed by a multimer anti-hapten-HRP conjugate (OptiView DAB IHC Detection Kit, Cat. No. 760-700). The specific antibody-enzyme complex is then visualized with a precipitating enzyme reaction product. Each step is incubated for a precise time and temperature. At the end of each incubation step, the VENTANA BENCHMARK automated slide stainer washes the sections to stop the reaction and to remove unbound material that would hinder the desired reaction in subsequent steps. It also applies LCS (Cat. No. 650-210/Cat. No. 650-010), which minimizes evaporation of the aqueous reagents from the specimen slide. In addition to staining with VENTANA PD-L1 (SP263), a second slide is stained with a rabbit monoclonal negative control Ig (Cat. No. 790-4795) to assess background staining.

IB. Specimen Preparation

Routinely processed, formalin-fixed, paraffin-embedded tissues are suitable for use with this primary antibody when used with the VENTANA OptiView DAB IHC detection kit and VENTANA BenchMark ULTRA, BenchMark XT and BenchMark GX automated slide stainers. The recommended tissue fixative is 10% neutral buffered formalin (NBF) for a period of at least 6 hours up to 48 hours. Acceptable fixatives for use with VENTANA PDL1 (SP263) are Zinc Formalin and Z-5 fixatives when used with at least 6 hours of fixation time. Other fixatives, including 95% alcohol, AFA and PREFER, are unacceptable for use with the VENTANA PD-L1 (SP263). The amount used is 15 to 20 times the volume of tissue. A 3 mm or smaller section of tissue should be fixed no less than 4 hours and no more than 8 hours. Fixation can be performed at room temperature (15-25° C.).

Slides should be stained immediately, as antigenicity of cut tissue sections may diminish over time. However, cold ischemia testing of the SP263 antibody using a xenograph tissue model did not establish any conditions from hour zero to hour 24 that were not favorable with the assay.

IC. Staining Procedure

An exemplary assay using VENTANA PD-L1 (SP263) Rabbit Monoclonal Antibody was developed for use on VENTANA BENCHMARK XT, BENCHMARK GX AND BENCHMARK ULTRA automated slide stainers in combination with VENTANA detection kits and accessories. Table 2 illustrates an exemplary staining protocol for use on BENCHMARK stainers:

TABLE 2

| Procedure Type | Method |
| --- | --- |
| Deparaffinization | Selected |
| Cell Conditioning (Antigen Unmasking) | CELL CONDITIONING 1, 64 minutes, Standard |
| Pre-primary peroxidase Inhibitor | Selected |
| Antibody (Primary) | BENCHMARK GX or XT instrument: 16 minutes, 37° C. BENCHMARK ULTRA instrument: 16 minutes, 37° C. |
| OPTIVIEW HQ Linker | 8 min (default) |
| OPTIVIEW HRP Multimer | 8 min (default) |
| Counterstain | Hematoxylin II, 4 to 8 minutes |
| Post Counterstain | Bluing, 4 minutes |

Due to variation in tissue fixation and processing, as well as general lab instrument and environmental conditions, it may be necessary to increase or decrease the primary antibody incubation, cell conditioning or protease pretreatment based on individual specimens, detection used, and reader preference.

II. Scoring Squamous Cell Carcinoma of the Head and Neck

Figure 2:
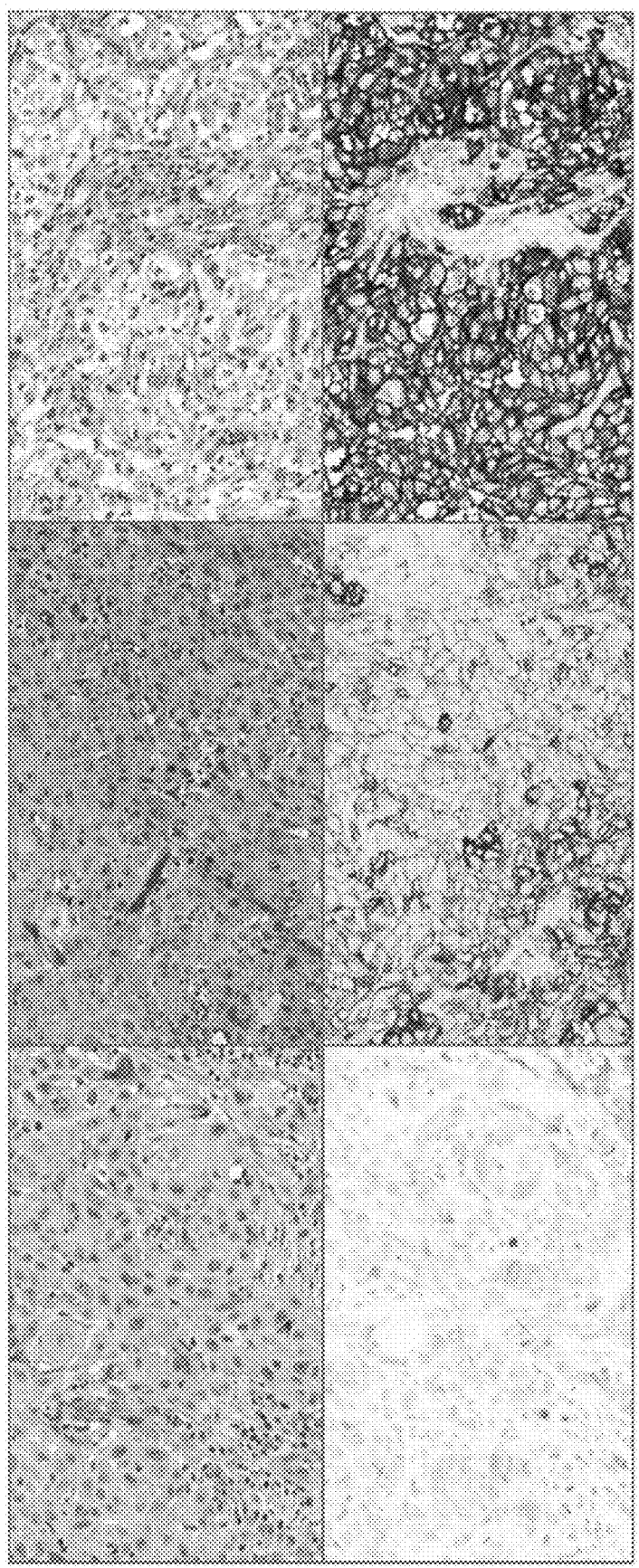
FIG. 2 illustrates various cases demonstrating the range of membrane and cytoplasmic staining in SCCHN samples at 20× magnification when labeled SP263.

SCCHN neoplastic cells labeled with the SP263 antibody are evaluated for percent positivity of the tumor cells with membrane staining at any intensity of the diaminobenzidine (DAB) signal. The immunohistochemical staining in SCCHN is membranous and/or cytoplasmic, and may be expressed homogeneously or heterogeneously throughout the neoplasm. Membrane staining can have a discontinuous or circumferential pattern. Cytoplasmic staining is generally diffuse with some cases displaying a finely granular quality. FIG. 2 illustrates various cases demonstrating the range of membrane and cytoplasmic staining in tumor cells at 20× magnification when labeled as set forth above.

Figure 3:
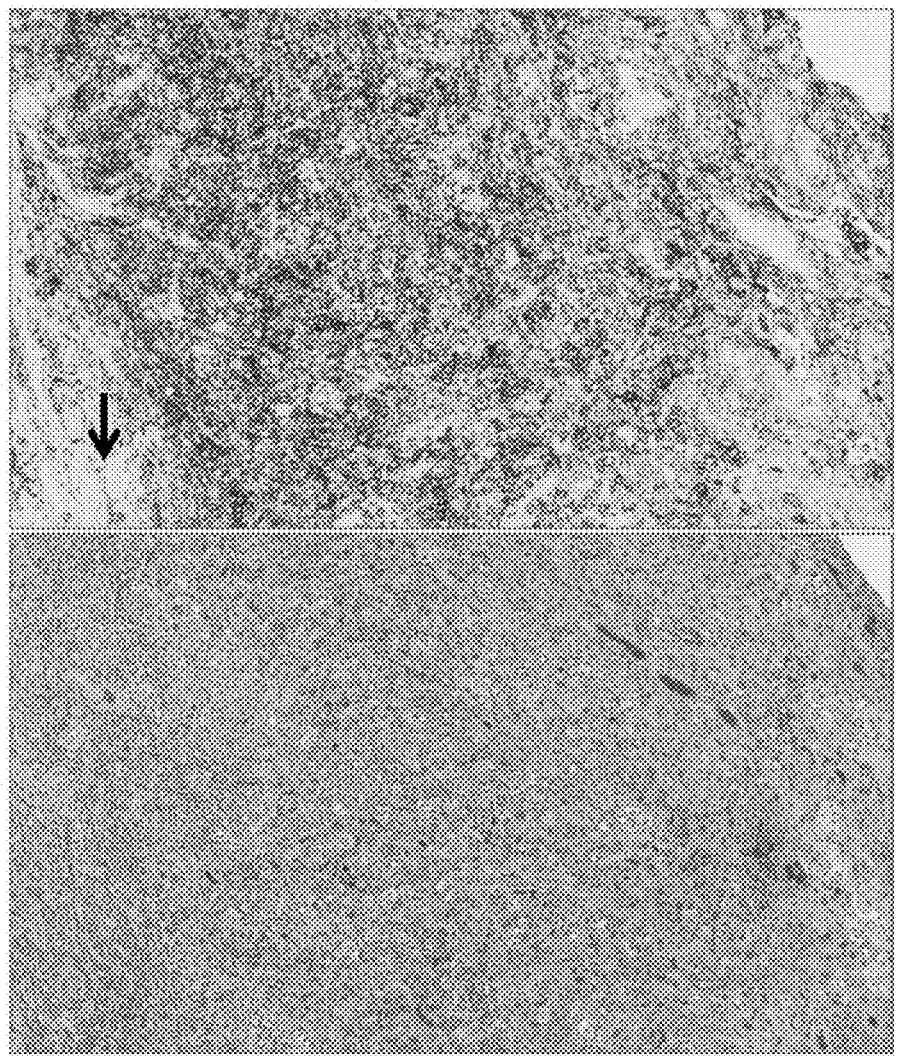
FIG. 3 illustrates an exemplary PD-L1 positive SCCHN sample labeled with SP263 with range of tumor cell membrane and cytoplasm staining The image at the top is a sample labeled with SP263 and stained with DAB. The image at the bottom is an H&E-labeled sample. The lower left corner also shows smaller immune cells with membrane staining (arrow).

The total percentage of membrane signal intensities is visually estimated and used to generate the percent tumor positive score. An isotype-matched negative control antibody is used to evaluate the presence of background in test samples and establish a staining intensity baseline. FIG. 3 illustrates an exemplary positive case with range of tumor cell membrane and cytoplasm staining. The lower left corner also shows smaller immune cells with membrane staining (arrow).

IIA. Internal Positive Controls

Figure 4:
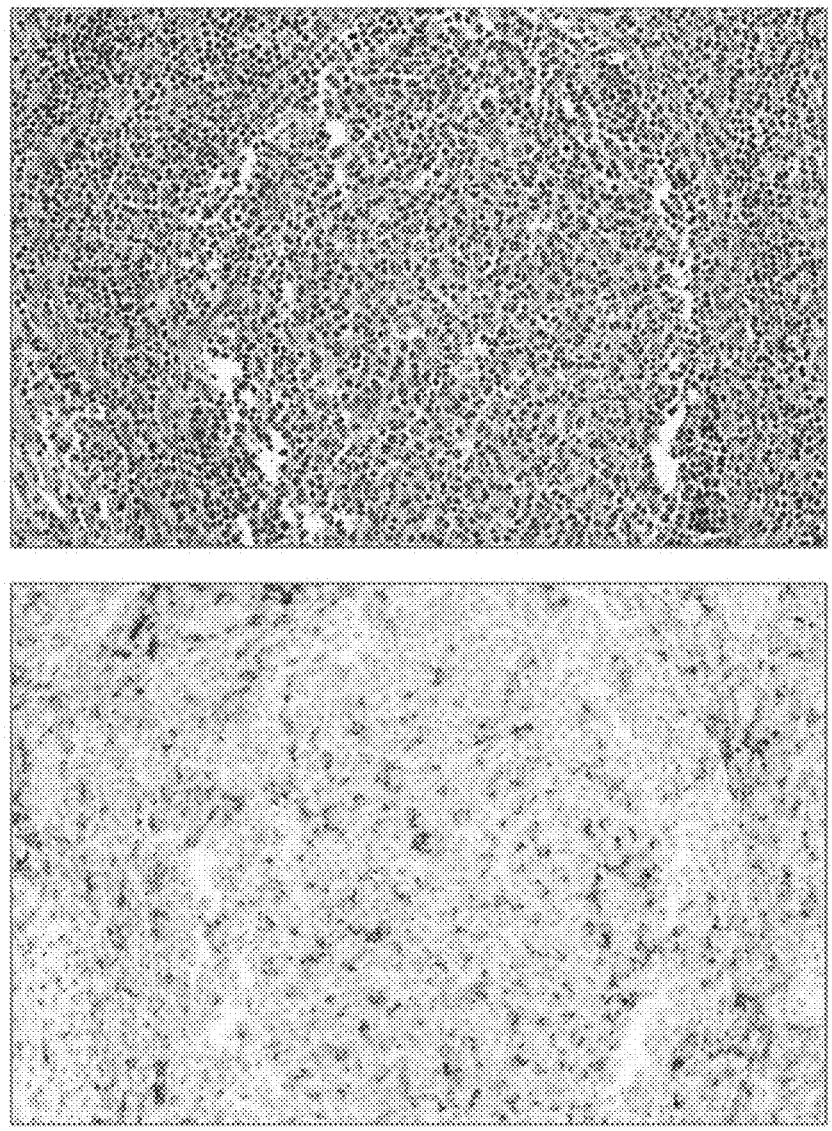
FIGS. 4-6 illustrate use of immune cells as an internal positive control in SCCHN. Top images are H&E labelled samples. Bottom images are SCCHN samples labeled with SP263 and stained with DAB.
Figure 5:
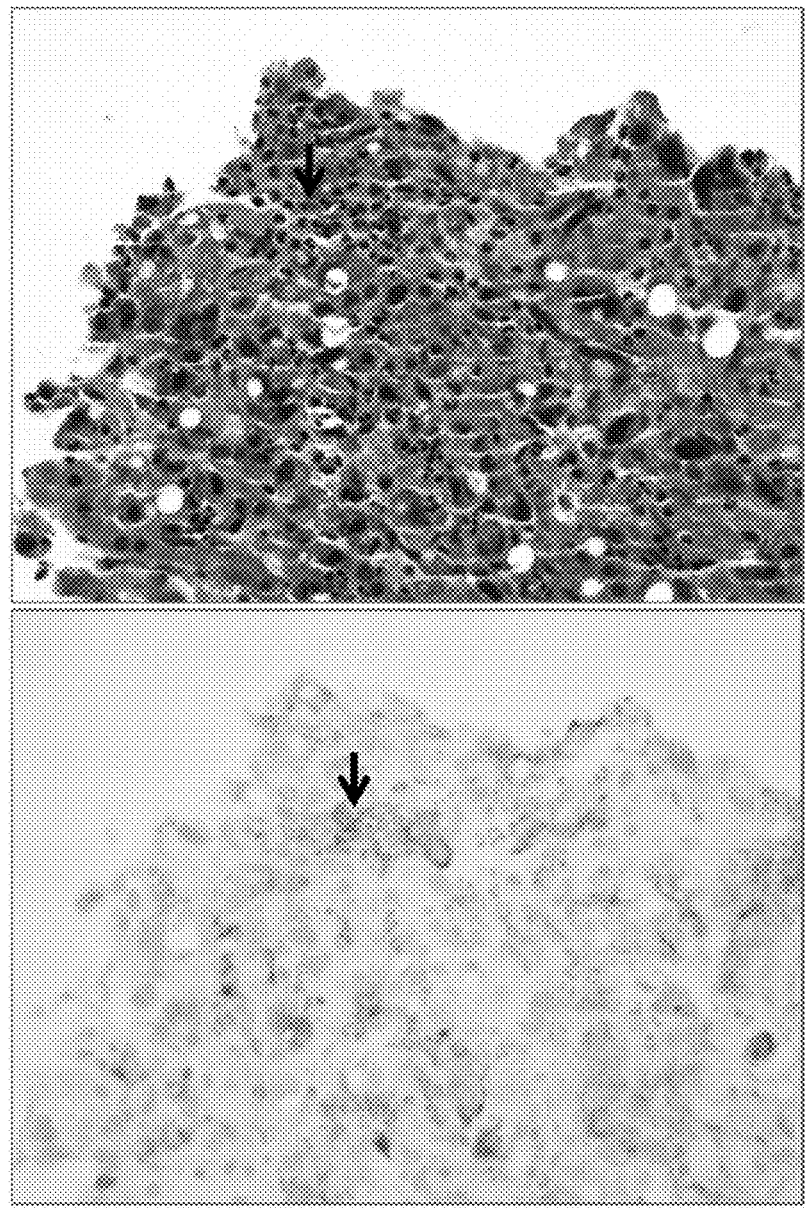
Figure 6:
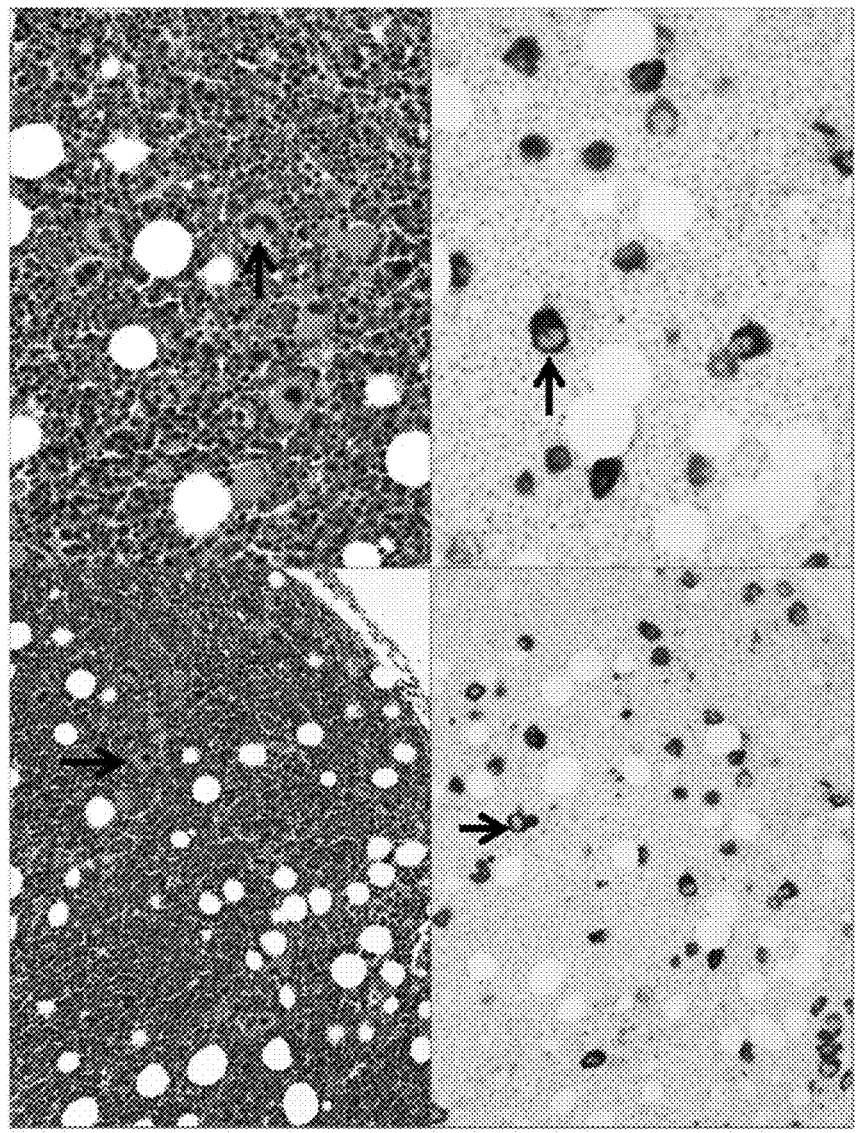

Immune cells may serve as positive internal controls, and exhibit a range of staining intensity: negative, weak diffuse cytoplasmic and/or weak to strong membranous signal. A punctate pattern of staining may be seen in association with lymphocytes. PD-L1 expression has been observed in lymphocytes, macrophages, plasma cells, and neutrophils. Representative images of immune cells stained with the SP263 antibody are provided at FIGS. 4-6 as a reference.

IIB. Tissue Requirements

This exemplary assay used at least one serial tissue section for each of: (1) hematoxylin and eosin (H&E) staining; (2) negative control antibody staining; and (3) staining with the SP263 antibody. In addition normal human term placenta tissue can be used as a control for the PD-L1 (SP263) assay. This tissue shows moderate to strong uniform staining of the membrane and cytoplasm of trophoblast-lineage cells. Placental stromal tissue and vasculature can be used for assessment of any background staining. If H&E evaluation indicates that the patient specimen is inadequate then a new specimen should be obtained. Repeat staining of a specimen should be carried out on unstained slides if (1) the tissue run control slide does not exhibit acceptable staining; (2) the negative control case slide does not exhibit acceptable staining; or (3) the SP263 antibody stained case slide (the PD-L1 IHC slide) is not evaluable. If the last of these slides is not interpretable due to artifacts, edge effects, necrosis, lack of tissue, or any other reason, then the slide cannot be used for clinical evaluation. If controls are acceptable and the SP263 antibody stained slide is evaluable, the slide can be evaluated by a trained pathologist as described in the Scoring Criteria.

IIC. Positive Tissue Control

Figure 7:
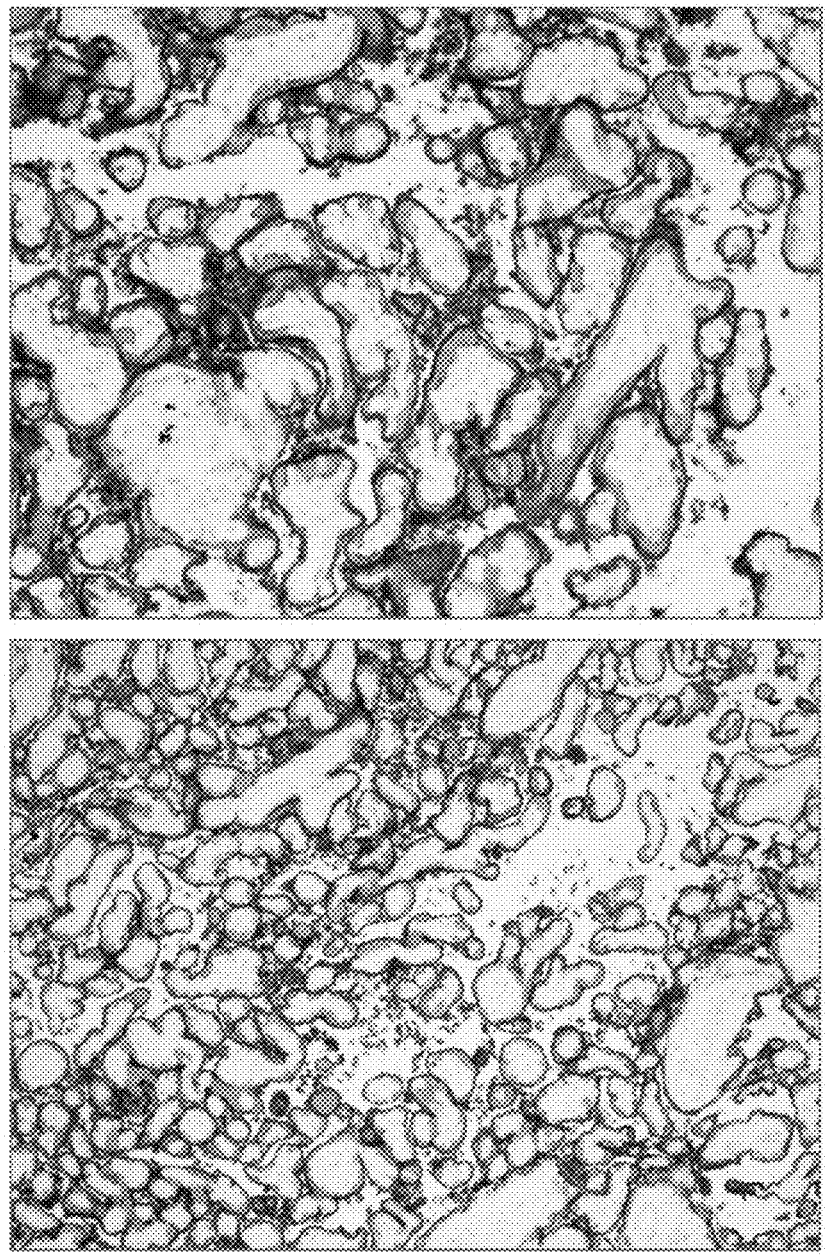
FIGS. 7A and 7B are placental tissue labeled with the SP263 antibody and stained with DAB.

A known positive control tissue fixed and processed in the same manner as the patient specimens should be run for each set of test conditions and with every SP263 antibody staining procedure performed. The control tissue (an index case) should be a fresh autopsy, biopsy, surgical specimen prepared and fixed as soon as possible in a manner identical to patient specimens. This tissue may be used to monitor all steps of specimen processing and staining. A tissue section fixed or processed differently from the test specimen can be used as a control for reagents and staining but not for fixation or tissue preparation. A positive SCCHN case with moderate staining is more suitable for quality control than one that stains strongly; it can be used to detect minor levels of reagent degradation or out-of-specification issues that might be instrument-related. Positive membrane staining of neoplastic cells in the control tissue confirms antibody was applied and the instrument functioned properly. The positive tissue control should be used only to monitor performance; it should not be used to aid the clinical diagnosis of patient samples. Additionally, the assay illustrated herein can utilize as a positive control human term placental tissue, which shows moderate to strong uniform staining of the membrane and cytoplasm of trophoblast-lineage cells. Placental stromal tissue and vasculature can be used for assessment of any background staining. Exemplary images of placental tissue stained with the SP263 antibody are at FIGS. 7A and 7B.

IID. Scoring Criteria

A PD-L1 IHC Clinical Status is assigned by a trained pathologist based on his or her evaluation of the percentage of specific PD-L1 IHC staining A cutoff for positivity and negativity is selected based on clinical data from known responders to the PD-1 axis therapeutic being used. In this exemplary embodiment, a 25% cutoff was selected. A clinical status of negative is assigned to cases with a total percent of tumor cells with membrane staining at any intensity of less than 25%. A clinical status of positive is assigned to cases with total percent of tumor cells with membrane staining at any intensity of greater than or equal to 25%. Clinical interpretation of SCCHN cases stained with the SP263 antibody was based on the criteria noted in table 3.

TABLE 3

| PD-L1 Scoring Algorithm | |
|---|---|
| Interpretation | Staining Description |
| Positive for PD-L1 | ≥25% of tumor cells with membrane positivity for PD-L1 at any intensity above background staining as noted on the corresponding negative isotype control. |
| Negative for PD-L1 | <25% of tumor cells with membrane positivity for PD-L1 at any intensity above background staining as noted on the corresponding negative isotype control. |

Images of various negative and positive staining patterns are provided in the subsequent sections.

IID(1). Negative Cases

Negative staining intensity is characterized by the absence of any detectable signal or by membranous staining of any intensity in less than 25% of neoplastic cells.

Figure 8:
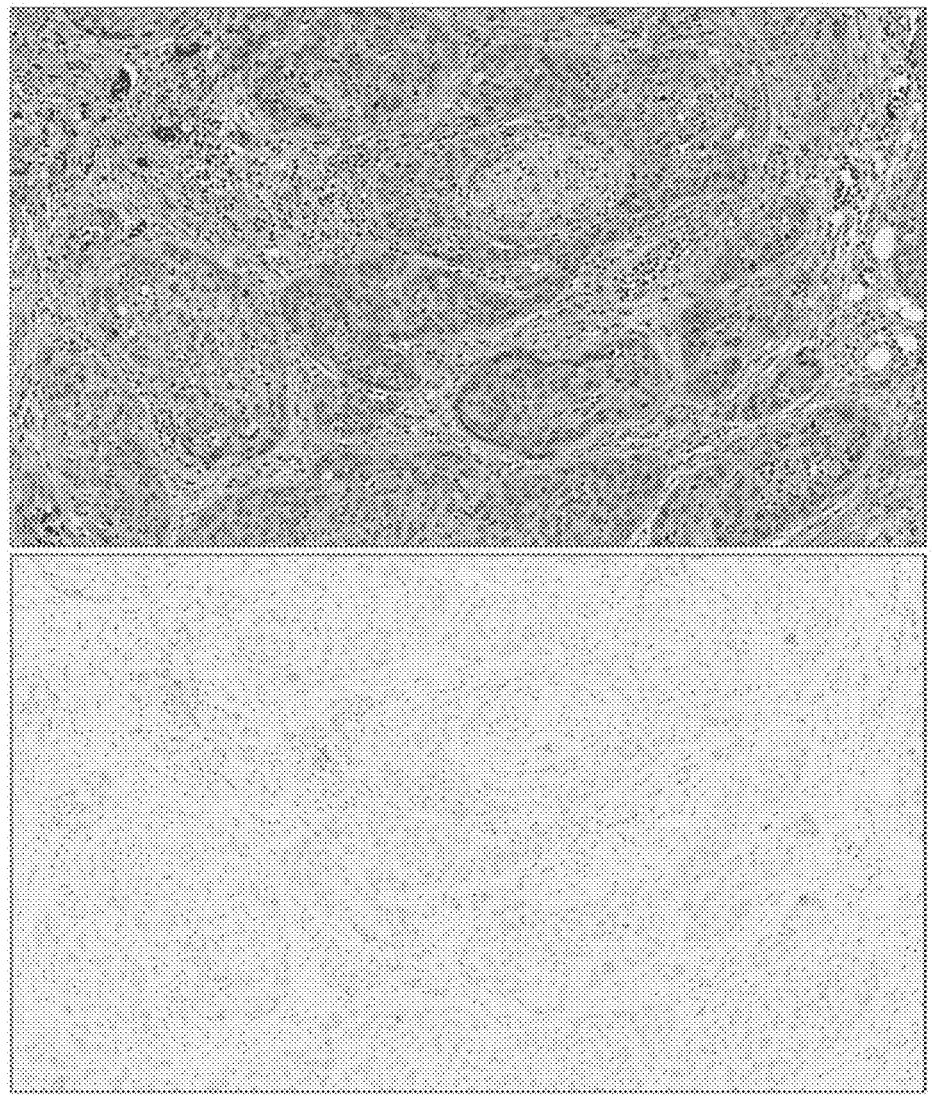
FIG. 8 is a SCCHN sample determined to be negative using SP263. Top image is H&E; bottom image is DAB.

Negative Case 1 is illustrated at FIG. 8. Zero percent of tumor and immune cells have visible membrane staining at 10× magnification, and thus this case is classified as negative.

Figure 9:
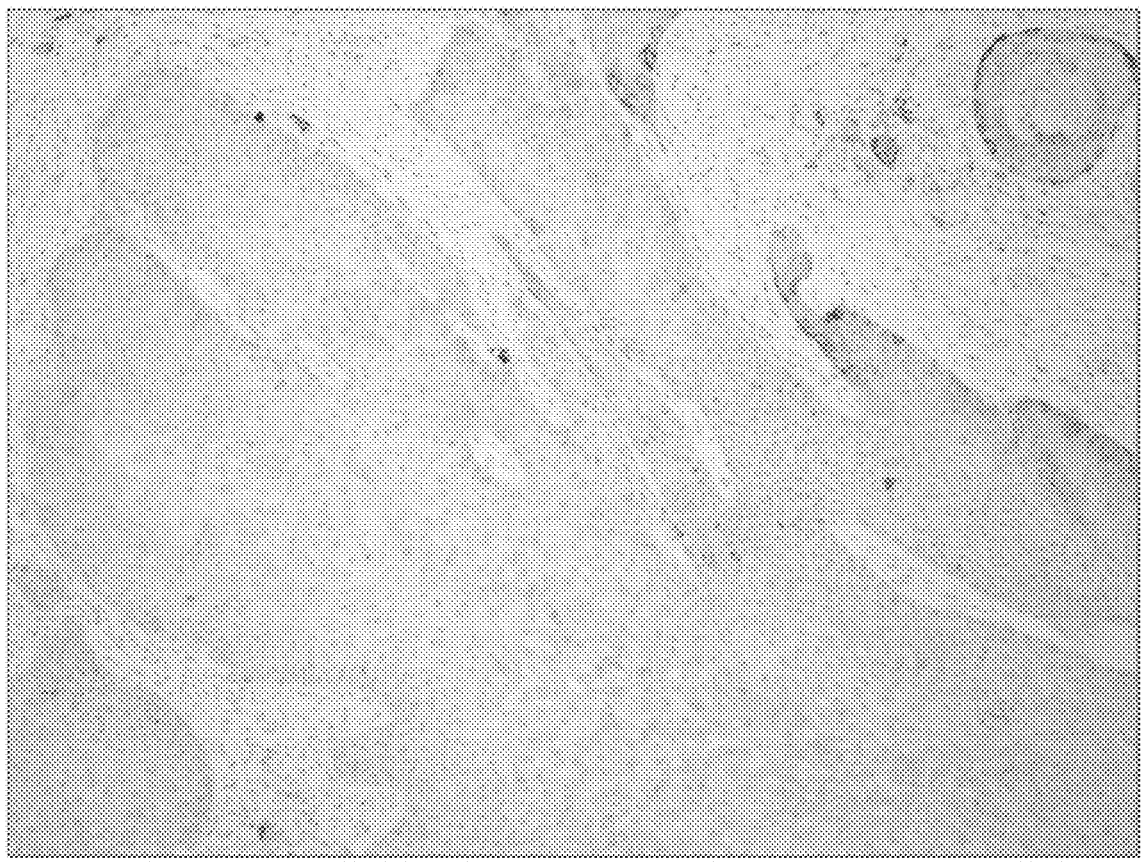
FIG. 9 is a SCCHN sample determined to be negative using SP263.

Negative Case 2 is illustrated at FIG. 9. Weak to moderate tumor cell membrane staining (raw score of 15%) and immune cell staining is observed at 10× magnification, and thus the case was classified as negative.

IID(2). Positive Cases

Positive staining intensity was characterized by the presence of membranous staining of any intensity in greater than or equal to 25% of neoplastic cells.

Figure 10:
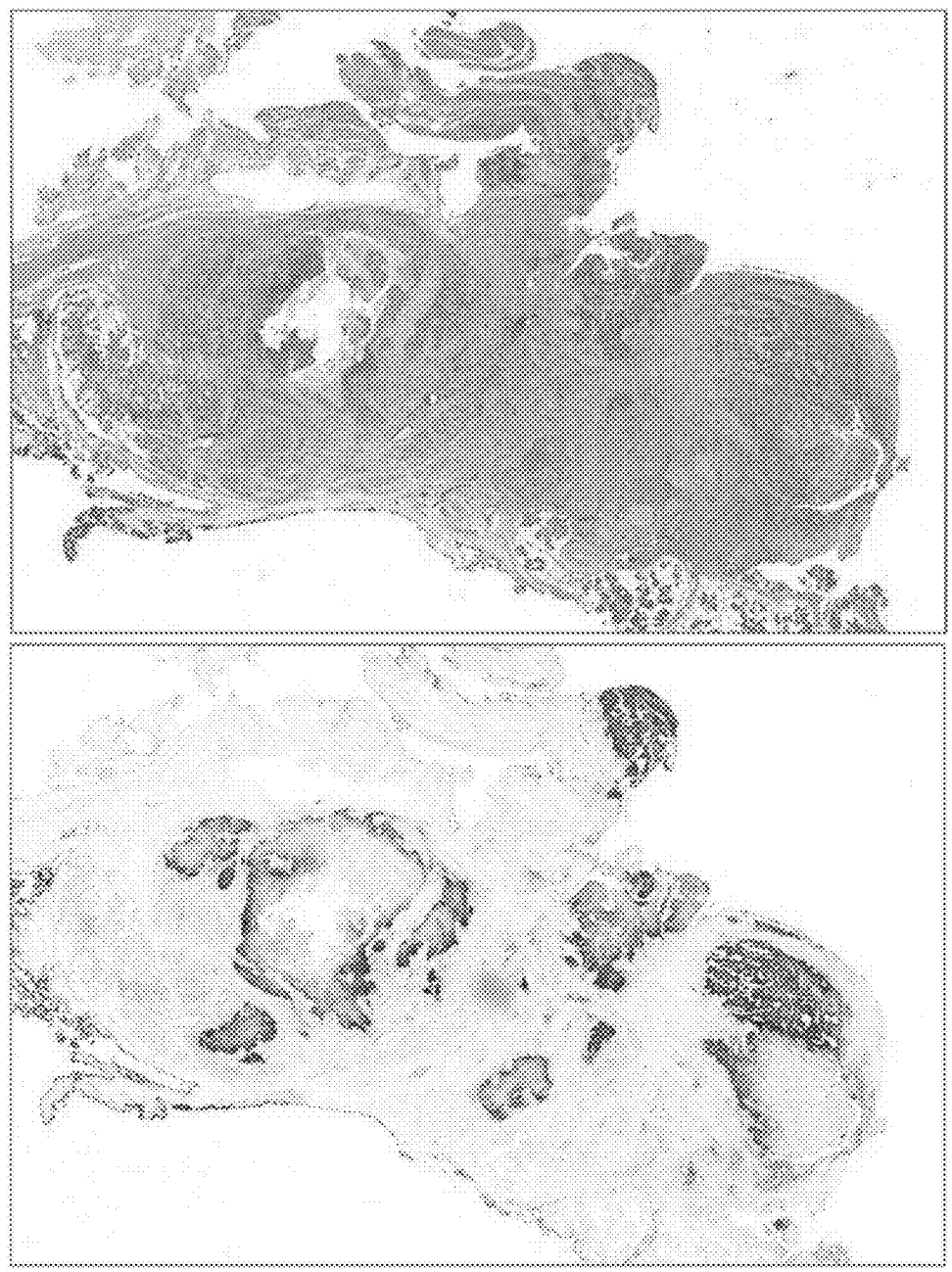
FIG. 10. is an SCCHN sample stained with SP263 having 70% of PD-L1-positive tumor cells at 1× magnification. Top image is H&E stain; bottom image is DAB stain.

Positive Case 1 is illustrated at FIG. 10. Tumor cell membrane staining is observed in at 70% of tumor cells at 1× magnification.

Figure 11:
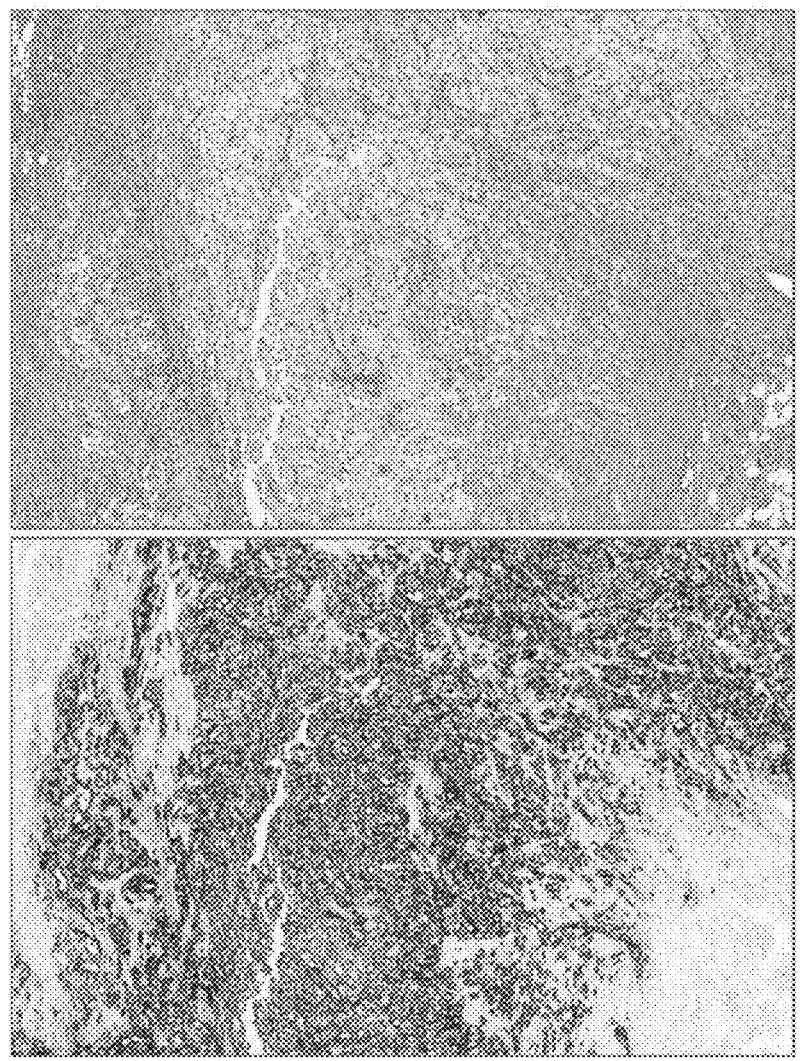
FIG. 11. is an SCCHN sample stained with SP263 having cell membrane staining in 100% of tumor cells, and is accompanied by tumor immune cell staining along periphery of tumor at 4× magnification. Top image is H&E stain; bottom image is DAB stain.

Positive Case 2 is illustrated at FIG. 11. Tumor cell membrane staining is observed in 100% of tumor cells, and is accompanied by tumor immune cell staining along periphery of tumor at 4× magnification.

IID(3). Evaluation of Immune Cell Staining

Figure 12:
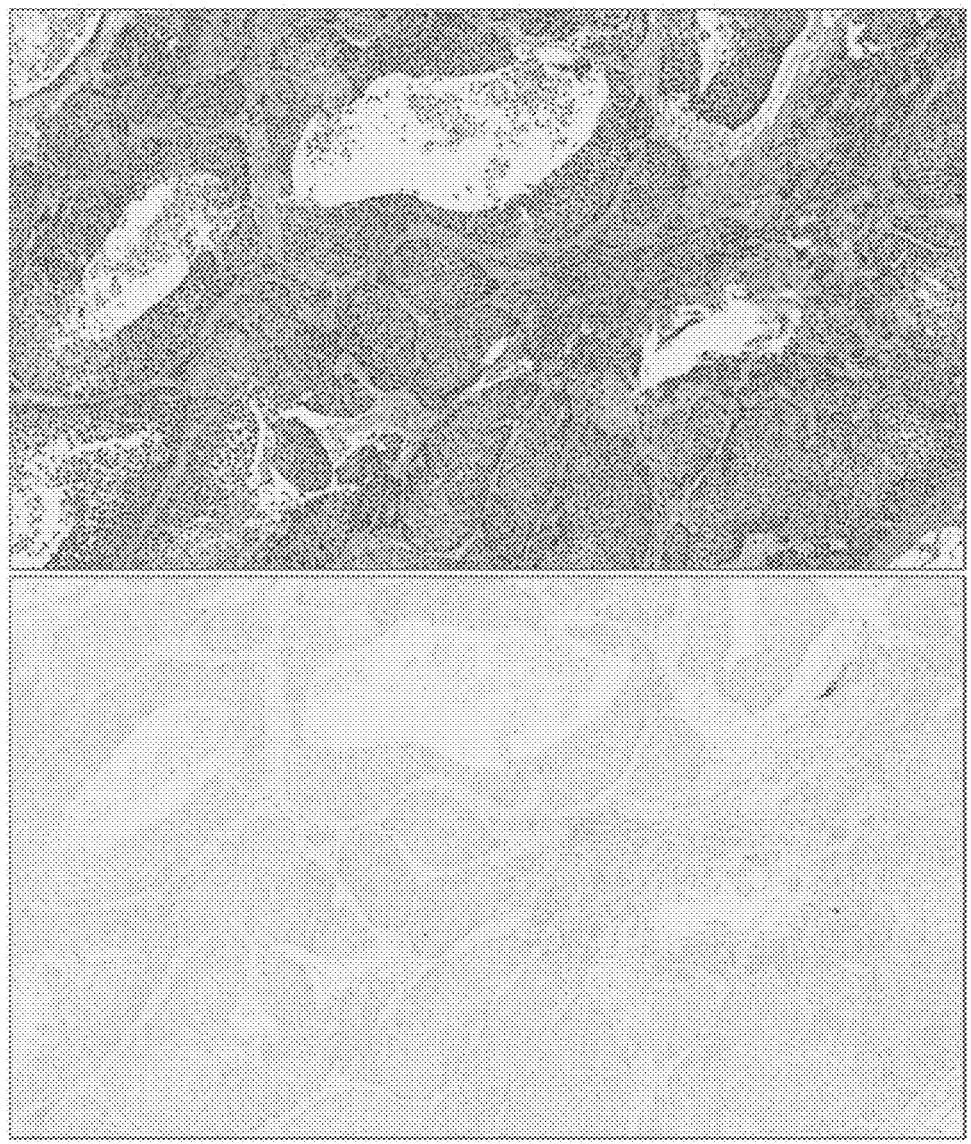
FIG. 12 is an SCCHN sample stained with SP263 having immune cell staining and no tumor staining. Total immune cells in tumor area in this image is 15% with 35% of the immune cells staining with PD-L1 expression at 5× magnification. Top image is H&E stain; bottom image is DAB stain.

Immune cell staining was captured for exploratory purposes. A variety of immune cells display staining, and include lymphocytes, macrophages, reticular dendritic cells, plasma cells and neutrophils. The H&E-stained slide was initially examined to determine the total percentage of the tumor area (tumor cells and any desmoplastic stroma) involved by immune cells. Areas not considered part of the tumor area include non-viable tumor, such as areas with cautery or crush artifacts, acellular pools of mucin, and extensive necrosis. Normal lymphoid tissue uninvolved by the neoplasm, as seen in lymph nodes with metastatic tumor, and any foreign body giant cell reaction are not evaluated as a part of the tumor area or immune cells involving the tumor. The PD-L1 IHC slide is then scored for the percentage of tumor-associated immune cells staining for PD-L1. In cases where positively-staining immune cells are intermixed with positively-staining tumor cells, it can be difficult to quantify the amount of staining for each component. Examples of immune cell interpretation are given at FIG. 12, which has immune cell staining and no tumor staining. Total immune cells in tumor area in this image is 15% with 35% of the immune cells staining with PD-L1 expression at 5× magnification.

IID(4). Challenging Cases

Cases are given a clinical status according to percentage of tumor cells with membrane staining. Various staining patterns and morphologic features may make interpretation and quantification of tumor membrane staining difficult. Some cases may be particularly challenging due to the following issues:

Weak Cytoplasmic Staining

Some specimens may exhibit weak tumor cell cytoplasmic staining of the tumor cells that may be confused at low power with weak tumor cell membrane staining. For this reason when evaluating stained slides, weak staining should be confirmed with examination at higher powers to distinguish between tumor cell membranous and cytoplasmic staining.

Strong Immune Cell Staining Overlapping with Tumor Cell Staining

Some tumors may contain an extensive inflammatory component both surrounding the tumor and infiltrating within the tumor. In instances when strong staining is seen for both tumor and immune cells it can be challenging to differentiate and quantify the assay staining between the two cell populations. The presence of immune cells infiltrating the tumor should be confirmed using the H&E slide. The pattern of PD-L1 staining is utilized to help attribute expression to immune cells (punctate staining) and tumor cells (linear membrane staining).

Obscuring Endogenous Material

Occasionally in SCCHN samples endogenous material, such as anthracotic pigment, melanin pigment or hemosiderin, may obscure and interfere with interpretation of assay staining of tumor and immune cells. Comparison of the negative isotype control slide with the PD-L1 stained slide can aid in differentiating between biomarker staining and endogenous material.

Figure 13:
FIG. 13 is an SCCHN sample stained with SP263 and DAB involving weak membrane (arrow) staining of the tumor visible at 20× magnification.
Figure 14:
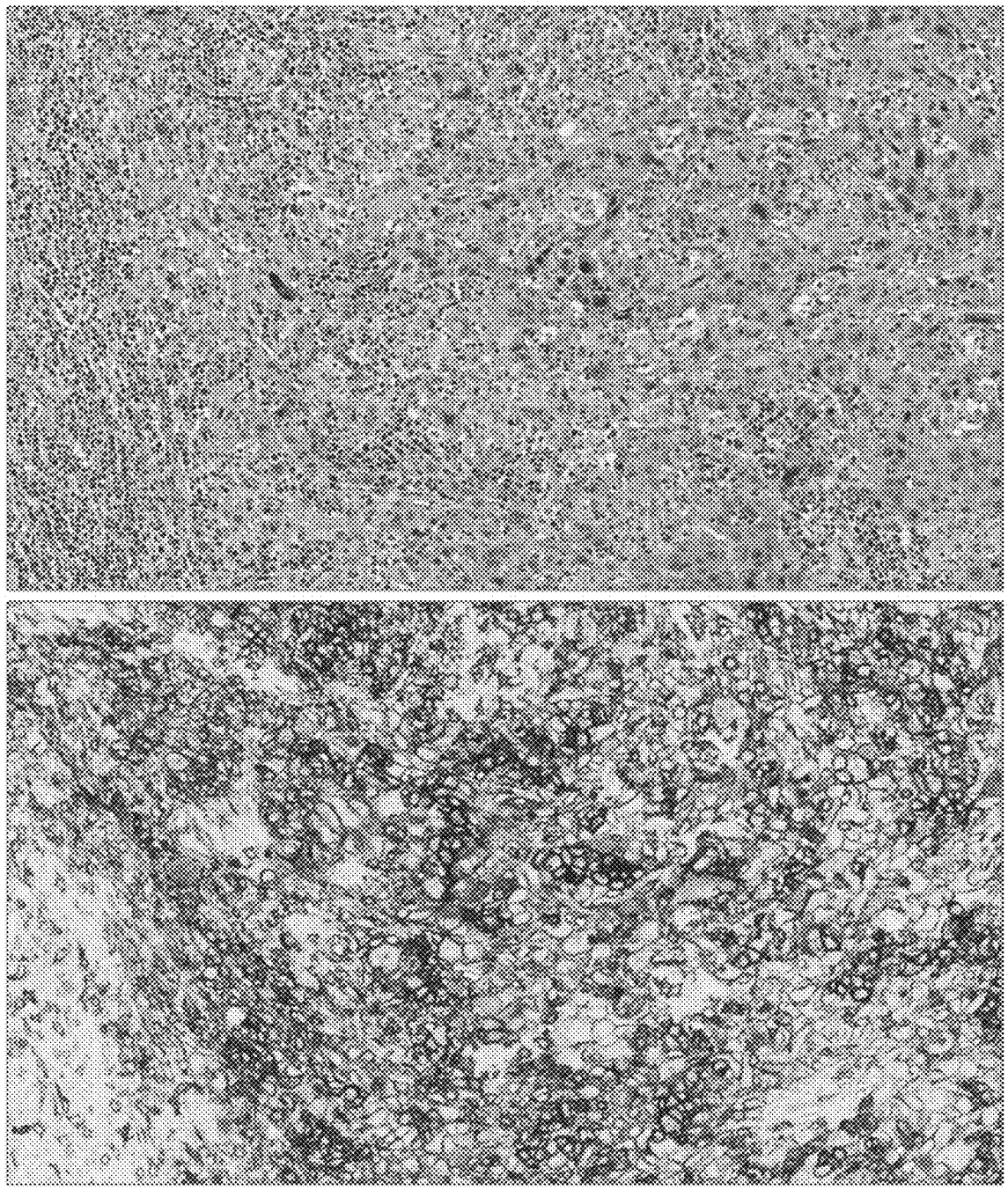
FIG. 14 is an SCCHN sample stained with SP263 involving membranous immune cell staining (lower left corner) with tumor cell membrane staining. Top image is H&E stain; bottom image is DAB stain.
Figure 15:
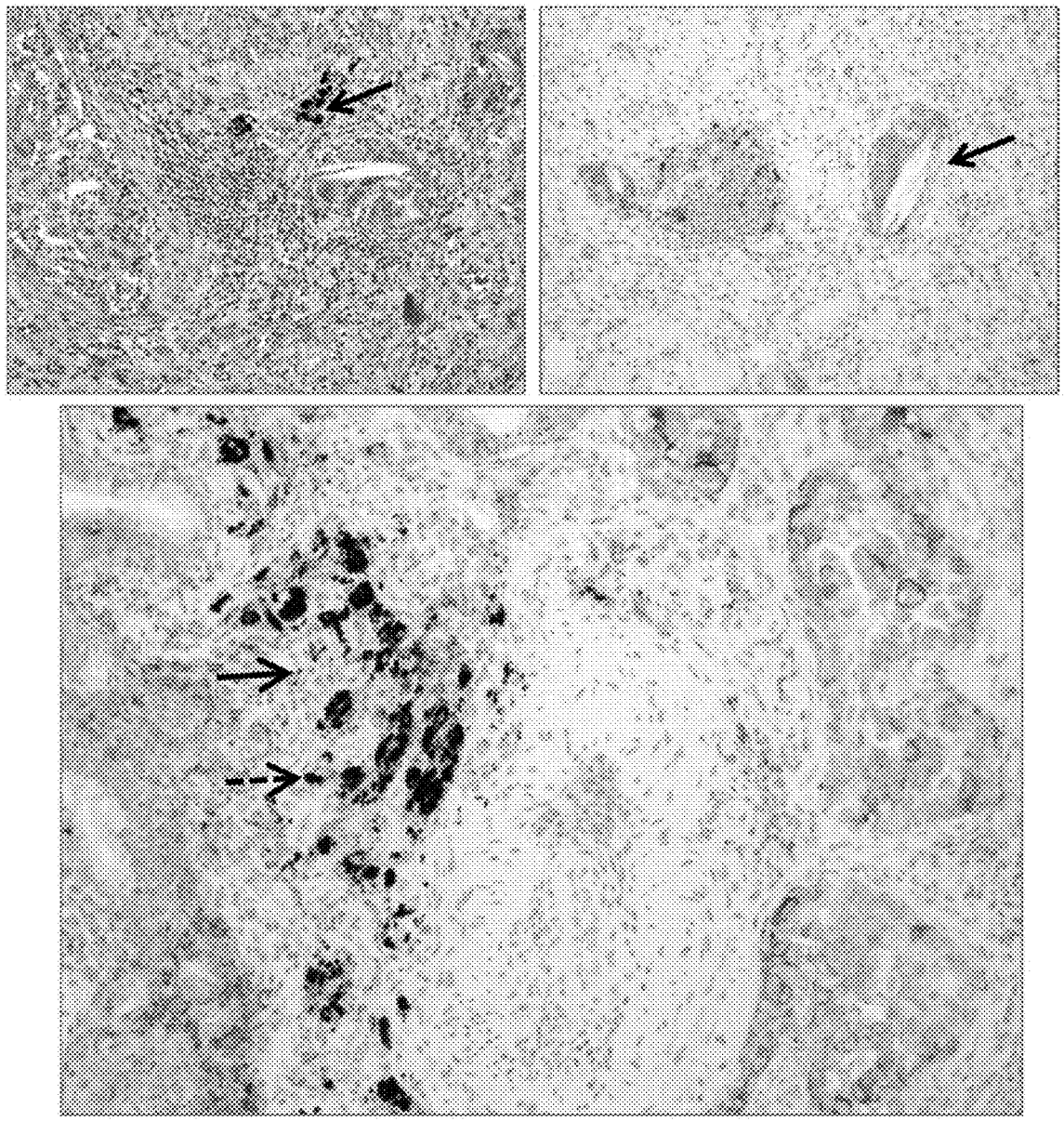
FIG. 15 is an NSCLC case showing anthracosis (black arrow in top right image) and foreign body giant cell reaction (arrow in top left image) not associated with case interpretation. A different area of the case contains anthracotic pigment (hatched arrow) overlapping with punctate immune cell staining (black arrow in bottom image arrow). All images are at 20× magnification.
Figure 16:
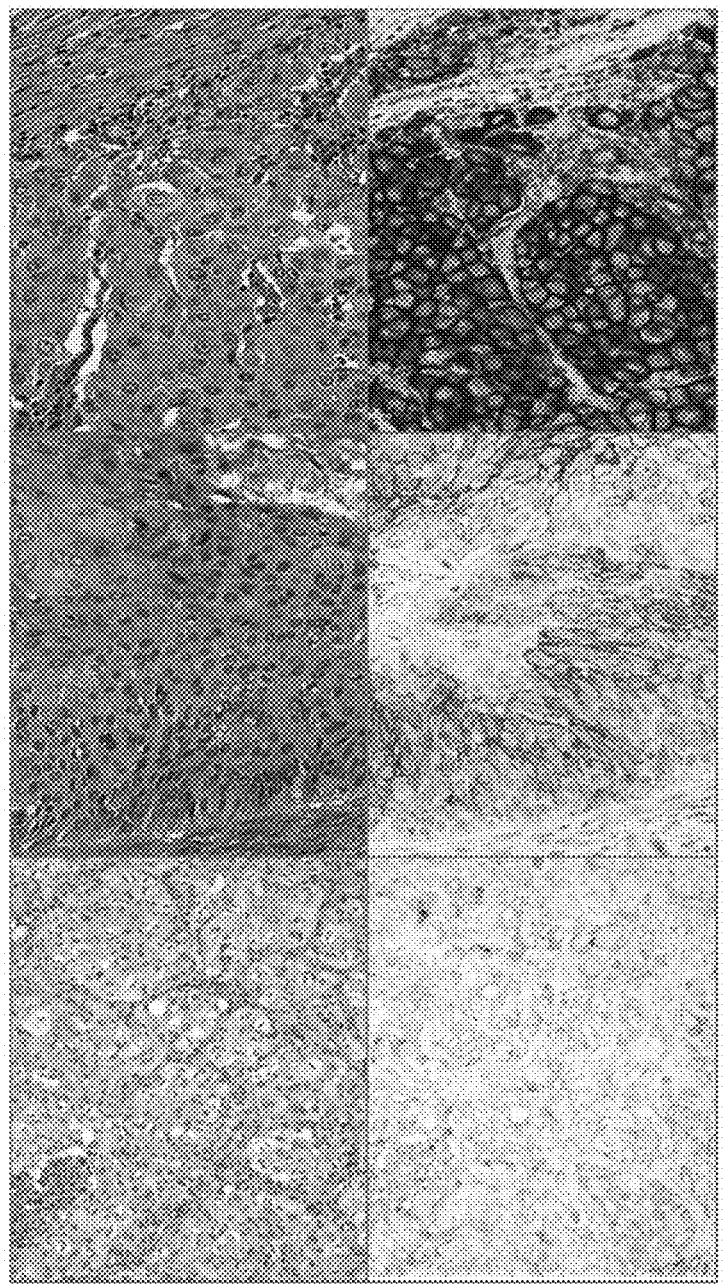
FIG. 16 illustrates various cases demonstrating the range of membrane and cytoplasmic staining in NSCLC samples at 20× magnification when labeled SP263.
Figure 17:
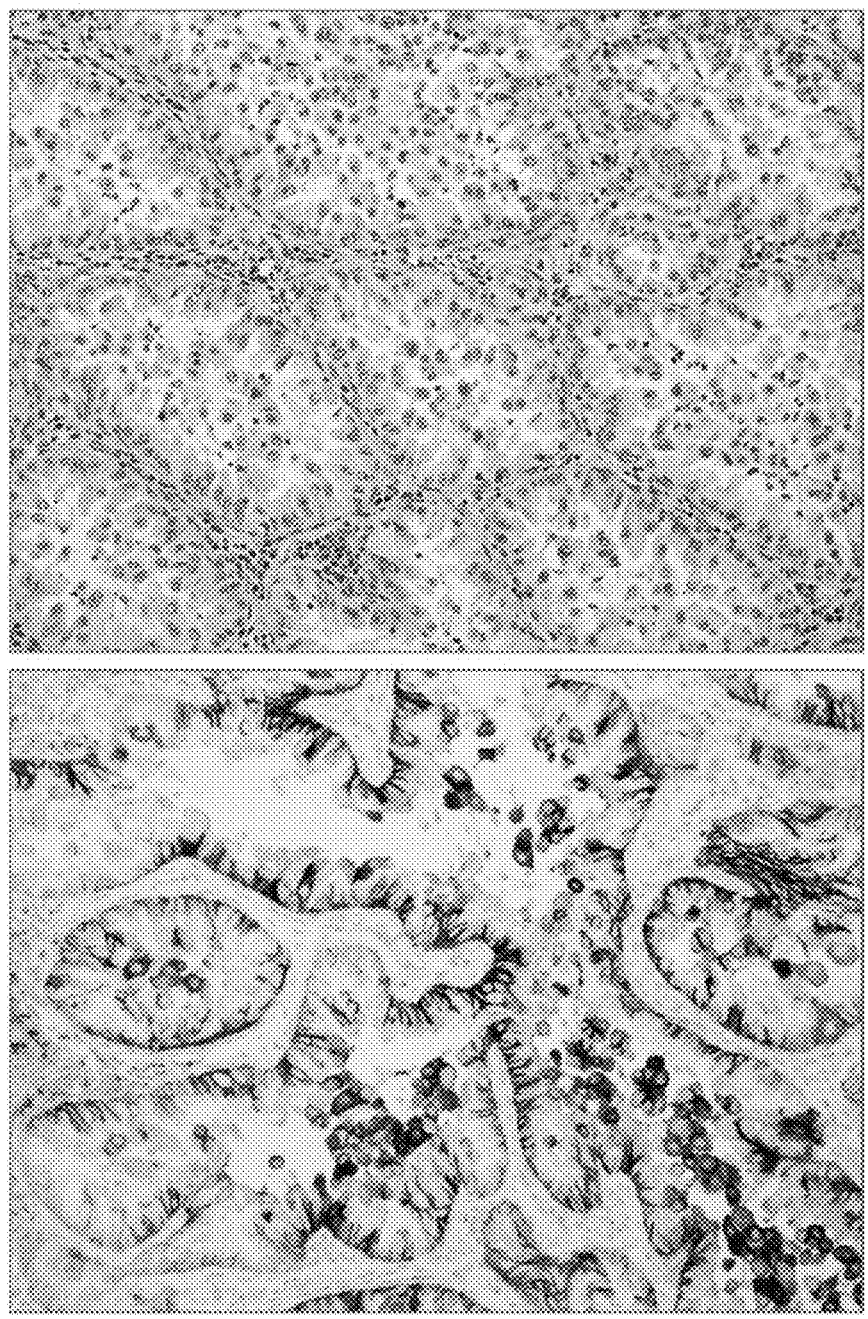
FIG. 17 is an NSCLC stained with SP263 and DAB and having tumor cells with basolateral pattern of membrane staining are illustrated at 20× magnification. Top image is H&E stain; bottom image is DAB stain.
Figure 18:
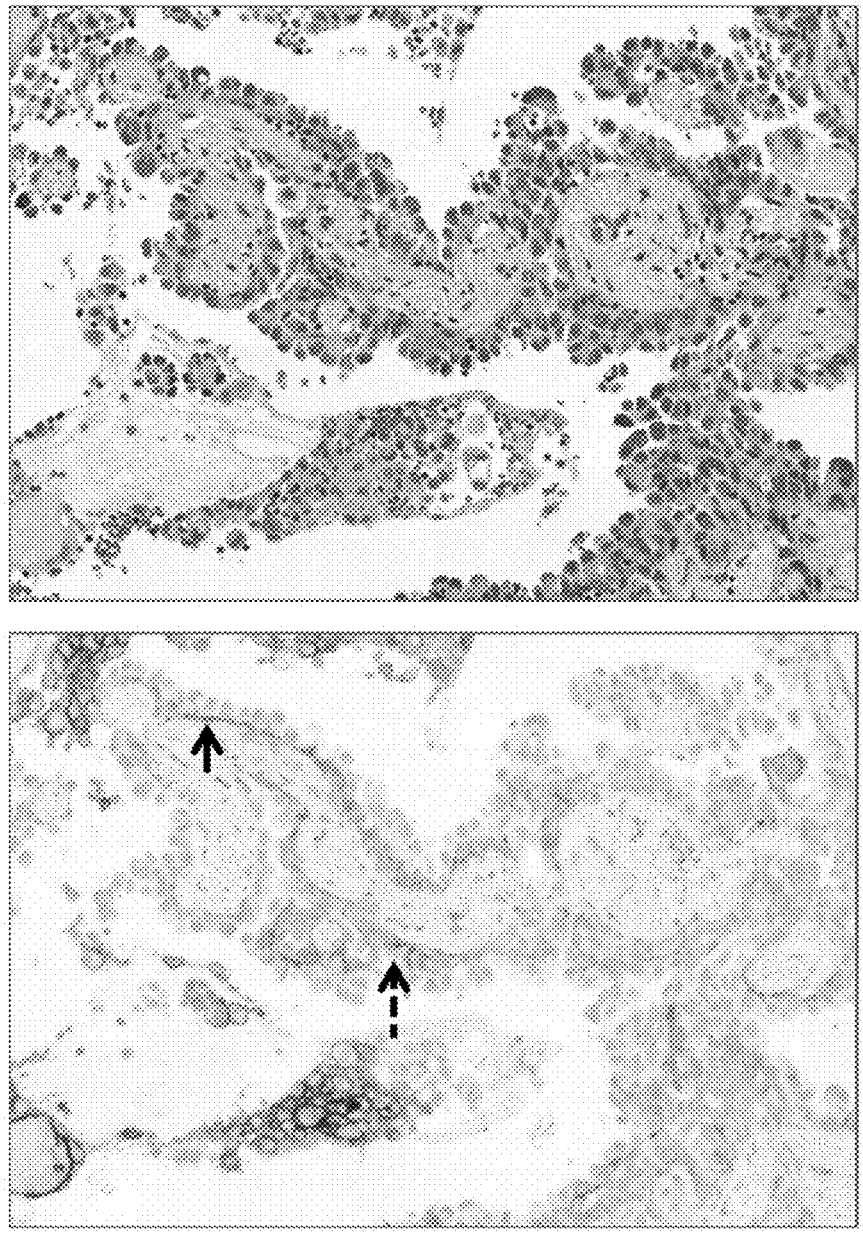
FIG. 18 is an NSCLC stained with SP263 and DAB and having tumor cells with basal-only (black arrow) staining and basolateral (hatched arrow) pattern of membrane staining are illustrated at 20× magnification. Top image is H&E stain; bottom image is DAB stain.

Some challenging cases are shown at FIGS. 13-15.

Challenging Case 1 (FIG. 13) involves weak membrane (arrow) staining of the tumor visible at 20× magnification, which can be easy to miss.

Challenging Case 2 (FIG. 14) involves membranous immune cell staining (lower left corner) with tumor cell membrane staining Note the difficulty in distinguishing the staining of intermixed immune cells from the surrounding tumor cell staining at 10× magnification.

Challenging Case 3 (FIG. 15) involves a NSCLC case showing anthracosis (black arrow in top right image) and foreign body giant cell reaction (red arrow) not associated with case interpretation. A different area of the case contains anthracotic pigment (hatched arrow) overlapping with punctate immune cell staining (black arrow in bottom image arrow). All images are at 20× magnification.

III. Scoring Non-Small Cell Lung Carcinoma

NSCLC neoplastic cells labeled with the SP263 antibody are evaluated for percent positivity of the tumor cells with membrane staining at any intensity of the diaminobenzidine (DAB) signal. The immunohistochemical staining in NSCLC is membranous and/or cytoplasmic, and may be expressed homogeneously or heterogeneously throughout the neoplasm. Membrane staining can have a discontinuous, circumferential or basolateral pattern. Cytoplasmic staining is generally diffuse with some cases displaying a finely granular quality. Rare cases have shown a peri-nuclear Golgi-like body staining with variable intensity.

Figure 19:
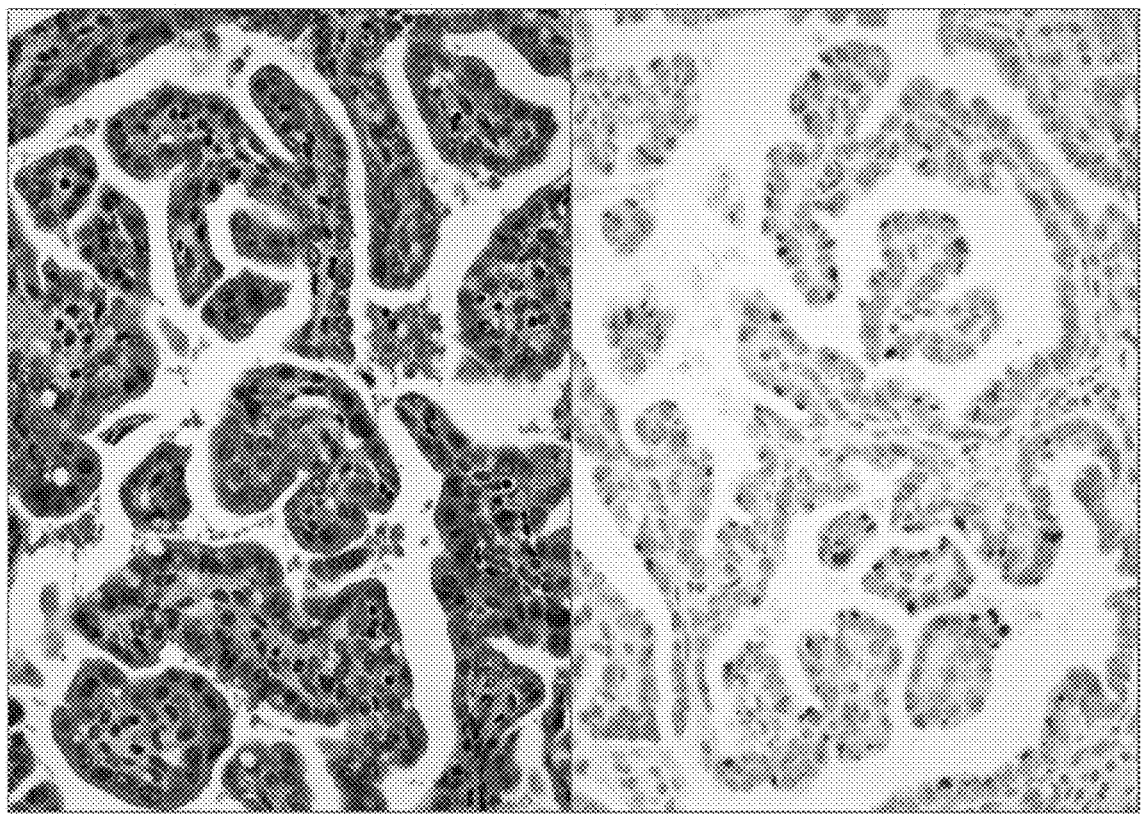
FIG. 19 is an NSCLC stained with SP263 and DAB and having peri-nuclear Golgi-like staining within tumor cells at 40× magnification. Left image is H&E stain; right image is DAB stain.

Various cases demonstrating the range of membrane and cytoplasmic staining in tumor cells are illustrated at FIG. 16-19. Tumor cells with basolateral pattern of membrane staining are illustrated at 20× magnification in FIG. 17. Tumor cells with basal-only (black arrow) staining and basolateral (hatched arrow) pattern of membrane staining are illustrated at 20× magnification at FIG. 18. FIG. 19 illustrates an unusual case with peri-nuclear Golgi-like staining within tumor cells at 40× magnification.

The total percentage of membrane signal intensities is visually estimated and used to generate the percent tumor positive score. An isotype-matched negative control antibody is used to evaluate the presence of background in test samples and establish a staining intensity baseline.

IIIA. Internal Positive Controls

Immune cells may serve as positive internal controls, and exhibit a range of staining intensity: negative, weak diffuse cytoplasmic and/or weak to strong membranous signal. A punctate pattern of staining may be seen in association with lymphocytes. PD-L1 expression has been observed in lymphocytes, macrophages, plasma cells, and neutrophils. Representative images of immune cells stained with the SP263 antibody are provided at FIG. 20-24.

Figure 20:
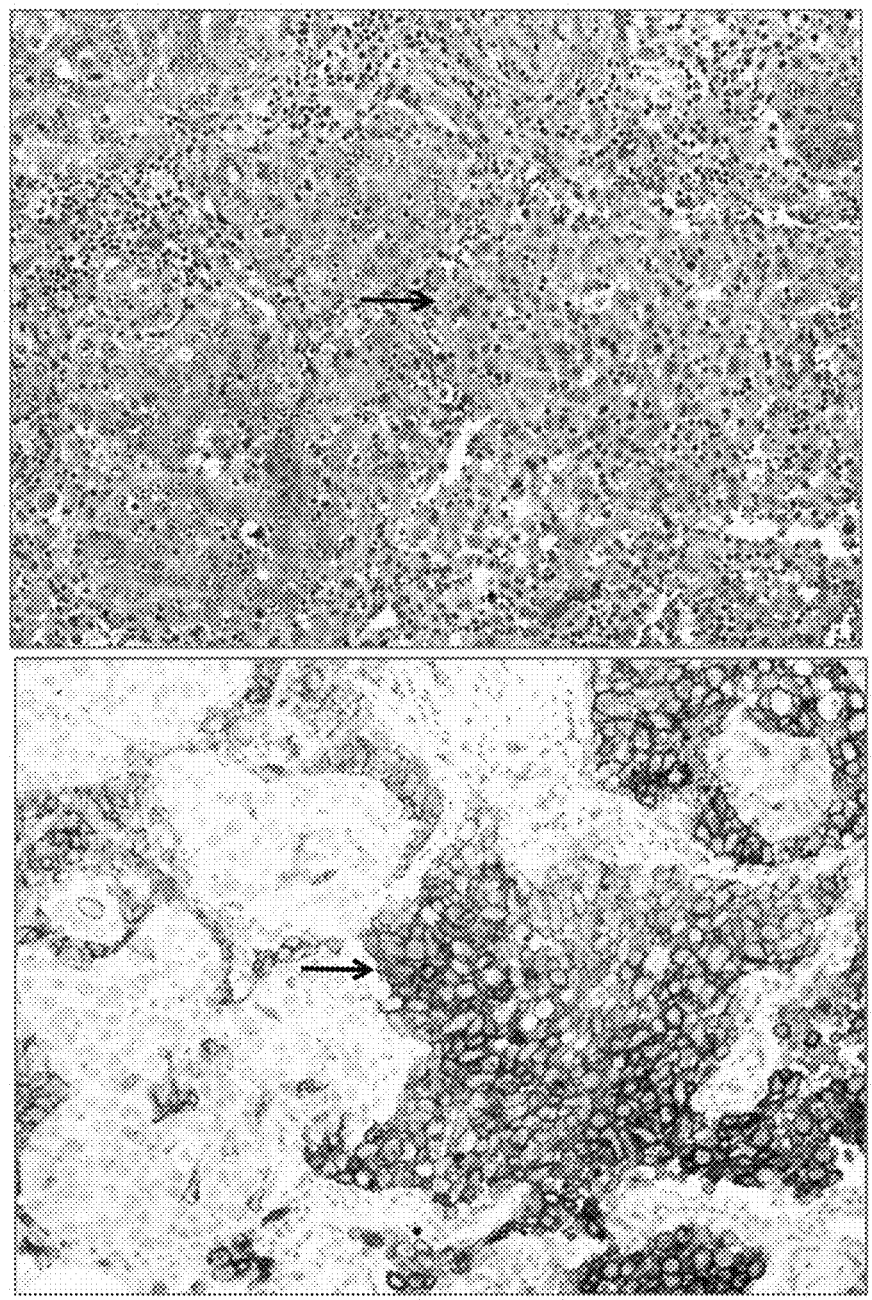
FIG. 20 is an NSCLC stained with SP263 and DAB and having tumor cells with alveolar macrophages (arrow) at 20× magnification. Top image is H&E stain; bottom image is DAB stain.

FIG. 20 illustrates tumor cells with alveolar macrophages (arrow) at 20× magnification. Positive alveolar macrophage staining can be seen in the DAB-stained image (arrow in the bottom image) with adjacent PD-L1 negative tumor (zero percent staining at 20× magnification).

Figure 21:
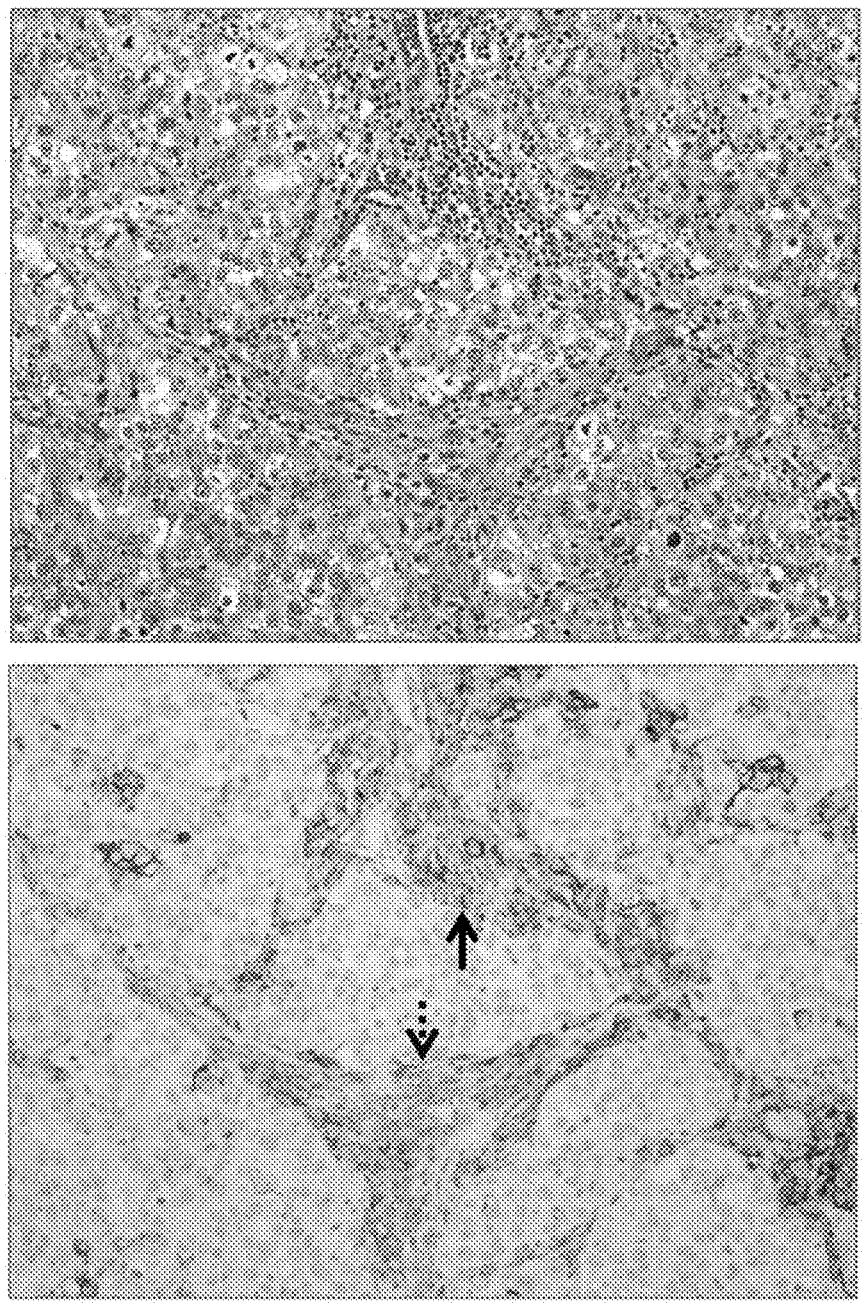
FIG. 21 is an NSCLC stained with SP263 and DAB showing tumor cells with lymphocytic and plasma cells immune cells at 20× magnification. Top image is H&E stain; bottom image is DAB stain. Punctate (solid arrow) and diffuse (hatched arrow) immune cell staining with adjacent PD-L1 negative tumor (zero percent staining at 20× magnification) can be seen in the DAB-stained image.

The H&E images in FIG. 21 shows tumor cells with lymphocytic and plasma cells immune cells at 20× magnification. Punctate (solid arrow) and diffuse (hatched arrow) immune cell staining with adjacent PD-L1 negative tumor (zero percent staining at 20× magnification) can be seen in the DAB-stained image.

Figure 22:
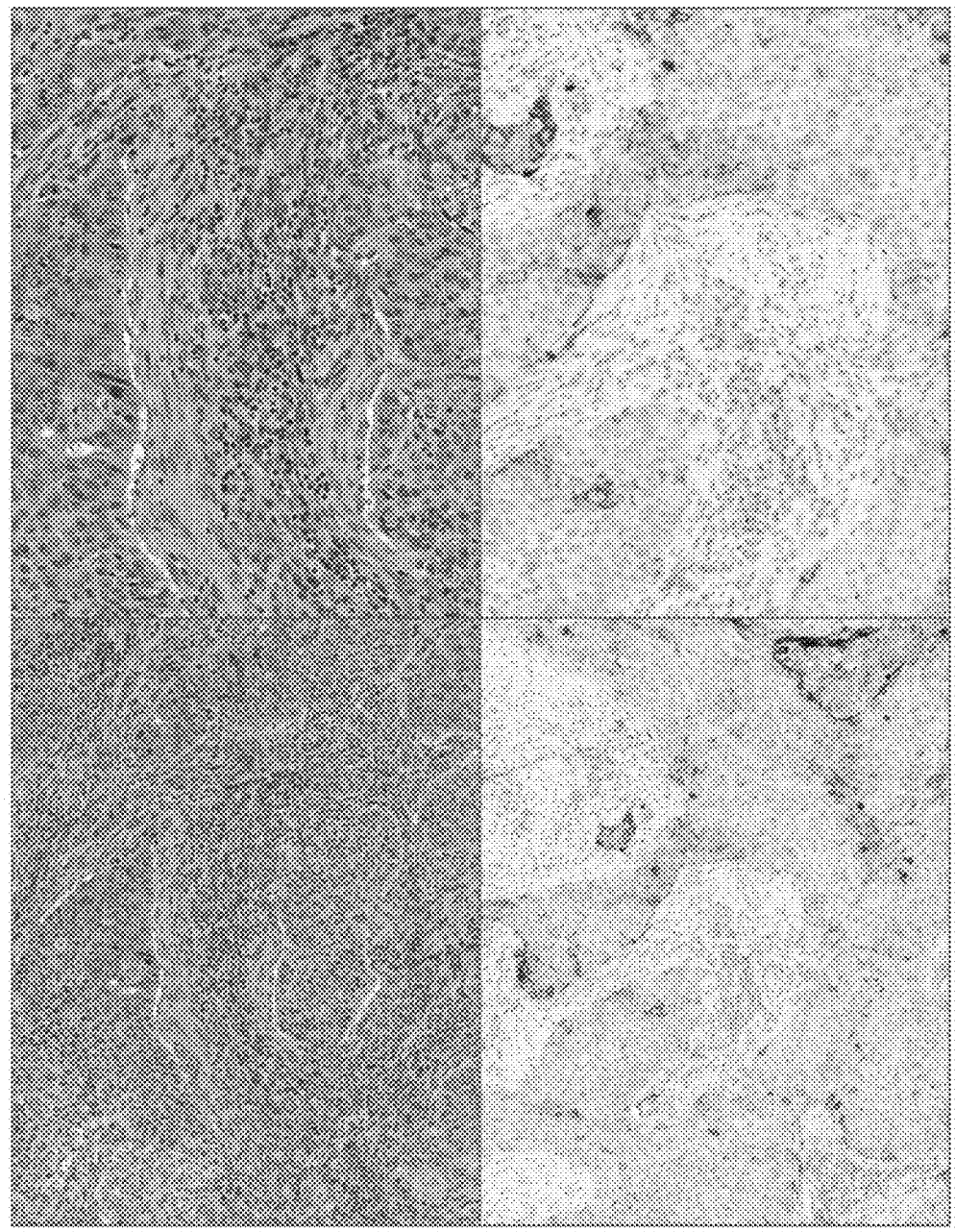
FIG. 22 illustrates an NSCLC stained with SP263 having plasma cells with weak diffuse cytoplasmic staining. Surrounding tumor cells demonstrate heterogeneous tumor cell membrane staining (10× left, 20× right, H&E top, DAB, bottom).

FIG. 22 illustrates plasma cells with weak diffuse cytoplasmic staining Surrounding tumor cells demonstrate heterogeneous tumor cell membrane staining (10× left, 20× right, H&E top, DAB, bottom).

Figure 23:
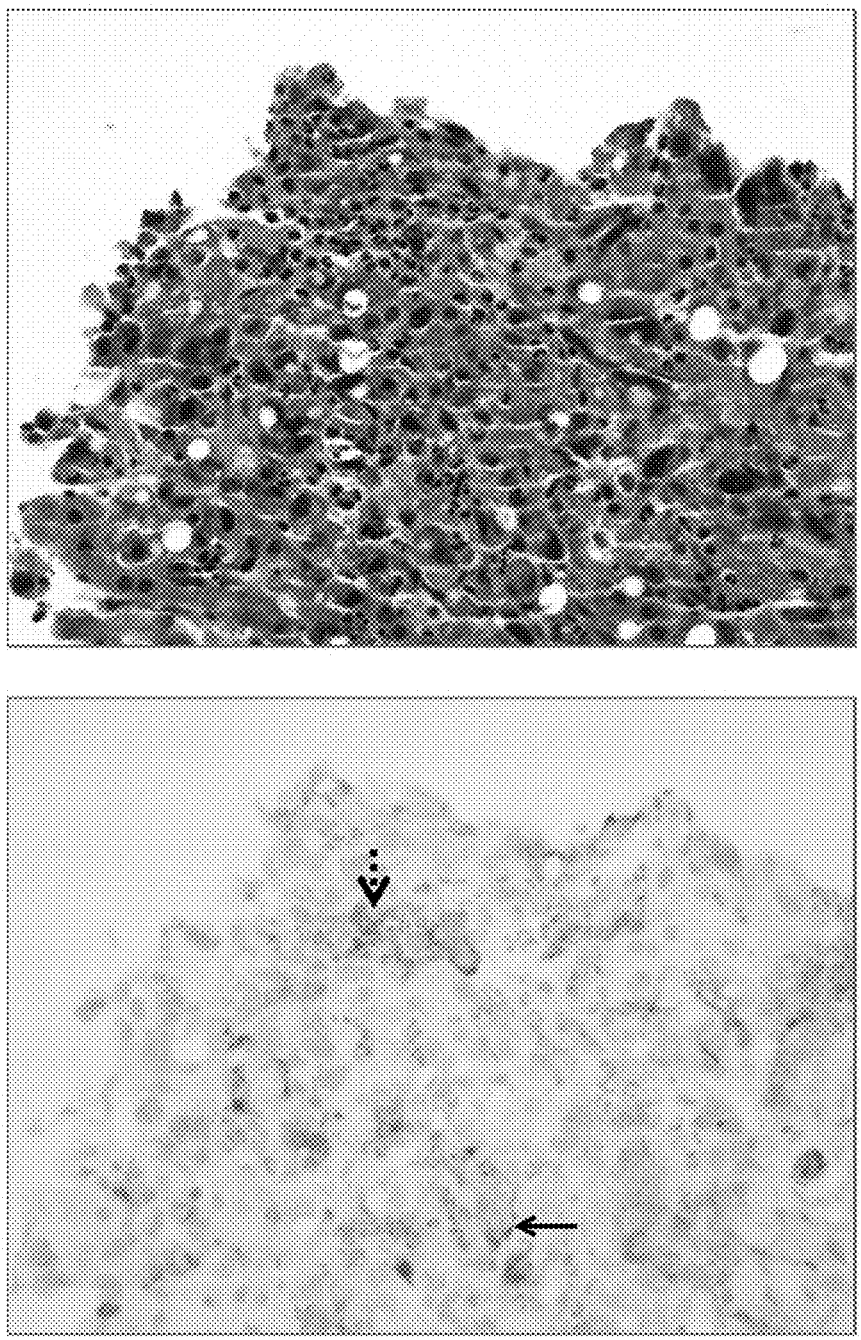
FIG. 23 illustrates an NSCLC stained with SP263 having neutrophils show PD-L1 expression (hatched arrow). Case also has moderate tumor cell membrane staining (black arrow) (40×). Top image is H&E stain; bottom image is DAB stain.

As seen at FIG. 23, neutrophils from the H&E show PD-L1 expression (hatched arrow). Case also has moderate tumor cell membrane staining (black arrow) (40×).

IIIB. Tissue Requirements

The above-described assay requires one serial tissue section for hematoxylin and eosin (H&E) staining, a second serial tissue section for negative control antibody staining, and a third serial tissue section for staining with the SP263 antibody. In addition, normal human term placenta tissue can be used as a control for the assay. This tissue shows moderate to strong uniform staining of the membrane and weak to strong uniform staining of the cytoplasm of trophoblast-lineage cells. Placental stromal tissue and vasculature can be used for assessment of any background staining. If H&E evaluation indicates that the patient specimen is inadequate then a new specimen should be obtained. Repeat staining of a specimen should be carried out on unstained slides if (1) the tissue run control slide does not exhibit acceptable staining; (2) the negative control case slide does not exhibit acceptable staining; or (3) the SP263 antibody stained case slide (the PD-L1 IHC slide) is not evaluable. If the last of these slides is not interpretable due to artifacts, edge effects, necrosis, lack of tissue, or any other reason, then the slide cannot be used for clinical evaluation. If controls are acceptable and the SP263 antibody stained slide is evaluable, the slide can be evaluated by a trained pathologist as described in the Scoring Criteria.

IIIC. Positive Tissue Control

A known positive control tissue fixed and processed in the same manner as the patient specimens should be run for each set of test conditions and with every SP263 antibody staining procedure performed. The control tissue (an index case) should be a fresh autopsy, biopsy, surgical specimen prepared and fixed as soon as possible in a manner identical to patient specimens. This tissue may be used to monitor all steps of specimen processing and staining A tissue section fixed or processed differently from the test specimen can be used as a control for reagents and staining but not for fixation or tissue preparation. A positive NSCLC case with moderate staining is more suitable for quality control than one that stains strongly; it can be used to detect minor levels of reagent degradation or out-of-specification issues that might be instrument-related. Positive membrane staining of neoplastic cells in the control tissue confirms antibody was applied and the instrument functioned properly. The positive tissue control should be used only to monitor performance; it should not be used to aid the clinical diagnosis of patient samples. Additionally, the assay illustrated herein can utilize as a positive control human term placental tissue, which shows moderate to strong uniform staining of the membrane and cytoplasm of trophoblast-lineage cells. Placental stromal tissue and vasculature can be used for assessment of any background staining. Exemplary images of placental tissue stained with the SP263 antibody are at FIGS. 7A and 7B.

IIID. Scoring Criteria

A PD-L1 IHC Clinical Status is assigned by a trained pathologist based on his or her evaluation of the percentage of specific PD-L1 IHC staining A cutoff for positivity and negativity is selected based on clinical data from known responders to the PD-1 axis therapeutic being used. In this exemplary embodiment, a 25% cutoff was selected. A clinical status of negative is assigned to cases with a total percent of tumor cells with membrane staining at any intensity of less than 25%. A clinical status of positive is assigned to cases with total percent of tumor cells with membrane staining at any intensity of greater than or equal to 25%. Clinical interpretation of NSCLC cases stained with the SP263 antibody was based on the criteria noted in table 3 above.

Images of various negative and positive staining patterns are provided in the subsequent sections.

IIID(1). Negative Cases

Negative staining intensity is characterized by the absence of any detectable signal or by membranous staining of any intensity in less than 25% of neoplastic cells.

Figure 24:
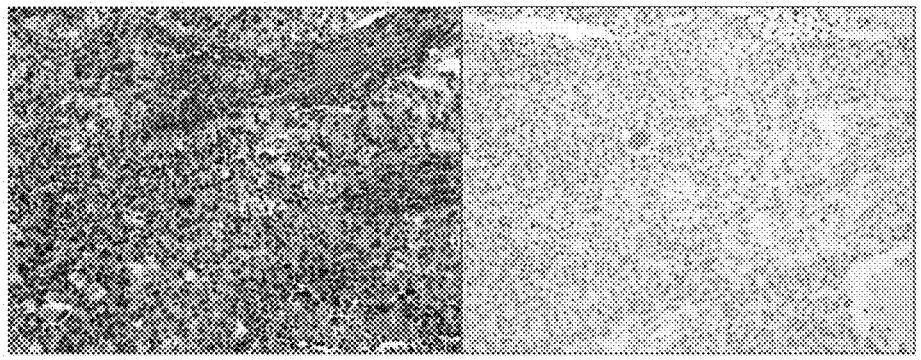
FIG. 24 illustrates an NSCLC stained with SP263 having negative tumor and immune cell staining (zero percent) at 20× magnification). Left image is H&E stain; right image is DAB stain.

Negative Case 1 is illustrated at FIG. 24. Negative tumor and immune cell staining (zero percent) is seen at 20× magnification.

Figure 25:
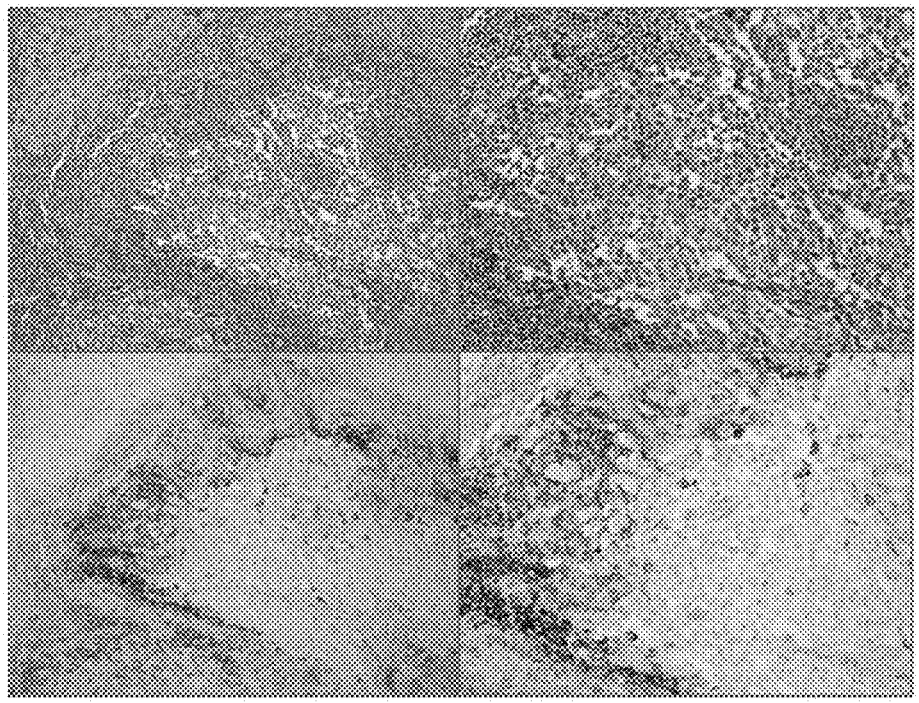
FIG. 25 illustrates an NSCLC stained with SP263 having tumor cell membrane with zero percent staining. Tumor area contains 30% immune cells at lower power view with 35% of immune cells showing PD-L1 expression (10× left, 20× right, H&E top, DAB, bottom).

Negative Case 2 is illustrated at FIG. 25. Tumor cell membrane with zero percent staining. Tumor area contains 30% immune cells at lower power view with 35% of immune cells showing PD-L1 expression (10× left, 20× right).

Figure 26:
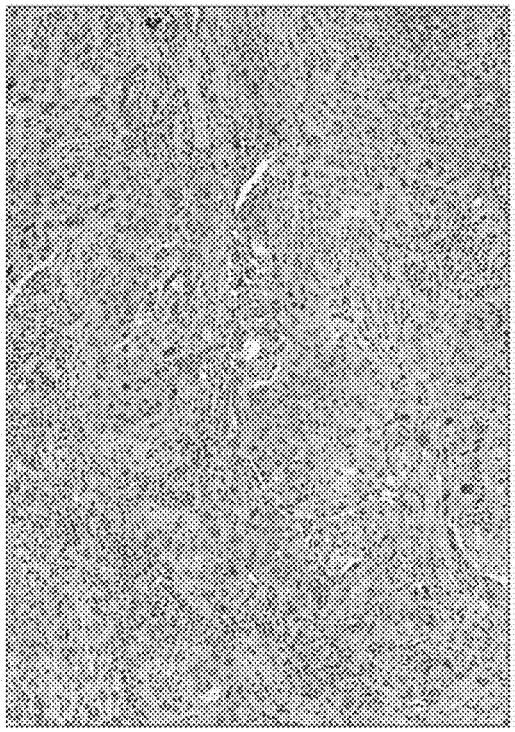
FIG. 26 illustrates an NSCLC stained with SP263 having tumor with 5% of cells demonstrating membrane staining (arrow). Tumor area (consisting of viable tumor and surrounding desmoplasia and inflammation) contains 10% immune cells and 50% of immune cells with PD-L1 expression (4×). Top image is H&E stain; bottom image is DAB stain.

Negative Case 3 is illustrated at FIG. 26. Tumor with 5% of cells demonstrating membrane staining (arrow). Tumor area (consisting of viable tumor and surrounding desmoplasia and inflammation) contains 10% immune cells and 50% of immune cells with PD-L1 expression (4×).

Figure 27:
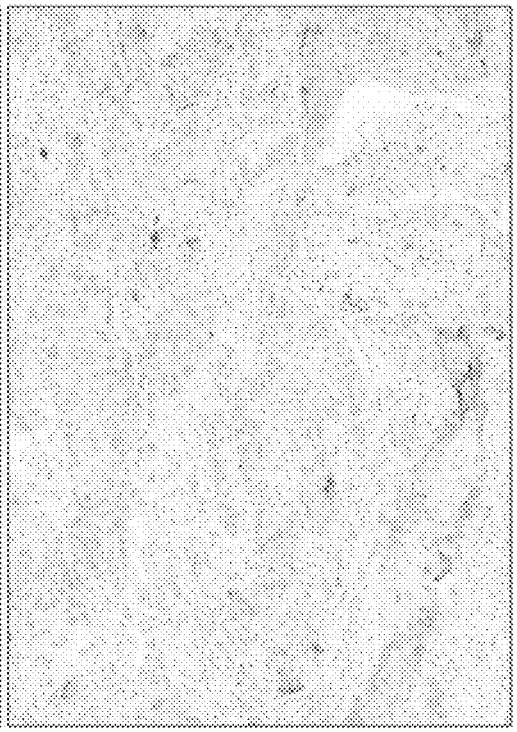
FIG. 27 illustrates an NSCLC stained with SP263 having tumor with 10% of cells demonstrating membrane staining in this field. Tumor area contains 10% immune cells and 10% of immune cells with PD-L1 expression (10×). Top image is H&E stain; bottom image is DAB stain.

Negative Case 4 is illustrated at FIG. 27. Tumor with 10% of cells demonstrating membrane staining in this field. Tumor area contains 10% immune cells and 10% of immune cells with PD-L1 expression (10×)

Negative Case 5 is illustrated at FIG. 28. Tumor with 15% of cells showing membrane staining (outlined region). Tumor-associated immune cell staining also seen. (2×).

Negative Case 6 is illustrated at FIG. 29. Tumor with 20% of cells demonstrating membrane staining in this field. Tumor area contains 5% immune cells and 10% of immune cells with PD-L1 expression (10×)

IIID(2). Positive Cases

Positive staining intensity was characterized by the presence of membranous staining of any intensity in greater than or equal to 25% of neoplastic cells.

Positive Case 1 is illustrated at FIG. 30. Tumor with 25% of cells demonstrating membrane staining in this field. Tumor area contains 5% immune cells and 5% of immune cells with PD-L1 expression (4×).

Positive Case 2 is illustrated at FIG. 31. Tumor with 35% of cells demonstrating membrane staining in this field. Tumor area (consisting of viable tumor and surrounding desmoplasia and inflammation) contains 10% immune cells and 5% of immune cells with PD-L1 expression (4×).

Positive Case 3 is illustrated at FIG. 32. Tumor with 50% of cells demonstrating membrane staining in this field. Tumor area (consisting of viable tumor and surrounding desmoplasia and inflammation) contains 10% immune cells and 5% of immune cells with PD-L1 expression (4×).

Positive Case 4 is illustrated at FIG. 33. Tumor with 70% of cells demonstrating membrane staining in this field. Tumor area contains 3% immune cells and 15% of immune cells with PD-L1 expression (4×).

Figure 34:
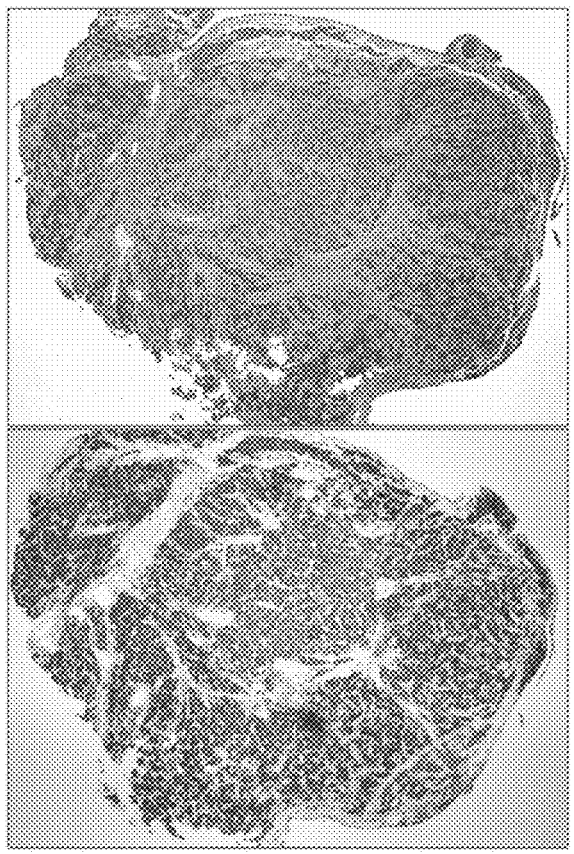
FIG. 34 illustrates an NSCLC stained with SP263 having tumor cell membrane staining at 100% (4×). Top image is H&E stain; bottom image is DAB stain.

Positive Case 5 is illustrated at FIG. 34, which exhibits tumor cell membrane staining at 100% (4×).

Figure 35:
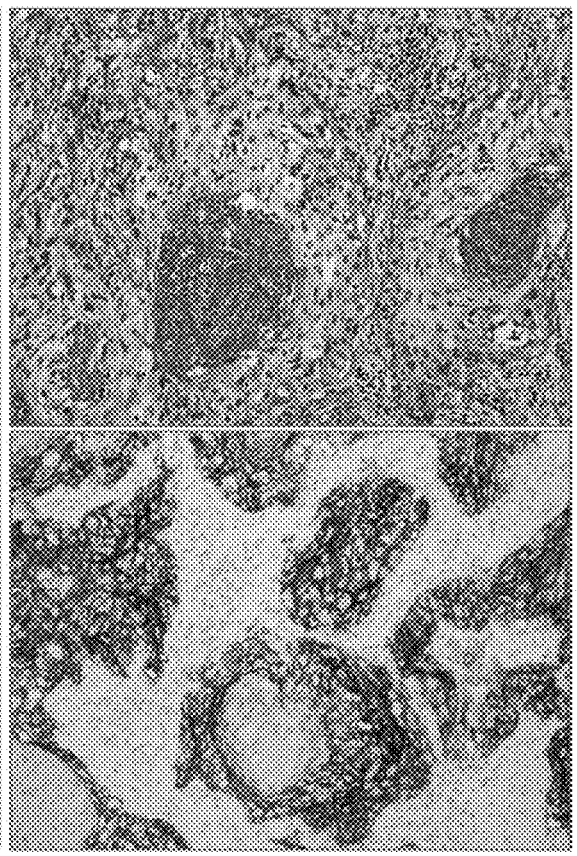
FIG. 35 illustrates an NSCLC stained with SP263 having positive tumor cell membrane staining with negative tumor immune cell staining (20×). Top image is H&E stain; bottom image is DAB stain.
Figure 36:
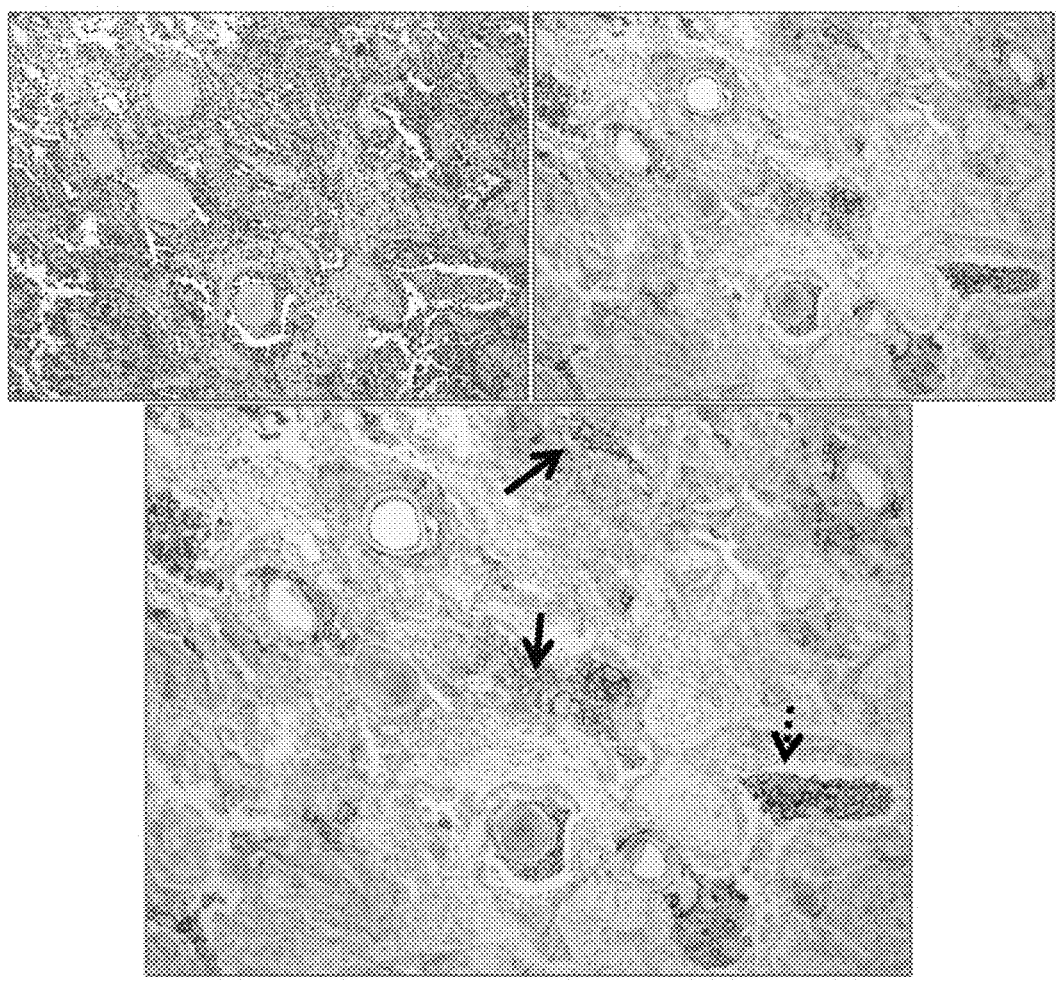
FIG. 36 illustrates an NSCLC stained with SP263 having alveolar macrophage staining associated with tumor (black arrow) and alveolar macrophage staining not associated with tumor (hatched arrow) (10×). Only the immune cells associated with tumor are enumerated. Top left image is H&E stain; top right and bottom images are DAB stain.

Positive Case 6 is illustrated at FIG. 35, which exhibits positive tumor cell membrane staining with negative tumor immune cell staining (20×).

IIID(3). Evaluation of Immune Cell Staining

Immune cell staining was captured for exploratory purposes. A variety of immune cells display staining, and include lymphocytes, macrophages, reticular dendritic cells, plasma cells and neutrophils. The H&E-stained slide is initially examined to determine the total percentage of the tumor area (tumor cells and any desmoplastic stroma) involved by immune cells. Areas not considered part of the tumor area include non-viable tumor such as areas with cautery or crush artifacts, and extensive necrosis. Normal lymphoid tissue uninvolved by neoplasm, for instance as seen in lymph nodes with metastatic tumor, is not evaluated as a part of the tumor area or immune cells involving the tumor. The PD-L1 IHC slide is then scored for the percentage of tumor-associated immune cells staining for PD-L1. In cases where positively-staining immune cells are intermixed with positively-staining tumor cells, it can be difficult to quantify the amount of staining for each component. Examples of immune cell interpretation are illustrated at FIGS. 36-40.

Immune Case 1 (FIG. 36) contains alveolar macrophage staining associated with tumor (black arrow) and alveolar macrophage staining not associated with tumor (hatched arrow) (10×). Only the immune cells associated with tumor are enumerated.

Figure 37:
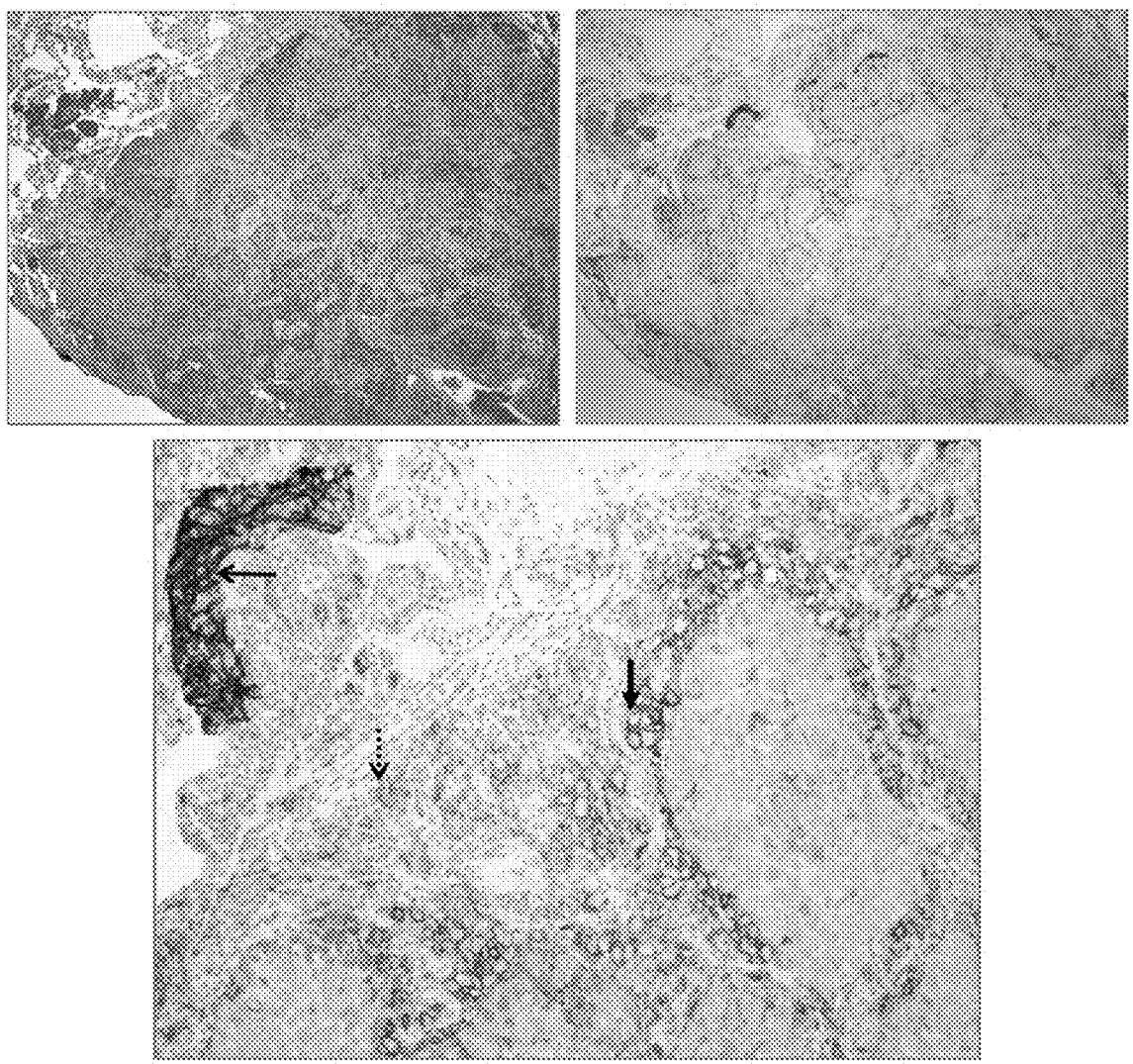
FIG. 37 illustrates an NSCLC stained with SP263. At 4× (top two images), the staining pattern appears to be predominantly tumor cell membrane staining; however examination at higher power (20×, bottom image) reveals the tumor is negative for PD-L1 with membranous (closed arrow head) and punctate (hatched arrow) immune cell staining. Dendritic cell staining is also seen (open arrow head). Top left image is H&E stain; top right and bottom images are DAB stain.

Immune Case 2 is illustrated at FIG. 37. At 4×, the staining pattern appears to be predominantly tumor cell membrane staining; however examination at higher power (20×) reveals the tumor is negative for PD-L1 with membranous (closed arrow head) and punctate (hatched arrow) immune cell staining. Dendritic cell staining is also seen (open arrow head).

Figure 39:
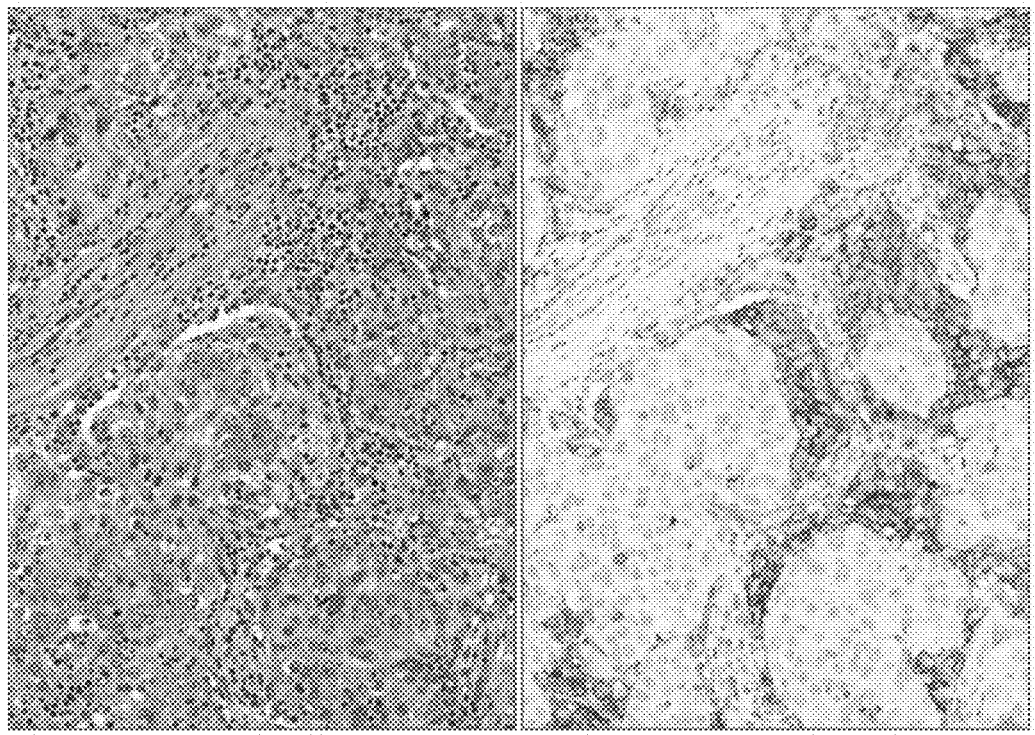
FIGS. 38 and 39 illustrate an SP263-negative NSCLC case with immune cell staining. At 4× (FIG. 38), the immune cells in the tumor area are better appreciated in the PD-L1-stained image and comprise 40% of the tumor area with 80% of immune cells staining (4×). Higher power (FIG. 39) confirms PD-L1 is highly expressed in the immune cell component of the tumor (20×). Top images are H&E stain; bottom images are DAB stain.
Figure 38:
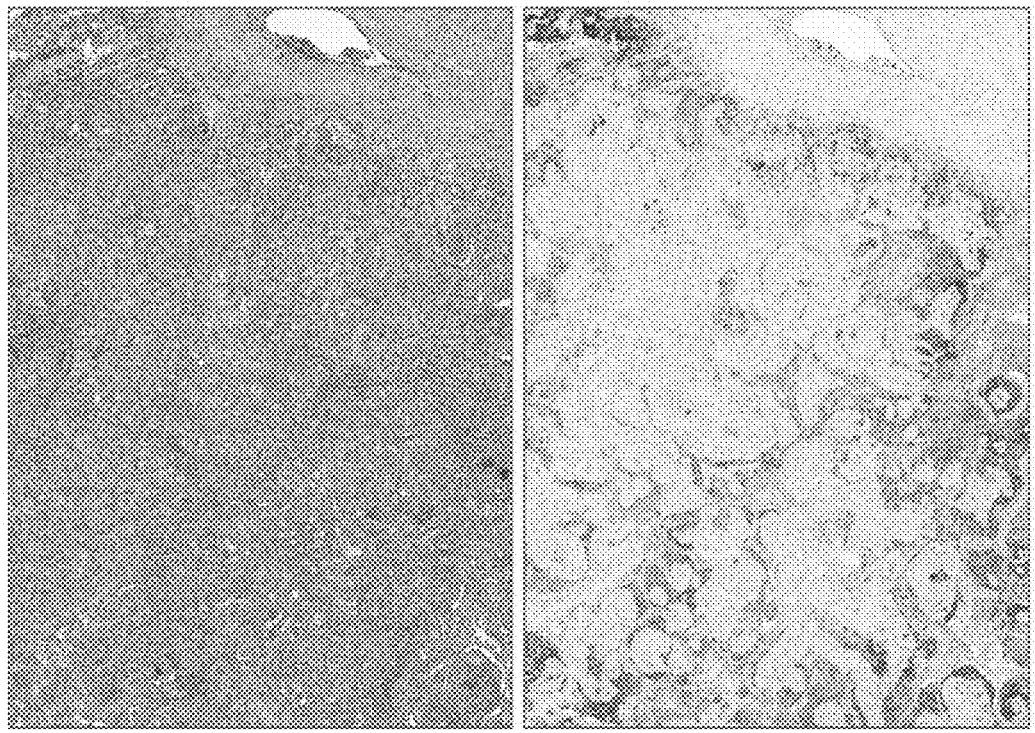

Immune Case 3 is illustrated at FIGS. 38 and 39, which is a negative tumor case with immune cell staining. At 4× (FIG. 38), the immune cells in the tumor area are better appreciated in the PD-L1-stained image and comprise 40% of the tumor area with 80% of immune cells staining (4×). Higher power (FIG. 39) confirms PD-L1 is highly expressed in the immune cell component of the tumor (20×).

Figure 40:
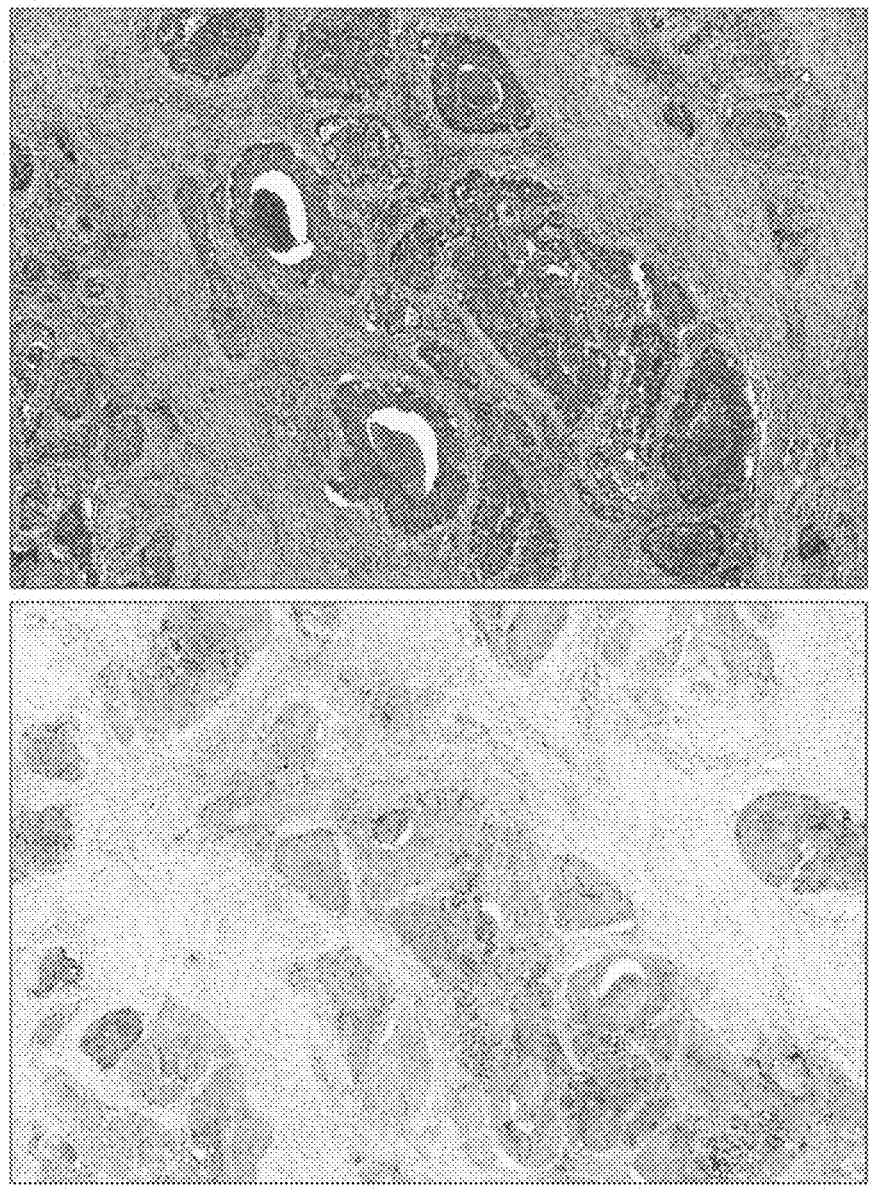
FIG. 40 illustrates an SP263-positive case with immune cell staining In this view, 15% of the tumor area contains immune cells with 30% of immune cells expressing PD-L1 (4×).
Figure 41:
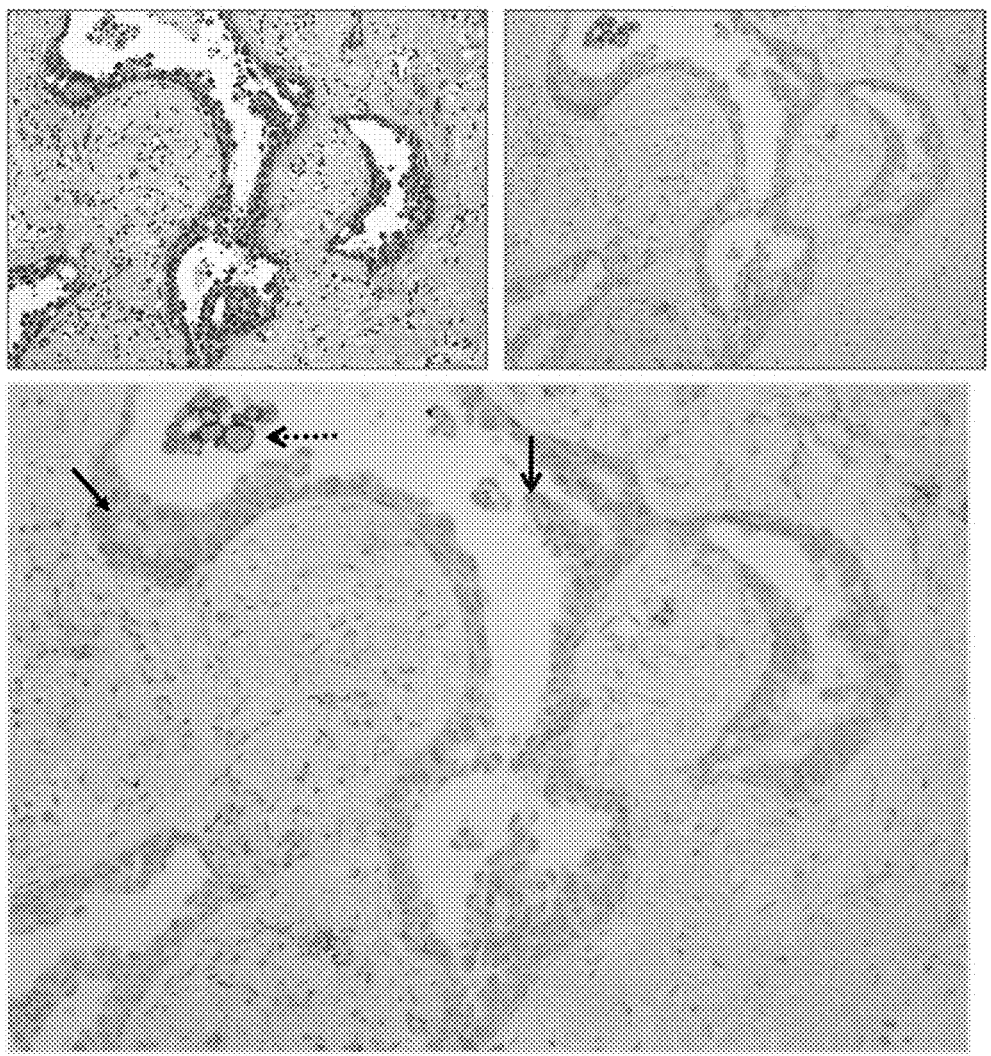
FIG. 41 illustrates an NSCLC stained with SP263 having weak cytoplasmic (black arrow) and weak membrane (closed arrow head) staining of the tumor. Staining of alveolar macrophages also seen (hatched arrow). Top images are 10×; bottom image is 20×. Top left image is H&E stain; top right and bottom images are DAB stain.
Figure 42:
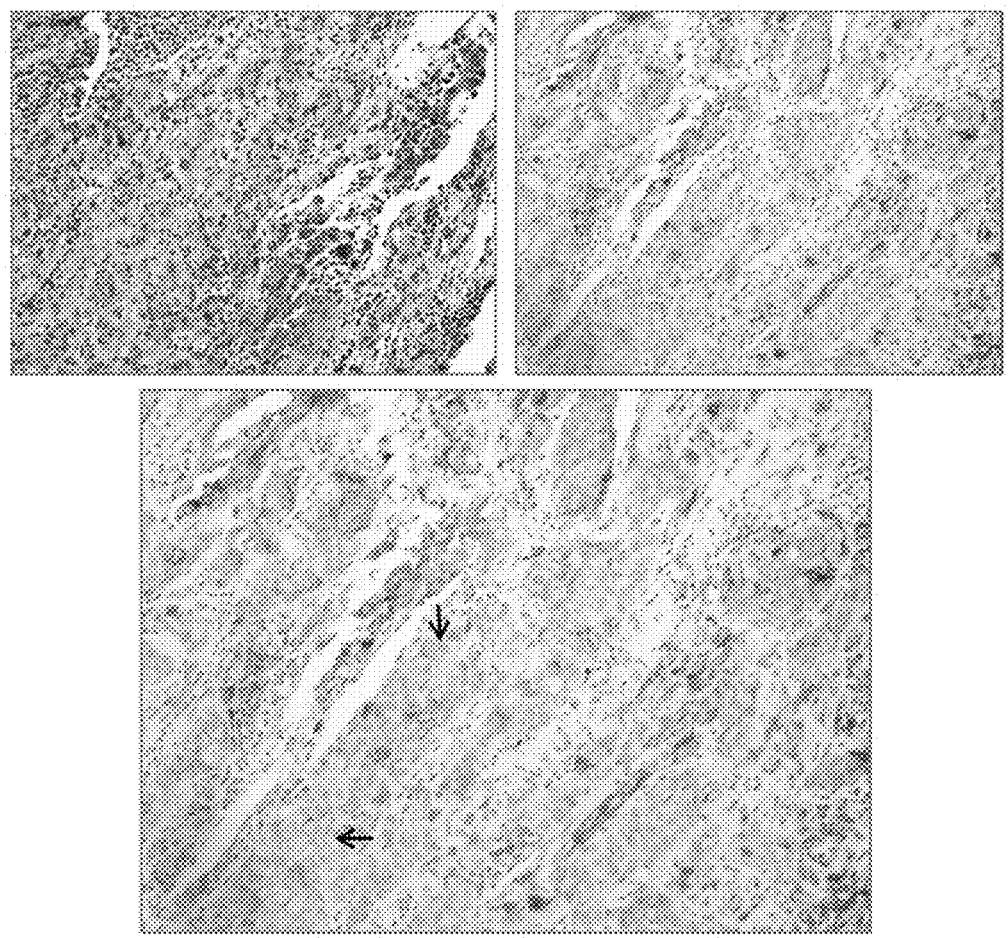
FIG. 42 illustrates an NSCLC stained with SP263 having weak membrane staining (black arrows). Top images are 10×; bottom image is 20×. Top left image is H&E stain; top right and bottom images are DAB stain.
Figure 44:
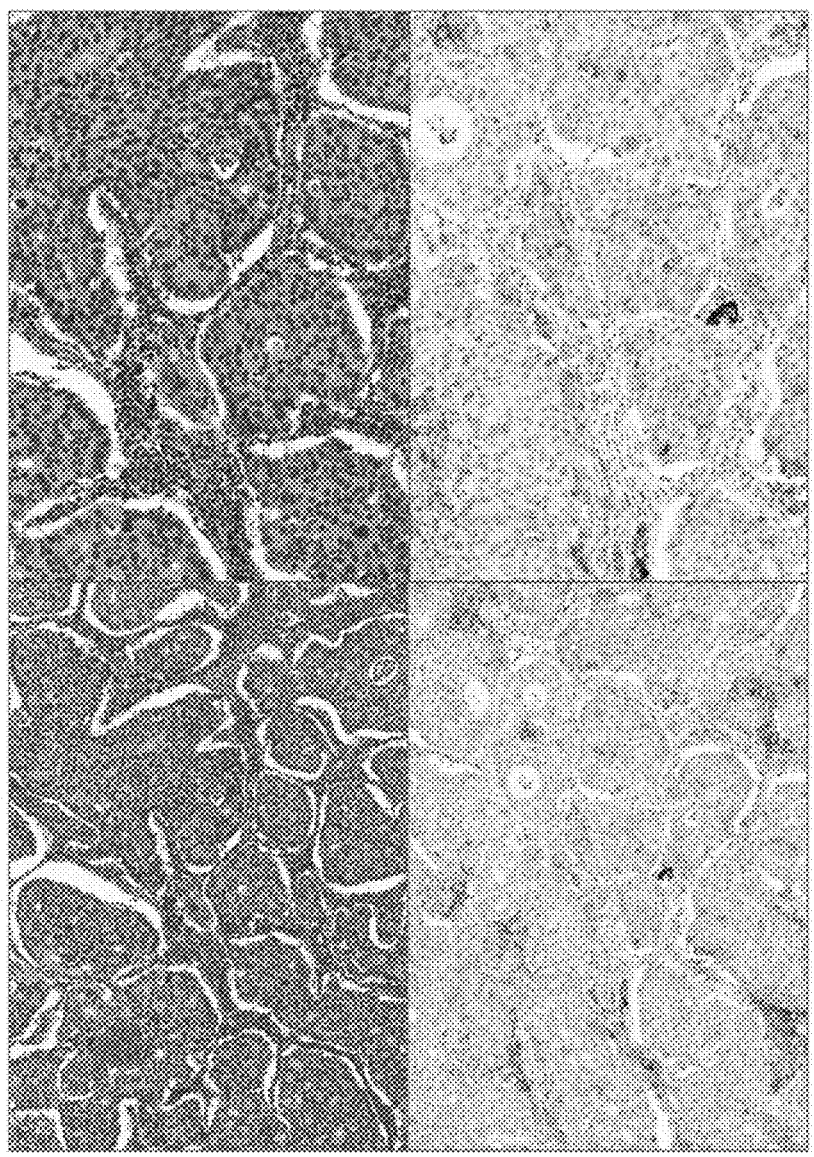
FIG. 44 illustrates an NSCLC tumor with weak cytoplasmic and weak membrane staining and immune cell staining (10× left, 20× right, top images are H&E stain; bottom images are DAB stain).
Figure 43:
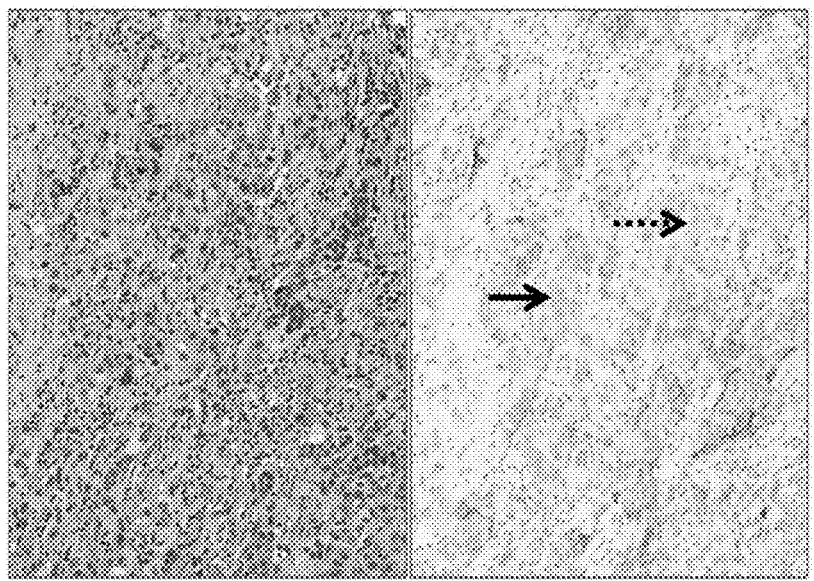
FIG. 43 illustrates an NSCLC tumor with weak cytoplasmic and weak membrane (black arrow) staining and only weak membrane staining (hatched arrow) at 20× magnification. Top images are H&E stain; bottom images are DAB stain.
Figure 46:
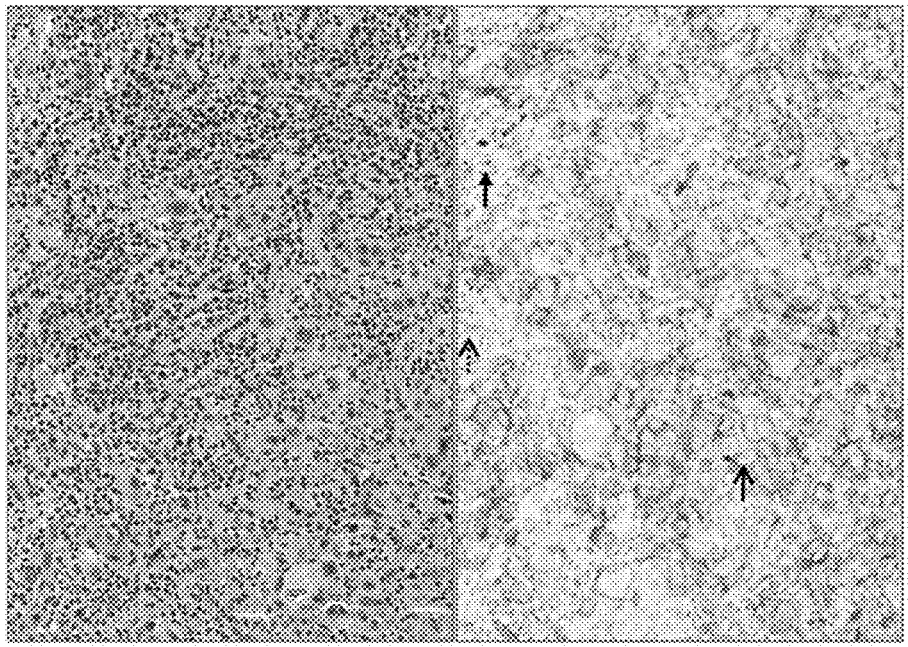
FIG. 46 illustrates an NSCLC tumor cell membrane (open arrow head) staining intermixed with diffuse (hatched arrow) and punctate (closed arrow head) immune cells staining (20×). Top images are H&E stain; bottom images are DAB stain.
Figure 45:
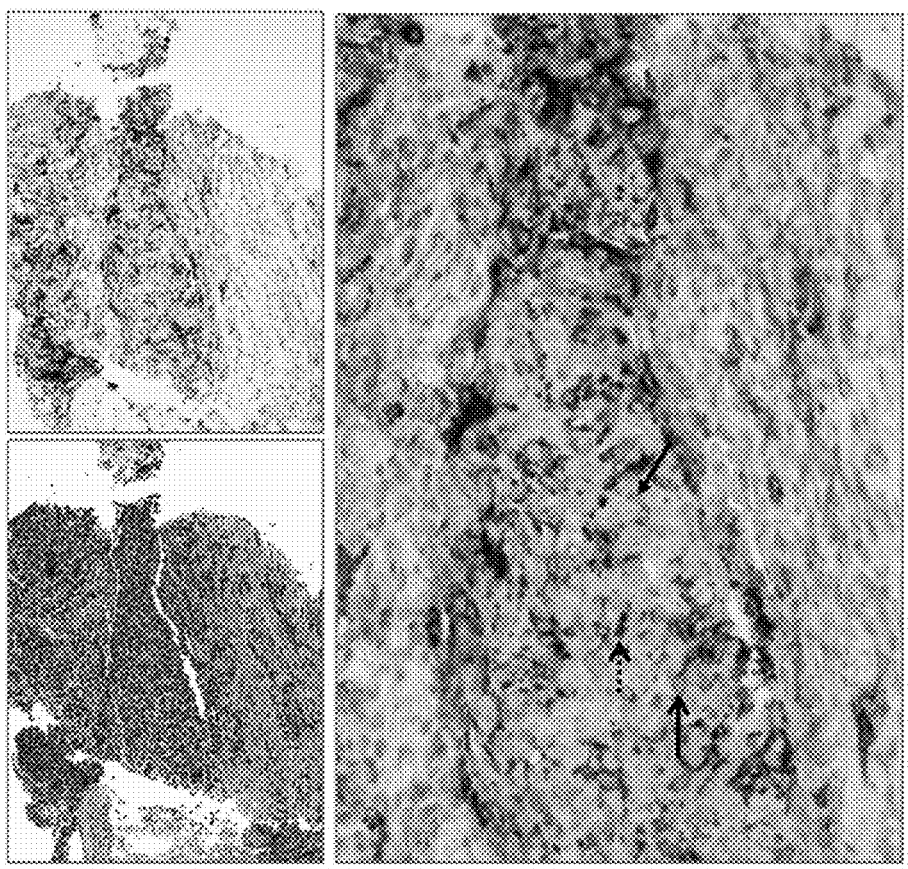
FIG. 45 illustrates an NSCLC tumor with membranous immune cell staining (black arrow) and punctate immune cell staining (hatched arrow) intermixed with tumor cell membrane staining (closed arrow head) (40×). Top left image is H&E stain; top right and bottom images are DAB stain.
Figure 47:
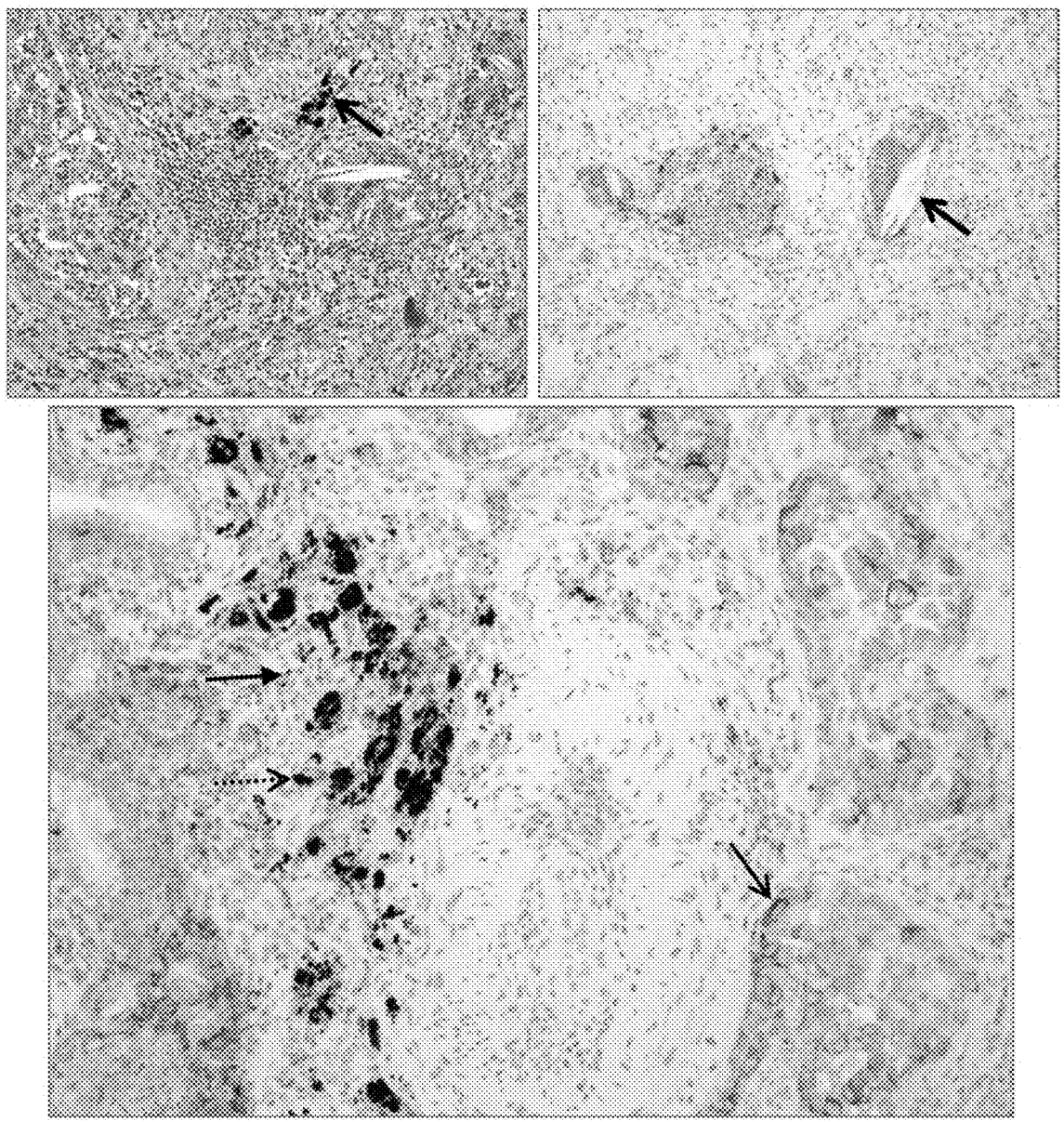
FIG. 47 illustrates an NSCLC case showing anthracosis (black arrow, top left image) and foreign body giant cell reaction (black arrow, top right image) not associated with case interpretation (top row, 20×). A different area of the case contains anthracotic pigment (bottom, hatched arrow) overlapping with punctate immune cell staining (bottom, closed arrow head) as well as tumor cell membrane staining (bottom, open arrow head) (20×).

Immune Case 4 is illustrated at FIG. 40, which is a positive tumor case with immune cell staining. In this view, 15% of the tumor area contains immune cells with 30% of immune cells expressing PD-L1 (4×).

IIID(4). Challenging Cases

Cases are given a clinical status according to percentage of tumor cells with membrane staining. Various staining patterns and morphologic features may make interpretation and quantification of tumor membrane staining difficult. Some cases may be particularly challenging due to the following issues:

Weak Cytoplasmic Staining

Some specimens may exhibit weak tumor cell cytoplasmic staining of the tumor cells that may be confused at low power with weak tumor cell membrane staining. For this reason when evaluating VENTANA PD-L1 (SP263) assay stained slides, weak staining should be confirmed with examination at higher powers to distinguish between tumor cell membranous and cytoplasmic staining.

Strong Immune Cell Staining Overlapping with Tumor Cell Staining

Some tumors may contain an extensive inflammatory component both surrounding the tumor and infiltrating within the tumor. In instances when strong staining is seen for both tumor and immune cells it can be challenging to differentiate and quantify the VENTANA PD-L1 (SP263) assay staining between the two cell populations. The presence of immune cells infiltrating the tumor should be confirmed using the H&E slide. The pattern of PD-L1 staining is utilized to help attribute expression to immune cells (punctate staining) and tumor cells (linear membrane staining)

Obscuring Endogenous Material

Occasionally in NSCLC samples endogenous material, such as anthracotic pigment, melanin pigment or hemosiderin, may obscure and interfere with interpretation of VENTANA PD-L1 (SP263) assay staining of tumor and immune cells. Comparison of the negative isotype control slide with the PD-L1 stained slide can aid in differentiating between biomarker staining and endogenous material.

Some challenging cases are shown at FIGS. 41-47.

Challenging Case 1 (FIG. 41) illustrates weak cytoplasmic (black arrow) and weak membrane (closed arrow head) staining of the tumor. Staining of alveolar macrophages also seen (hatched arrow). (20×).

Challenging Case 2 (FIG. 42) illustrates weak membrane staining (black arrows) at 20× magnification.

Challenging Case 3 (FIG. 43) illustrates tumor with weak cytoplasmic and weak membrane (black arrow) staining and only weak membrane staining (hatched arrow) at 20× magnification.

Challenging Case 4 (FIG. 44) illustrates a tumor with weak cytoplasmic and weak membrane staining and immune cell staining (10× left, 20× right).

Challenging Case 5 (FIG. 45) illustrates membranous immune cell staining (black arrow) and punctate immune cell staining (hatched arrow) intermixed with tumor cell membrane staining (closed arrow head) (40×).

Challenging Case 6 (FIG. 46) illustrates tumor cell membrane (open arrow head) staining intermixed with diffuse (hatched arrow) and punctate (closed arrow head) immune cells staining (20×).

Challenging Case 7 (FIG. 47) illustrates an NSCLC case showing anthracosis (black arrow, top left image) and foreign body giant cell reaction (black arrow, top right image) not associated with case interpretation (top row, 20×). A different area of the case contains anthracotic pigment (bottom, hatched arrow) overlapping with punctate immune cell staining (bottom, closed arrow head) as well as tumor cell membrane staining (bottom, open arrow head) (20×).

IV. Clinical Application

The above-described staining method and scoring algorithm was applied to a small training set from a Phase 1/2 study of MEDI4736 (NCT01693562). MEDI4736 is a human IgG1 mAb that blocks PD-L1 binding to PD-1 and CD-80 with high affinity and selectivity. Samples of both NSCLC and SCCHN are considered test positive when the membrane of ≥25% tumor cells stain for PD-L1 at any intensity. Inter-reader precision in determining PD-L1 status resulted in an overall percentage agreement of 97% and 92% for NSCLC and SCCHN, respectively. For both NSCLC and SCCHN, PD-L1+ patients had a higher response rate than PD-L1-patients.

The invention claimed is:

1. A histochemical method of classifying a tumor on the basis of PD-L1 expression, the method comprising:
   contacting a tissue sample from the tumor with an antibody specific for human PD-L1 or an antigen-binding fragment thereof in a manner that deposits a stain on the tumor sample in proximity to areas of the tumor sample to which the antibody binds, wherein the antibody comprises a heavy chain CDR1 comprising SEQ ID NO: 1, a heavy chain CDR2 comprising SEQ ID NO: 2, a heavy chain CDR3 comprising SEQ ID NO: 3, a light chain CDR1 comprising SEQ ID NO: 4, a light chain CDR2 comprising SEQ ID NO: 5, a light chain CDR3 comprising SEQ ID NO: 6;
   quantitating a percentage of tumor cells having membrane-staining; and
   scoring the tumor for PD-L1 expression, wherein the tumor is scored as PD-L1 positive if 25% or more tumor cells have membrane-staining.

2. The method of claim 1, wherein the stain is deposited by contacting the tissue sample with a second antibody capable of binding to the antibody specific for human PD-L1, wherein the second antibody comprises a detectable label that mediates deposition of the stain.

3. The method of claim 2, wherein the antibody specific for human PD-L1 is a rabbit monoclonal antibody, and the second antibody is an anti-rabbit Ig.

4. The method of claim 3, wherein the detectable label comprises an affinity tag, and wherein deposition of the stain further comprises contacting the sample with a binding entity specific for the affinity tag, the binding entity comprising an enzyme that catalyzes deposition of the stain.

5. The method of claim 4, wherein the affinity tag is a hapten and the binding entity is a third antibody that is specific for the hapten.

6. The method of claim 5, wherein the stain is the result of a reaction between the enzyme and a chromogen.

7. The method of claim 6, wherein the chromogen is selected from the group consisting of diaminobenzidine (DAB), 4-nitrophenylphospate (pNPP), fast red, bromochloroindolyl phosphate (BCIP), nitro blue tetrazolium (NBT), BCIP/NBT, fast red, AP Orange, AP blue, tetramethylbenzidine (TMB), 2,2'-azino-di-[3-ethylbenzothiazoline sulphonate] (ABTS), o-dianisidine, 4-chloronaphthol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazol (AEC), fuchsin, iodonitrotetrazolium (INT), tetrazolium blue and tetrazolium violet.

8. The method of claim 7, wherein the chromogen is DAB.

9. The method of claim 1, wherein scoring does not include quantitating anti-PD-L1 stained immune cells or stroma.

10. The method of claim 1, wherein the tumor is a non-small cell lung carcinoma (NSCLC) or squamous cell carcinoma of the head and neck (SCCHN).

* * * * *